US010265393B2

(12) United States Patent
King et al.

(10) Patent No.: US 10,265,393 B2
(45) Date of Patent: Apr. 23, 2019

(54) COMPOSITIONS AND METHODS FOR THE TREATMENT OR PREVENTION OF HUMAN IMMUNODEFICIENCY VIRUS INFECTION

(71) Applicant: GlobeImmune, Inc., Louisville, CO (US)

(72) Inventors: Thomas H. King, Denver, CO (US); David Apelian, Boonton Township, NJ (US)

(73) Assignee: GlobeImmune, Inc., Louisville, CO (US)

( * ) Notice: Subject to any disclaimer, the term of this patent is extended or adjusted under 35 U.S.C. 154(b) by 0 days.

(21) Appl. No.: 15/698,450

(22) Filed: Sep. 7, 2017

(65) Prior Publication Data

US 2018/0177865 A1    Jun. 28, 2018

Related U.S. Application Data

(62) Division of application No. 14/780,012, filed as application No. PCT/US2014/031811 on Mar. 26, 2014, now Pat. No. 9,782,473.

(60) Provisional application No. 61/805,299, filed on Mar. 26, 2013, provisional application No. 61/891,093, filed on Oct. 15, 2013.

(51) Int. Cl.
| | | |
|---|---|---|
| *A61K 39/21* | (2006.01) | |
| *A61K 39/12* | (2006.01) | |
| *C07K 14/16* | (2006.01) | |
| *A61K 9/00* | (2006.01) | |
| *A61K 45/06* | (2006.01) | |
| *C07K 14/005* | (2006.01) | |
| *C12N 7/00* | (2006.01) | |
| *A61K 39/00* | (2006.01) | |

(52) U.S. Cl.
CPC ............ *A61K 39/21* (2013.01); *A61K 9/0019* (2013.01); *A61K 39/12* (2013.01); *A61K 45/06* (2013.01); *C07K 14/005* (2013.01); *C12N 7/00* (2013.01); *A61K 2039/521* (2013.01); *A61K 2039/545* (2013.01); *A61K 2039/70* (2013.01); *C12N 2740/16022* (2013.01); *C12N 2740/16034* (2013.01); *C12N 2740/16222* (2013.01); *C12N 2740/16234* (2013.01)

(58) Field of Classification Search
None
See application file for complete search history.

(56) References Cited

U.S. PATENT DOCUMENTS

| | | |
|---|---|---|
| 4,775,622 A | 10/1988 | Hitzeman et al. |
| 5,234,830 A | 8/1993 | Oshima et al. |
| 5,310,654 A | 5/1994 | Isberg et al. |
| 5,413,914 A | 5/1995 | Franzusoff |
| 5,830,463 A | 11/1998 | Duke et al. |
| 5,858,378 A | 1/1999 | Bostwick |
| 5,919,651 A | 7/1999 | Hitzeman et al. |
| 6,733,993 B2 * | 5/2004 | Emini ............... C07K 14/005 424/199.1 |
| 7,083,787 B2 | 8/2006 | Duke et al. |
| 7,439,042 B2 | 10/2008 | Duke et al. |
| 7,465,454 B2 | 12/2008 | Franzusoff et al. |
| 7,563,447 B2 | 7/2009 | Franzusoff et al. |
| 7,595,060 B2 | 9/2009 | Duke et al. |
| 7,625,569 B2 | 12/2009 | Duke et al. |
| 7,632,511 B2 | 12/2009 | Duke et al. |
| 8,586,055 B2 * | 11/2013 | Felber ............... A61K 39/21 424/208.1 |
| 9,782,473 B2 | 10/2017 | King et al. |
| 2002/0044948 A1 | 4/2002 | Samir et al. |
| 2003/0035810 A1 | 2/2003 | Caplan |
| 2007/0172503 A1 | 7/2007 | Selitrennikoff et al. |
| 2007/0224208 A1 | 9/2007 | Guo et al. |
| 2008/0003239 A1 | 1/2008 | Duke et al. |
| 2008/0199493 A1 | 8/2008 | Picker et al. |
| 2009/0074805 A1 | 3/2009 | Duke et al. |
| 2009/0098154 A1 | 4/2009 | Franzusoff et al. |
| 2009/0142366 A1 | 6/2009 | Franzusoff et al. |
| 2009/0142367 A1 | 6/2009 | Franzusoff et al. |
| 2009/0304741 A1 | 12/2009 | Duke et al. |
| 2010/0034840 A1 | 2/2010 | Apelian et al. |
| 2010/0061995 A1 | 3/2010 | Carragher et al. |
| 2010/0104604 A1 | 4/2010 | Selitrennikoff et al. |
| 2010/0111912 A1 | 5/2010 | Apelian et al. |
| 2010/0150963 A1 | 6/2010 | Duke et al. |
| 2010/0189749 A1 | 7/2010 | Franzusoff et al. |

(Continued)

FOREIGN PATENT DOCUMENTS

| | | |
|---|---|---|
| EP | 0414404 | 2/1991 |
| FR | 2486400 | 1/1982 |

(Continued)

OTHER PUBLICATIONS

Official Action for European Patent Application No. 14775813.0 dated Mar. 16, 2018, 5 pages.
Barron et al., "Human Dendritic Cell Interactions with Whole Recombinant Yeast: Implications for HIV-1 Vaccine Development," Journal of Clinical Immunology, 2006, vol. 26, Iss. 3, pp. 251-264.
Benwell et al., "Essential and synergistic roles of IL1 and IL6 in human Th17 differentiation directed by TLR ligand-activated dendritic cells," Clinical Immunology, 2010, vol. 134, Iss. 2, pp. 178-187.

(Continued)

Primary Examiner — Nianxiang Zou
(74) Attorney, Agent, or Firm — Sheridan Ross P.C.

(57) ABSTRACT

Disclosed are yeast-based immunotherapeutic compositions, human immunodeficiency virus (HIV) antigens, and fusion proteins for the treatment and/or prevention of HIV infection and symptoms thereof, as well as methods of using the yeast-based immunotherapeutic compositions, HIV antigens, and fusion proteins for the prophylactic and/or therapeutic treatment of HIV and/or symptoms thereof.

19 Claims, 7 Drawing Sheets

Specification includes a Sequence Listing.

(56) References Cited

U.S. PATENT DOCUMENTS

| | | | |
|---|---|---|---|
| 2010/0196411 | A1 | 8/2010 | Duke et al. |
| 2010/0215678 | A1 | 8/2010 | Guo et al. |
| 2011/0150909 | A1 | 6/2011 | Franzusoff et al. |
| 2011/0256098 | A1 | 10/2011 | Apelian et al. |
| 2012/0107347 | A1 | 5/2012 | Hodge et al. |
| 2012/0294899 | A1 | 11/2012 | Epshtein et al. |
| 2012/0321664 | A1 | 12/2012 | Bellgrau et al. |

FOREIGN PATENT DOCUMENTS

| | | |
|---|---|---|
| WO | WO 2006/013106 | 2/2006 |
| WO | WO 2006/031264 | 3/2006 |
| WO | WO 2010/065626 | 6/2010 |
| WO | WO 2011/115914 | 9/2011 |
| WO | WO 2012/019127 | 2/2012 |
| WO | WO 2012/083302 | 6/2012 |
| WO | WO 2012/109404 | 8/2012 |
| WO | WO 2012/125998 | 9/2012 |
| WO | WO 2012/174220 | 12/2012 |
| WO | WO 2013/025972 | 2/2013 |

OTHER PUBLICATIONS

Bizzini et al. "Use of live *Saccharomyces cerevisiae* cells as a biological response modifier in experimental infections," FEMS Microbiology Immunology, 1990, vol. 64, pp. 155-168.

Brake et al. "alpha-Factor-directed synthesis and secretion of mature foreign proteins in *Saccharomyces cerevisiae*," Proceedings of the National Academy of Sciences USA, Aug. 1984, vol. 81, pp. 4642-4646.

Bugelski et al., "HIV protease inhibitors: effects on viral maturation and physiologic function in macrophages," Journal of Leukocyte Biology, 1994, vol. 56, No. 3, pp. 374-380.

Cereda et al., "Maturation of human dendritic cells with *Saccharomyces cerevisiae* (yeast) reduces the number and function of regulatory T cells and enhances the ratio of antigen-specific effectors to regulatory T cells," Vaccine, 2011, vol. 29, Iss. 31, pp. 4992-4999.

Eto et al., "Immunization with recombinant *Escherichia coli* expressing retinal S-antigen-induced experimental autoimmune uveitis (EAU) in Lewis rats", Cellular Immunology, vol. 147, No. 1 Mar. 1993, pp. 203-214.

Franzusoff, A. et al. "Yeasts Encoding Tumour Antigens in Cancer Immunotherapy," Expert Opinion on Biological Therapy, Apr. 2005, vol. 5, No. 4, pp. 565-575.

Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.

Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.

Haller et al., "Whole recombinant yeast-based immunotherapy induces potent T cell responses targeting HCV NS3 and Core proteins," Vaccine, 2007, vol. 25, Iss. 8, pp. 1452-1463.

King et al., "A Whole Recombinant Yeast-Based Therapeutic Vaccine Elicits HBV X, S and Core Specific T Cells in Mice and Activates Human T Cells Recognizing Epitopes Linked to Viral Clearance," PLOS One, 2014. vol. 9, Iss. 7, pp. e101904.

Klepfer et al. "Characterization of rabies glycoprotein expressed in yeast," Archives of Virology, 1993, vol. 128, pp. 269-286.

Liang et al., GenBank Accession No. ACV94677.1, Nov. 2011, 3 pages.

Lu, et al., "Mutation-Selective Tumor Remission with Ras-Targeted, Whole Yeast-Based Immunotherapy," Cancer Research, 2004, vol. 64, pp. 5084-5088.

Mizukoshi et al., "Activation of HIV-1 Gag-specific CD8+ T cells by yeast-derived VLP-pulsed dendritic cells is influenced by the level of mannose on the VLP antigen," Microbes and Infection, 2009, vol. 11, Iss. 2, pp. 191-197.

Moore et al., "Novel yeast-based vaccine 1-40, against HIV-SF2 gp160 promotes a cytotoxic 43-62 cell response.", FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.

Schreuder et al. "Yeast expressing hepatitis B virus surface antigen determinants on its surface: implications fora possible oral vaccine," Vaccine, Apr. 1996, vol. 14, No. 5, pp. 383-388.

Sinai et al. "Enhancement of Resistance to Infectious Diseases by Oral Administration of Brewer's Yeast," Infection and Immunity, May 1974, vol. 9, No. 5, pp. 781-787.

Stubbs, et al., "Whole Recombinant Yeast Vaccine Activates Dendritic Cells and Elicits Protective Cell-Mediated Immunity," National Medicine, May 2001, vol. 7, No. 5, pp, 1-5.

Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.

International Search Report and Written Opinion for International (PCT) Patent Application No. PCT/US14/31811 dated Nov. 25, 2014, 13 pages.

International Preliminary Report on Patentability for International (PCT) Patent Application No. PCT/US14/31811 dated Oct. 8, 2015, 9 pages.

Partial European Search Report for European Patent Application No. 14775813.0 dated Sep. 30, 2016, 11 pages.

Extended European Search Report for European Patent Application No. 14775813.0 dated Feb. 2, 2017, 13 pages.

Official Action for U.S. Appl. No. 14/780,012 dated Oct. 14, 2016, 8 pages.

Official Action for U.S. Appl. No. 14/780,012 dated Feb. 2, 2017, 12 pages.

Notice of Allowance for U.S. Appl. No. 14/780,012 dated Jun. 12, 2017, 7 pages.

Official Action (with English translation) for Taiwan Patent Application No. 103111327 dated Dec. 20, 2017, 10 pages.

* cited by examiner

SEQUENCE LISTING

<160> NUMBER OF SEQ ID NOS: 86

<210> SEQ ID NO 1
<211> LENGTH: 377
<212> TYPE: PRT
<213> ORGANISM: Human immunodeficiency virus

<400> SEQUENCE: 1

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365
```

```
Gln Val Thr Asn Ser Ala Thr Ile Met
    370                 375

<210> SEQ ID NO 2
<211> LENGTH: 245
<212> TYPE: PRT
<213> ORGANISM: Human immunodeficiency virus

<400> SEQUENCE: 2

Pro Ile Val Gln Asn Ile Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu Ala Glu Ala Met Ser Gln Val Thr Asn
225                 230                 235                 240

Ser Ala Thr Ile Met
            245

<210> SEQ ID NO 3
<211> LENGTH: 325
<212> TYPE: PRT
<213> ORGANISM: Human immunodeficiency virus

<400> SEQUENCE: 3

Pro Ile Val Gln Asn Ile Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60
```

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu Ala Glu Ala Met Ser Gln Val Thr Asn
225                 230                 235                 240

Ser Ala Thr Ile Met Lys Glu Ala Leu Leu Ala Thr Gly Ala Asp Asp
                245                 250                 255

Thr Val Leu Glu Glu Met Ser Leu Pro Gly Arg Trp Lys Pro Lys Met
            260                 265                 270

Ile Gly Gly Ile Gly Gly Phe Ile Lys Val Arg Gln Tyr Asp Gln Ile
        275                 280                 285

Leu Ile Glu Ile Cys Gly His Lys Ala Ile Gly Thr Val Leu Val Gly
    290                 295                 300

Pro Thr Pro Val Asn Ile Ile Gly Arg Asn Leu Leu Thr Gln Ile Gly
305                 310                 315                 320

Cys Thr Leu Asn Phe
                325

<210> SEQ ID NO 4
<211> LENGTH: 497
<212> TYPE: PRT
<213> ORGANISM: Human immunodeficiency virus

<400> SEQUENCE: 4

Pro Ile Val Gln Asn Ile Gln Gly Gln Met Val His Gln Ala Ile Ser
1               5                   10                  15

Pro Arg Thr Leu Asn Ala Trp Val Lys Val Val Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Val His Pro Val His Ala Gly Pro Ile Ala Pro Gly Gln Met
                85                  90                  95

Arg Glu Pro Arg Gly Ser Asp Ile Ala Gly Thr Thr Ser Thr Leu Gln
            100                 105                 110

```
Glu Gln Ile Gly Trp Met Thr Asn Asn Pro Ile Pro Val Gly Glu
            115                 120                 125
Ile Tyr Lys Arg Trp Ile Ile Leu Gly Leu Asn Lys Ile Val Arg Met
130                 135                 140
Tyr Ser Pro Thr Ser Ile Leu Asp Ile Arg Gln Gly Pro Lys Glu Pro
145                 150                 155                 160
Phe Arg Asp Tyr Val Asp Arg Phe Tyr Lys Thr Leu Arg Ala Glu Gln
                165                 170                 175
Ala Ser Gln Glu Val Lys Asn Trp Met Thr Glu Thr Leu Leu Val Gln
            180                 185                 190
Asn Ala Asn Pro Asp Cys Lys Thr Ile Leu Lys Ala Leu Gly Pro Ala
        195                 200                 205
Ala Thr Leu Glu Glu Met Met Thr Ala Cys Gln Gly Val Gly Gly Pro
210                 215                 220
Gly His Lys Ala Arg Val Leu Ala Glu Ala Met Ser Gln Val Thr Asn
225                 230                 235                 240
Ser Ala Thr Ile Met Lys Glu Ala Leu Leu Ala Thr Gly Ala Asp Asp
                245                 250                 255
Thr Val Leu Glu Glu Met Ser Leu Pro Gly Arg Trp Lys Pro Lys Met
            260                 265                 270
Ile Gly Gly Ile Gly Gly Phe Ile Lys Val Arg Gln Tyr Asp Gln Ile
        275                 280                 285
Leu Ile Glu Ile Cys Gly His Lys Ala Ile Gly Thr Val Leu Val Gly
290                 295                 300
Pro Thr Pro Val Asn Ile Ile Gly Arg Asn Leu Leu Thr Gln Ile Gly
305                 310                 315                 320
Cys Thr Leu Asn Phe Pro Ile Ser Pro Ile Glu Thr Val Pro Val Lys
                325                 330                 335
Leu Lys Pro Gly Met Asp Gly Pro Lys Val Lys Gln Trp Pro Leu Thr
            340                 345                 350
Glu Glu Lys Ile Lys Ala Leu Val Glu Ile Cys Thr Glu Met Glu Lys
        355                 360                 365
Glu Gly Lys Ile Ser Lys Ile Gly Pro Glu Asn Pro Tyr Asn Thr Pro
370                 375                 380
Val Phe Ala Ile Lys Lys Lys Asp Ser Thr Lys Trp Arg Lys Leu Val
385                 390                 395                 400
Asp Phe Arg Glu Leu Asn Lys Arg Thr Gln Asp Phe Trp Glu Val Gln
                405                 410                 415
Leu Gly Ile Pro His Pro Ala Gly Leu Lys Lys Lys Ser Val Thr
            420                 425                 430
Val Leu Ala Val Gly Asp Ala Tyr Phe Ser Val Pro Leu Asp Glu Asp
435                 440                 445
Phe Arg Lys Tyr Thr Ala Phe Thr Ile Pro Ser Ile Asn Asn Glu Thr
450                 455                 460
Pro Gly Ile Arg Tyr Gln Tyr Asn Val Leu Pro Gln Gly Trp Lys Gly
465                 470                 475                 480
Ser Pro Ala Ile Phe Gln Ser Ser Met Thr Lys Ile Leu Glu Pro Phe
                485                 490                 495
Arg

<210> SEQ ID NO 5
<211> LENGTH: 567
<212> TYPE: PRT
```

<213> ORGANISM: Human immunodeficiency virus

<400> SEQUENCE: 5

```
Pro Ile Val Gln Asn Ile Gln Gly Gln Met Val His Gln Ala Ile Ser
1               5                   10                  15
Pro Arg Thr Leu Asn Ala Trp Val Lys Val Val Glu Glu Lys Ala Phe
            20                  25                  30
Ser Pro Glu Val Ile Pro Met Phe Ser Ala Leu Ser Glu Gly Ala Thr
        35                  40                  45
Pro Gln Asp Leu Asn Thr Met Leu Asn Thr Val Gly Gly His Gln Ala
    50                  55                  60
Ala Met Gln Met Leu Lys Glu Thr Ile Asn Glu Glu Ala Ala Glu Trp
65                  70                  75                  80
Asp Arg Val His Pro Val His Ala Gly Pro Ile Ala Pro Gly Gln Met
                85                  90                  95
Arg Glu Pro Arg Gly Ser Asp Ile Ala Gly Thr Thr Ser Thr Leu Gln
            100                 105                 110
Glu Gln Ile Gly Trp Met Thr Asn Asn Pro Pro Ile Pro Val Gly Glu
        115                 120                 125
Ile Tyr Lys Arg Trp Ile Ile Leu Gly Leu Asn Lys Ile Val Arg Met
    130                 135                 140
Tyr Ser Pro Thr Ser Ile Leu Asp Ile Arg Gln Gly Pro Lys Glu Pro
145                 150                 155                 160
Phe Arg Asp Tyr Val Asp Arg Phe Tyr Lys Thr Leu Arg Ala Glu Gln
                165                 170                 175
Ala Ser Gln Glu Val Lys Asn Trp Met Thr Glu Thr Leu Leu Val Gln
            180                 185                 190
Asn Ala Asn Pro Asp Cys Lys Thr Ile Leu Lys Ala Leu Gly Pro Ala
        195                 200                 205
Ala Thr Leu Glu Glu Met Met Thr Ala Cys Gln Gly Val Gly Gly Pro
    210                 215                 220
Gly His Lys Ala Arg Val Leu Ala Glu Ala Met Ser Gln Val Thr Asn
225                 230                 235                 240
Ser Ala Thr Ile Met Lys Glu Ala Leu Leu Ala Thr Gly Ala Asp Asp
                245                 250                 255
Thr Val Leu Glu Glu Met Ser Leu Pro Gly Arg Trp Lys Pro Lys Met
            260                 265                 270
Ile Gly Gly Ile Gly Gly Phe Ile Lys Val Arg Gln Tyr Asp Gln Ile
        275                 280                 285
Leu Ile Glu Ile Cys Gly His Lys Ala Ile Gly Thr Val Leu Val Gly
    290                 295                 300
Pro Thr Pro Val Asn Ile Ile Gly Arg Asn Leu Leu Thr Gln Ile Gly
305                 310                 315                 320
Cys Thr Leu Asn Phe Tyr Val Asp Gly Ala Ala Asn Arg Glu Thr Lys
                325                 330                 335
Leu Gly Lys Ala Gly Tyr Val Thr Asn Arg Gly Arg Gln Lys Val Val
            340                 345                 350
Thr Leu Thr Asp Thr Thr Asn Gln Lys Thr Glu Leu Gln Ala Ile Tyr
        355                 360                 365
Leu Ala Leu Gln Asp Ser Gly Leu Glu Val Asn Ile Val Thr Asp Ser
    370                 375                 380
Gln Tyr Ala Leu Gly Ile Ile Gln Ala Gln Pro Asp Gln Ser Glu Ser
385                 390                 395                 400
```

```
Glu Leu Val Asn Gln Ile Ile Glu Gln Leu Ile Lys Lys Glu Lys Val
                405                 410                 415

Tyr Leu Ala Trp Val Pro Ala His Lys Gly Ile Gly Gly Asn Glu Gln
            420                 425                 430

Val Asp Lys Leu Val Ser Ala Gly Ile Arg Lys Val Leu Phe Leu Asp
        435                 440                 445

Gly Ile Asp Lys Ala Gln Asp Glu His Glu Lys Tyr His Ser Asn Trp
    450                 455                 460

Arg Ala Met Ala Ser Asp Phe Asn Leu Pro Pro Val Val Ala Lys Glu
465                 470                 475                 480

Ile Val Ala Ser Cys Asp Lys Cys Gln Leu Lys Gly Glu Ala Met His
                485                 490                 495

Gly Gln Val Asp Cys Ser Pro Gly Ile Trp Gln Leu Asp Cys Thr His
            500                 505                 510

Leu Glu Gly Lys Val Ile Leu Val Ala Val His Val Ala Ser Gly Tyr
        515                 520                 525

Ile Glu Ala Glu Val Ile Pro Ala Glu Thr Gly Gln Glu Thr Ala Tyr
    530                 535                 540

Phe Leu Leu Lys Leu Ala Gly Arg Trp Pro Val Lys Thr Ile His Thr
545                 550                 555                 560

Asp Asn Gly Ser Asn Phe Thr
                565

<210> SEQ ID NO 6
<211> LENGTH: 122
<212> TYPE: PRT
<213> ORGANISM: Human immunodeficiency virus

<400> SEQUENCE: 6

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr
        115                 120

<210> SEQ ID NO 7
<211> LENGTH: 129
<212> TYPE: PRT
<213> ORGANISM: Human immunodeficiency virus

<400> SEQUENCE: 7

Phe Leu Gly Phe Leu Gly Ala Ala Gly Ser Thr Met Gly Ala Ala Ser
1               5                   10                  15

Met Thr Leu Thr Val Gln Ala Arg Gln Leu Leu Ser Gly Ile Val Gln
            20                  25                  30
```

-continued

```
Gln Gln Asn Leu Leu Arg Ala Ile Glu Ala Gln His Leu Leu
         35                  40                  45

Gln Leu Thr Val Trp Gly Ile Lys Gln Leu Gln Ala Arg Ile Leu Ala
 50                      55                  60

Val Glu Arg Tyr Leu Lys Asp Gln Gln Leu Leu Gly Ile Trp Gly Cys
 65                  70                  75                  80

Ser Gly Lys Leu Ile Cys Thr Thr Trp Leu Trp Tyr Ile Lys Leu Phe
                 85                  90                  95

Ile Met Ile Val Gly Gly Leu Val Gly Leu Arg Ile Val Phe Ala Val
                100                 105                 110

Leu Ser Ile Val Asn Arg Val Arg Gln Gly Tyr Ser Pro Leu Ser Phe
            115                 120                 125

Gln

<210> SEQ ID NO 8
<211> LENGTH: 512
<212> TYPE: PRT
<213> ORGANISM: Human immunodeficiency virus

<400> SEQUENCE: 8

Lys Glu Ala Leu Leu Ala Thr Gly Ala Asp Asp Thr Val Leu Glu Glu
 1               5                  10                  15

Met Ser Leu Pro Gly Arg Trp Lys Pro Lys Met Ile Gly Gly Ile Gly
                20                  25                  30

Gly Phe Ile Lys Val Arg Gln Tyr Asp Gln Ile Leu Ile Glu Ile Cys
             35                  40                  45

Gly His Lys Ala Ile Gly Thr Val Leu Val Gly Pro Thr Pro Val Asn
 50                  55                  60

Ile Ile Gly Arg Asn Leu Leu Thr Gln Ile Gly Cys Thr Leu Asn Phe
 65                  70                  75                  80

Met Gly Ala Arg Ala Ser Val Leu Ser Gly Gly Glu Leu Asp Arg Trp
                 85                  90                  95

Glu Lys Ile Arg Leu Arg Pro Gly Gly Lys Lys Tyr Lys Leu Lys
                100                 105                 110

His Ile Val Trp Ala Ser Arg Glu Leu Glu Arg Phe Ala Val Asn Pro
            115                 120                 125

Gly Leu Leu Glu Thr Ser Glu Gly Cys Arg Gln Ile Leu Gly Gln Leu
        130                 135                 140

Gln Pro Ser Leu Gln Thr Gly Ser Glu Glu Leu Arg Ser Leu Tyr Asn
145                 150                 155                 160

Thr Val Ala Thr Leu Tyr Cys Val His Gln Arg Ile Glu Ile Lys Asp
                165                 170                 175

Thr Lys Glu Ala Leu Asp Lys Ile Glu Glu Gln Asn Lys Ser Lys
            180                 185                 190

Lys Lys Ala Gln Gln Ala Ala Ala Asp Thr Gly His Ser Asn Gln Val
        195                 200                 205

Ser Gln Asn Tyr Pro Ile Val Gln Asn Ile Gln Gly Gln Met Val His
    210                 215                 220

Gln Ala Ile Ser Pro Arg Thr Leu Asn Ala Trp Val Lys Val Val Glu
225                 230                 235                 240

Glu Lys Ala Phe Ser Pro Glu Val Ile Pro Met Phe Ser Ala Leu Ser
                245                 250                 255

Glu Gly Ala Thr Pro Gln Asp Leu Asn Thr Met Leu Asn Thr Val Gly
            260                 265                 270
```

```
Gly His Gln Ala Ala Met Gln Met Leu Lys Glu Thr Ile Asn Glu Glu
            275                 280                 285

Ala Ala Glu Trp Asp Arg Val His Pro Val His Ala Gly Pro Ile Ala
        290                 295                 300

Pro Gly Gln Met Arg Glu Pro Arg Gly Ser Asp Ile Ala Gly Thr Thr
305                 310                 315                 320

Ser Thr Leu Gln Glu Gln Ile Gly Trp Met Thr Asn Asn Pro Pro Ile
                325                 330                 335

Pro Val Gly Glu Ile Tyr Lys Arg Trp Ile Ile Leu Gly Leu Asn Lys
            340                 345                 350

Ile Val Arg Met Tyr Ser Pro Thr Ser Ile Leu Asp Ile Arg Gln Gly
        355                 360                 365

Pro Lys Glu Pro Phe Arg Asp Tyr Val Asp Arg Phe Tyr Lys Thr Leu
370                 375                 380

Arg Ala Glu Gln Ala Ser Gln Glu Val Lys Asn Trp Met Thr Glu Thr
385                 390                 395                 400

Leu Leu Val Gln Asn Ala Asn Pro Asp Cys Lys Thr Ile Leu Lys Ala
                405                 410                 415

Leu Gly Pro Ala Ala Thr Leu Glu Glu Met Met Thr Ala Cys Gln Gly
            420                 425                 430

Val Gly Gly Pro Gly His Lys Ala Arg Val Leu Ala Glu Ala Met Ser
        435                 440                 445

Gln Val Thr Asn Ser Ala Thr Ile Met Met Gln Arg Gly Asn Phe Arg
    450                 455                 460

Asn Gln Arg Lys Ile Val Lys Cys Phe Asn Cys Gly Lys Glu Gly His
465                 470                 475                 480

Thr Ala Arg Asn Cys Arg Ala Pro Arg Lys Lys Gly Cys Trp Lys Cys
                485                 490                 495

Gly Lys Glu Gly His Gln Met Lys Asp Cys Thr Glu Arg His Ala Asn
            500                 505                 510

<210> SEQ ID NO 9
<211> LENGTH: 512
<212> TYPE: PRT
<213> ORGANISM: Human immunodeficiency virus

<400> SEQUENCE: 9

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140
```

Gln Ala Ile Ser Pro Arg Thr Leu Asn Ala Trp Val Lys Val Glu
145                 150                 155                 160

Glu Lys Ala Phe Ser Pro Glu Val Ile Pro Met Phe Ser Ala Leu Ser
            165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
            195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
            245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
            290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
            405                 410                 415

Gly Lys Glu Gly His Gln Met Lys Asp Cys Thr Glu Arg His Ala Asn
            420                 425                 430

Lys Glu Ala Leu Leu Ala Thr Gly Ala Asp Asp Thr Val Leu Glu Glu
            435                 440                 445

Met Ser Leu Pro Gly Arg Trp Lys Pro Lys Met Ile Gly Gly Ile Gly
            450                 455                 460

Gly Phe Ile Lys Val Arg Gln Tyr Asp Gln Ile Leu Ile Glu Ile Cys
465                 470                 475                 480

Gly His Lys Ala Ile Gly Thr Val Leu Val Gly Pro Thr Pro Val Asn
            485                 490                 495

Ile Ile Gly Arg Asn Leu Leu Thr Gln Ile Gly Cys Thr Leu Asn Phe
            500                 505                 510

<210> SEQ ID NO 10
<211> LENGTH: 604
<212> TYPE: PRT
<213> ORGANISM: Human immunodeficiency virus

<400> SEQUENCE: 10

Pro Ile Ser Pro Ile Glu Thr Val Pro Val Lys Leu Lys Pro Gly Met

-continued

```
1               5                   10                  15
Asp Gly Pro Lys Val Lys Gln Trp Pro Leu Thr Glu Lys Ile Lys
                20                  25                  30

Ala Leu Val Glu Ile Cys Thr Glu Met Glu Lys Glu Gly Lys Ile Ser
                35                  40                  45

Lys Ile Gly Pro Glu Asn Pro Tyr Asn Thr Pro Val Phe Ala Ile Lys
            50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Ala Val Gly
                100                 105                 110

Asp Ala Tyr Phe Ser Val Pro Leu Asp Glu Asp Phe Arg Lys Tyr Thr
                115                 120                 125

Ala Phe Thr Ile Pro Ser Ile Asn Asn Glu Thr Pro Gly Ile Arg Tyr
            130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Met Gly Ala Arg
                165                 170                 175

Ala Ser Val Leu Ser Gly Gly Glu Leu Asp Arg Trp Glu Lys Ile Arg
                180                 185                 190

Leu Arg Pro Gly Gly Lys Lys Lys Tyr Lys Leu Lys His Ile Val Trp
            195                 200                 205

Ala Ser Arg Glu Leu Glu Arg Phe Ala Val Asn Pro Gly Leu Leu Glu
                210                 215                 220

Thr Ser Glu Gly Cys Arg Gln Ile Leu Gly Gln Leu Gln Pro Ser Leu
225                 230                 235                 240

Gln Thr Gly Ser Glu Glu Leu Arg Ser Leu Tyr Asn Thr Val Ala Thr
                245                 250                 255

Leu Tyr Cys Val His Gln Arg Ile Glu Ile Lys Asp Thr Lys Glu Ala
                260                 265                 270

Leu Asp Lys Ile Glu Glu Glu Gln Asn Lys Ser Lys Lys Lys Ala Gln
            275                 280                 285

Gln Ala Ala Ala Asp Thr Gly His Ser Asn Gln Val Ser Gln Asn Tyr
290                 295                 300

Pro Ile Val Gln Asn Ile Gln Gly Gln Met Val His Gln Ala Ile Ser
305                 310                 315                 320

Pro Arg Thr Leu Asn Ala Trp Val Lys Val Val Glu Glu Lys Ala Phe
                325                 330                 335

Ser Pro Glu Val Ile Pro Met Phe Ser Ala Leu Ser Glu Gly Ala Thr
                340                 345                 350

Pro Gln Asp Leu Asn Thr Met Leu Asn Thr Val Gly Gly His Gln Ala
            355                 360                 365

Ala Met Gln Met Leu Lys Glu Thr Ile Asn Glu Glu Ala Ala Glu Trp
370                 375                 380

Asp Arg Val His Pro Val His Ala Gly Pro Ile Ala Pro Gly Gln Met
385                 390                 395                 400

Arg Glu Pro Arg Gly Ser Asp Ile Ala Gly Thr Thr Ser Thr Leu Gln
                405                 410                 415

Glu Gln Ile Gly Trp Met Thr Asn Asn Pro Pro Ile Pro Val Gly Glu
            420                 425                 430
```

```
Ile Tyr Lys Arg Trp Ile Ile Leu Gly Leu Asn Lys Ile Val Arg Met
            435                 440                 445

Tyr Ser Pro Thr Ser Ile Leu Asp Ile Arg Gln Gly Pro Lys Glu Pro
450                 455                 460

Phe Arg Asp Tyr Val Asp Arg Phe Tyr Lys Thr Leu Arg Ala Glu Gln
465                 470                 475                 480

Ala Ser Gln Glu Val Lys Asn Trp Met Thr Glu Thr Leu Leu Val Gln
                485                 490                 495

Asn Ala Asn Pro Asp Cys Lys Thr Ile Leu Lys Ala Leu Gly Pro Ala
            500                 505                 510

Ala Thr Leu Glu Glu Met Met Thr Ala Cys Gln Gly Val Gly Gly Pro
        515                 520                 525

Gly His Lys Ala Arg Val Leu Ala Glu Ala Met Ser Gln Val Thr Asn
    530                 535                 540

Ser Ala Thr Ile Met Met Gln Arg Gly Asn Phe Arg Asn Gln Arg Lys
545                 550                 555                 560

Ile Val Lys Cys Phe Asn Cys Gly Lys Glu Gly His Thr Ala Arg Asn
                565                 570                 575

Cys Arg Ala Pro Arg Lys Lys Gly Cys Trp Lys Cys Gly Lys Glu Gly
            580                 585                 590

His Gln Met Lys Asp Cys Thr Glu Arg His Ala Asn
        595                 600

<210> SEQ ID NO 11
<211> LENGTH: 604
<212> TYPE: PRT
<213> ORGANISM: Human immunodeficiency virus

<400> SEQUENCE: 11

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
```

```
            195                 200                 205
Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg His Ala Asn
            420                 425                 430

Pro Ile Ser Pro Ile Glu Thr Val Pro Val Lys Leu Lys Pro Gly Met
        435                 440                 445

Asp Gly Pro Lys Val Lys Gln Trp Pro Leu Thr Glu Glu Lys Ile Lys
450                 455                 460

Ala Leu Val Glu Ile Cys Thr Glu Met Glu Lys Glu Gly Lys Ile Ser
465                 470                 475                 480

Lys Ile Gly Pro Glu Asn Pro Tyr Asn Thr Pro Val Phe Ala Ile Lys
                485                 490                 495

Lys Lys Asp Ser Thr Lys Trp Arg Lys Leu Val Asp Phe Arg Glu Leu
            500                 505                 510

Asn Lys Arg Thr Gln Asp Phe Trp Glu Val Gln Leu Gly Ile Pro His
        515                 520                 525

Pro Ala Gly Leu Lys Lys Lys Ser Val Thr Val Leu Ala Val Gly
530                 535                 540

Asp Ala Tyr Phe Ser Val Pro Leu Asp Glu Asp Phe Arg Lys Tyr Thr
545                 550                 555                 560

Ala Phe Thr Ile Pro Ser Ile Asn Asn Glu Thr Pro Gly Ile Arg Tyr
                565                 570                 575

Gln Tyr Asn Val Leu Pro Gln Gly Trp Lys Gly Ser Pro Ala Ile Phe
            580                 585                 590

Gln Ser Ser Met Thr Lys Ile Leu Glu Pro Phe Arg
        595                 600
```

<210> SEQ ID NO 12

<211> LENGTH: 554
<212> TYPE: PRT
<213> ORGANISM: Human immunodeficiency virus

<400> SEQUENCE: 12

```
Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Met Gly Ala Arg Ala Ser
        115                 120                 125

Val Leu Ser Gly Gly Glu Leu Asp Arg Trp Glu Lys Ile Arg Leu Arg
    130                 135                 140

Pro Gly Gly Lys Lys Lys Tyr Lys Leu Lys His Ile Val Trp Ala Ser
145                 150                 155                 160

Arg Glu Leu Glu Arg Phe Ala Val Asn Pro Gly Leu Leu Glu Thr Ser
                165                 170                 175

Glu Gly Cys Arg Gln Ile Leu Gly Gln Leu Gln Pro Ser Leu Gln Thr
            180                 185                 190

Gly Ser Glu Glu Leu Arg Ser Leu Tyr Asn Thr Val Ala Thr Leu Tyr
        195                 200                 205

Cys Val His Gln Arg Ile Glu Ile Lys Asp Thr Lys Glu Ala Leu Asp
    210                 215                 220

Lys Ile Glu Glu Glu Gln Asn Lys Ser Lys Lys Ala Gln Gln Ala
225                 230                 235                 240

Ala Ala Asp Thr Gly His Ser Asn Gln Val Ser Gln Asn Tyr Pro Ile
                245                 250                 255

Val Gln Asn Ile Gln Gly Gln Met Val His Gln Ala Ile Ser Pro Arg
            260                 265                 270

Thr Leu Asn Ala Trp Val Lys Val Val Glu Glu Lys Ala Phe Ser Pro
        275                 280                 285

Glu Val Ile Pro Met Phe Ser Ala Leu Ser Glu Gly Ala Thr Pro Gln
    290                 295                 300

Asp Leu Asn Thr Met Leu Asn Thr Val Gly Gly His Gln Ala Ala Met
305                 310                 315                 320

Gln Met Leu Lys Glu Thr Ile Asn Glu Glu Ala Ala Glu Trp Asp Arg
                325                 330                 335

Val His Pro Val His Ala Gly Pro Ile Ala Pro Gly Gln Met Arg Glu
            340                 345                 350

Pro Arg Gly Ser Asp Ile Ala Gly Thr Thr Ser Thr Leu Gln Glu Gln
        355                 360                 365

Ile Gly Trp Met Thr Asn Asn Pro Pro Ile Pro Val Gly Glu Ile Tyr
    370                 375                 380

Lys Arg Trp Ile Ile Leu Gly Leu Asn Lys Ile Val Arg Met Tyr Ser
```

```
385                 390                 395                 400
Pro Thr Ser Ile Leu Asp Ile Arg Gln Gly Pro Lys Glu Pro Phe Arg
                405                 410                 415

Asp Tyr Val Asp Arg Phe Tyr Lys Thr Leu Arg Ala Glu Gln Ala Ser
            420                 425                 430

Gln Glu Val Lys Asn Trp Met Thr Glu Thr Leu Leu Val Gln Asn Ala
                435                 440                 445

Asn Pro Asp Cys Lys Thr Ile Leu Lys Ala Leu Gly Pro Ala Ala Thr
            450                 455                 460

Leu Glu Glu Met Met Thr Ala Cys Gln Gly Val Gly Gly Pro Gly His
465                 470                 475                 480

Lys Ala Arg Val Leu Ala Glu Ala Met Ser Gln Val Thr Asn Ser Ala
                485                 490                 495

Thr Ile Met Met Gln Arg Gly Asn Phe Arg Asn Gln Arg Lys Ile Val
                500                 505                 510

Lys Cys Phe Asn Cys Gly Lys Glu Gly His Thr Ala Arg Asn Cys Arg
            515                 520                 525

Ala Pro Arg Lys Lys Gly Cys Trp Lys Cys Gly Lys Glu Gly His Gln
        530                 535                 540

Met Lys Asp Cys Thr Glu Arg His Ala Asn
545                 550

<210> SEQ ID NO 13
<211> LENGTH: 554
<212> TYPE: PRT
<213> ORGANISM: Human immunodeficiency virus

<400> SEQUENCE: 13

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205
```

```
Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Thr Ser Ile Leu Asp Ile Arg Gln Gly
                275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
                355                 360                 365

Gln Val Thr Asn Ser Ala Thr Ile Met Met Gln Arg Gly Asn Phe Arg
370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg His Ala Asn
                420                 425                 430

Phe Leu Asp Gly Ile Asp Lys Ala Gln Asp Glu His Glu Lys Tyr His
                435                 440                 445

Ser Asn Trp Arg Ala Met Ala Ser Asp Phe Asn Leu Pro Pro Val Val
                450                 455                 460

Ala Lys Glu Ile Val Ala Ser Cys Asp Lys Cys Gln Leu Lys Gly Glu
465                 470                 475                 480

Ala Met His Gly Gln Val Asp Cys Ser Pro Gly Ile Trp Gln Leu Asp
                485                 490                 495

Cys Thr His Leu Glu Gly Lys Val Ile Leu Val Ala Val His Val Ala
                500                 505                 510

Ser Gly Tyr Ile Glu Ala Glu Val Ile Pro Ala Glu Thr Gly Gln Glu
                515                 520                 525

Thr Ala Tyr Phe Leu Leu Lys Leu Ala Gly Arg Trp Pro Val Lys Thr
                530                 535                 540

Ile His Thr Asp Asn Gly Ser Asn Phe Thr
545                 550

<210> SEQ ID NO 14
<211> LENGTH: 11
<212> TYPE: PRT
<213> ORGANISM: Artificial
<220> FEATURE:
<223> OTHER INFORMATION: synthetic peptide

<400> SEQUENCE: 14

Lys Ala Leu Ser Pro Glu Val Ile Pro Met Val
1               5                   10
```

<210> SEQ ID NO 15
<211> LENGTH: 11
<212> TYPE: PRT
<213> ORGANISM: Artificial
<220> FEATURE:
<223> OTHER INFORMATION: synthetic peptid

<400> SEQUENCE: 15

Lys Ala Met Ser Pro Glu Val Ile Pro Met Val
1               5                   10

<210> SEQ ID NO 16
<211> LENGTH: 11
<212> TYPE: PRT
<213> ORGANISM: Artificial
<220> FEATURE:
<223> OTHER INFORMATION: synthetic peptide

<400> SEQUENCE: 16

Lys Ala Val Ser Pro Glu Val Ile Pro Met Val
1               5                   10

<210> SEQ ID NO 17
<211> LENGTH: 11
<212> TYPE: PRT
<213> ORGANISM: Artificial
<220> FEATURE:
<223> OTHER INFORMATION: synthetic peptide

<400> SEQUENCE: 17

Lys Ala Leu Ser Pro Glu Val Ile Pro Met Ile
1               5                   10

<210> SEQ ID NO 18
<211> LENGTH: 11
<212> TYPE: PRT
<213> ORGANISM: Artificial
<220> FEATURE:
<223> OTHER INFORMATION: synthetic peptide

<400> SEQUENCE: 18

Lys Ala Met Ser Pro Glu Val Ile Pro Met Ile
1               5                   10

<210> SEQ ID NO 19
<211> LENGTH: 11
<212> TYPE: PRT
<213> ORGANISM: Artificial
<220> FEATURE:
<223> OTHER INFORMATION: synthetic peptide

<400> SEQUENCE: 19

Lys Ala Val Ser Pro Glu Val Ile Pro Met Ile
1               5                   10

<210> SEQ ID NO 20
<211> LENGTH: 10
<212> TYPE: PRT
<213> ORGANISM: Artificial
<220> FEATURE:
<223> OTHER INFORMATION: synthetic peptide

<400> SEQUENCE: 20

Thr Ser Leu Leu Gln Glu Gln Ile Gly Val
1               5                   10

```
<210> SEQ ID NO 21
<211> LENGTH: 10
<212> TYPE: PRT
<213> ORGANISM: Artificial
<220> FEATURE:
<223> OTHER INFORMATION: synthetic peptide

<400> SEQUENCE: 21

Thr Ser Met Leu Gln Glu Gln Ile Gly Val
1               5                   10

<210> SEQ ID NO 22
<211> LENGTH: 10
<212> TYPE: PRT
<213> ORGANISM: Artificial
<220> FEATURE:
<223> OTHER INFORMATION: synthetic peptide

<400> SEQUENCE: 22

Thr Ser Val Leu Gln Glu Gln Ile Gly Val
1               5                   10

<210> SEQ ID NO 23
<211> LENGTH: 10
<212> TYPE: PRT
<213> ORGANISM: Artificial
<220> FEATURE:
<223> OTHER INFORMATION: synthetic peptide

<400> SEQUENCE: 23

Thr Ser Leu Leu Gln Glu Gln Ile Gly Ile
1               5                   10

<210> SEQ ID NO 24
<211> LENGTH: 10
<212> TYPE: PRT
<213> ORGANISM: Artificial
<220> FEATURE:
<223> OTHER INFORMATION: synthetic peptide

<400> SEQUENCE: 24

Thr Ser Met Leu Gln Glu Gln Ile Gly Ile
1               5                   10

<210> SEQ ID NO 25
<211> LENGTH: 10
<212> TYPE: PRT
<213> ORGANISM: Artificial
<220> FEATURE:
<223> OTHER INFORMATION: synthetic peptide

<400> SEQUENCE: 25

Thr Ser Val Leu Gln Glu Gln Ile Gly Ile
1               5                   10

<210> SEQ ID NO 26
<211> LENGTH: 10
<212> TYPE: PRT
<213> ORGANISM: Artificial
<220> FEATURE:
<223> OTHER INFORMATION: synthetic peptide

<400> SEQUENCE: 26

Lys Arg Leu Ile Ile Leu Gly Leu Asn Val
1               5                   10

<210> SEQ ID NO 27
```

```
<211> LENGTH: 10
<212> TYPE: PRT
<213> ORGANISM: Artificial
<220> FEATURE:
<223> OTHER INFORMATION: synthetic peptide

<400> SEQUENCE: 27

Lys Arg Met Ile Ile Leu Gly Leu Asn Val
1               5                   10

<210> SEQ ID NO 28
<211> LENGTH: 10
<212> TYPE: PRT
<213> ORGANISM: Artificial
<220> FEATURE:
<223> OTHER INFORMATION: synthetic peptide

<400> SEQUENCE: 28

Lys Arg Val Ile Ile Leu Gly Leu Asn Val
1               5                   10

<210> SEQ ID NO 29
<211> LENGTH: 10
<212> TYPE: PRT
<213> ORGANISM: Artificial
<220> FEATURE:
<223> OTHER INFORMATION: synthetic peptide

<400> SEQUENCE: 29

Lys Arg Leu Ile Ile Leu Gly Leu Asn Ile
1               5                   10

<210> SEQ ID NO 30
<211> LENGTH: 10
<212> TYPE: PRT
<213> ORGANISM: Artificial
<220> FEATURE:
<223> OTHER INFORMATION: synthetic peptide

<400> SEQUENCE: 30

Lys Arg Met Ile Ile Leu Gly Leu Asn Ile
1               5                   10

<210> SEQ ID NO 31
<211> LENGTH: 10
<212> TYPE: PRT
<213> ORGANISM: Artificial
<220> FEATURE:
<223> OTHER INFORMATION: synthetic peptide

<400> SEQUENCE: 31

Lys Arg Val Ile Ile Leu Gly Leu Asn Ile
1               5                   10

<210> SEQ ID NO 32
<211> LENGTH: 9
<212> TYPE: PRT
<213> ORGANISM: Artificial
<220> FEATURE:
<223> OTHER INFORMATION: synthetic peptide

<400> SEQUENCE: 32

Asp Leu Phe Tyr Lys Thr Leu Arg Val
1               5

<210> SEQ ID NO 33
<211> LENGTH: 9
```

```
<212> TYPE: PRT
<213> ORGANISM: Artificial
<220> FEATURE:
<223> OTHER INFORMATION: synthetic peptide

<400> SEQUENCE: 33

Asp Met Phe Tyr Lys Thr Leu Arg Val
1               5

<210> SEQ ID NO 34
<211> LENGTH: 9
<212> TYPE: PRT
<213> ORGANISM: Artificial
<220> FEATURE:
<223> OTHER INFORMATION: synthetic peptide

<400> SEQUENCE: 34

Asp Val Phe Tyr Lys Thr Leu Arg Val
1               5

<210> SEQ ID NO 35
<211> LENGTH: 9
<212> TYPE: PRT
<213> ORGANISM: Artificial
<220> FEATURE:
<223> OTHER INFORMATION: synthetic peptide

<400> SEQUENCE: 35

Asp Leu Phe Tyr Lys Thr Leu Arg Val
1               5

<210> SEQ ID NO 36
<211> LENGTH: 9
<212> TYPE: PRT
<213> ORGANISM: Artificial
<220> FEATURE:
<223> OTHER INFORMATION: synthetic peptide

<400> SEQUENCE: 36

Asp Met Phe Tyr Lys Thr Leu Arg Ile
1               5

<210> SEQ ID NO 37
<211> LENGTH: 9
<212> TYPE: PRT
<213> ORGANISM: Artificial
<220> FEATURE:
<223> OTHER INFORMATION: synthetic peptide

<400> SEQUENCE: 37

Asp Val Phe Tyr Lys Thr Leu Arg Ile
1               5

<210> SEQ ID NO 38
<211> LENGTH: 11
<212> TYPE: PRT
<213> ORGANISM: Artificial
<220> FEATURE:
<223> OTHER INFORMATION: synthetic peptide

<400> SEQUENCE: 38

Tyr Val Asp Leu Phe Tyr Lys Thr Leu Arg Val
1               5                   10

<210> SEQ ID NO 39
<211> LENGTH: 11
<212> TYPE: PRT
```

```
<213> ORGANISM: Artificial
<220> FEATURE:
<223> OTHER INFORMATION: synthetic peptide

<400> SEQUENCE: 39

Tyr Val Asp Met Phe Tyr Lys Thr Leu Arg Val
1               5                   10

<210> SEQ ID NO 40
<211> LENGTH: 11
<212> TYPE: PRT
<213> ORGANISM: Artificial
<220> FEATURE:
<223> OTHER INFORMATION: synthetic peptide

<400> SEQUENCE: 40

Tyr Val Asp Val Phe Tyr Lys Thr Leu Arg Val
1               5                   10

<210> SEQ ID NO 41
<211> LENGTH: 11
<212> TYPE: PRT
<213> ORGANISM: Artificial
<220> FEATURE:
<223> OTHER INFORMATION: synthetic peptide

<400> SEQUENCE: 41

Tyr Val Asp Leu Phe Tyr Lys Thr Leu Arg Ile
1               5                   10

<210> SEQ ID NO 42
<211> LENGTH: 11
<212> TYPE: PRT
<213> ORGANISM: Artificial
<220> FEATURE:
<223> OTHER INFORMATION: synthetic peptide

<400> SEQUENCE: 42

Tyr Val Asp Met Phe Tyr Lys Thr Leu Arg Ile
1               5                   10

<210> SEQ ID NO 43
<211> LENGTH: 11
<212> TYPE: PRT
<213> ORGANISM: Artificial
<220> FEATURE:
<223> OTHER INFORMATION: synthetic peptide

<400> SEQUENCE: 43

Tyr Val Asp Val Phe Tyr Lys Thr Leu Arg Ile
1               5                   10

<210> SEQ ID NO 44
<211> LENGTH: 11
<212> TYPE: PRT
<213> ORGANISM: Artificial
<220> FEATURE:
<223> OTHER INFORMATION: synthetic peptide

<400> SEQUENCE: 44

Lys Ala Phe Ser Pro Glu Leu Ile Pro Met Phe
1               5                   10

<210> SEQ ID NO 45
<211> LENGTH: 11
<212> TYPE: PRT
<213> ORGANISM: Artificial
```

<220> FEATURE:
<223> OTHER INFORMATION: synthetic peptide

<400> SEQUENCE: 45

Lys Ala Phe Ser Pro Glu Ala Ile Pro Met Phe
1               5                   10

<210> SEQ ID NO 46
<211> LENGTH: 11
<212> TYPE: PRT
<213> ORGANISM: Artificial
<220> FEATURE:
<223> OTHER INFORMATION: synthetic peptide

<400> SEQUENCE: 46

Lys Ala Phe Ser Pro Glu Val Leu Pro Met Phe
1               5                   10

<210> SEQ ID NO 47
<211> LENGTH: 11
<212> TYPE: PRT
<213> ORGANISM: Artificial
<220> FEATURE:
<223> OTHER INFORMATION: synthetic peptide

<400> SEQUENCE: 47

Lys Ala Phe Thr Pro Glu Val Ile Pro Met Phe
1               5                   10

<210> SEQ ID NO 48
<211> LENGTH: 11
<212> TYPE: PRT
<213> ORGANISM: Artificial
<220> FEATURE:
<223> OTHER INFORMATION: synthetic peptide

<400> SEQUENCE: 48

Lys Ala Phe Ser Pro Gln Val Ile Pro Met Phe
1               5                   10

<210> SEQ ID NO 49
<211> LENGTH: 11
<212> TYPE: PRT
<213> ORGANISM: Artificial
<220> FEATURE:
<223> OTHER INFORMATION: synthetic peptide

<400> SEQUENCE: 49

Lys Ala Phe Ser Pro Asp Val Ile Pro Met Phe
1               5                   10

<210> SEQ ID NO 50
<211> LENGTH: 10
<212> TYPE: PRT
<213> ORGANISM: Artificial
<220> FEATURE:
<223> OTHER INFORMATION: synthetic peptide

<400> SEQUENCE: 50

Thr Ser Thr Leu Asn Glu Gln Ile Gly Trp
1               5                   10

<210> SEQ ID NO 51
<211> LENGTH: 10
<212> TYPE: PRT
<213> ORGANISM: Artificial
<220> FEATURE:

<223> OTHER INFORMATION: synthetic peptide

<400> SEQUENCE: 51

Thr Ser Thr Leu Gln Glu Asn Ile Gly Trp
1               5                   10

<210> SEQ ID NO 52
<211> LENGTH: 10
<212> TYPE: PRT
<213> ORGANISM: Artificial
<220> FEATURE:
<223> OTHER INFORMATION: synthetic peptide

<400> SEQUENCE: 52

Thr Ser Thr Leu Glu Glu Gln Ile Gly Trp
1               5                   10

<210> SEQ ID NO 53
<211> LENGTH: 10
<212> TYPE: PRT
<213> ORGANISM: Artificial
<220> FEATURE:
<223> OTHER INFORMATION: synthetic peptide

<400> SEQUENCE: 53

Thr Ser Thr Leu Gln Glu Glu Ile Gly Trp
1               5                   10

<210> SEQ ID NO 54
<211> LENGTH: 10
<212> TYPE: PRT
<213> ORGANISM: Artificial
<220> FEATURE:
<223> OTHER INFORMATION: synthetic peptide

<400> SEQUENCE: 54

Thr Ser Thr Leu Gln Gln Gln Ile Gly Trp
1               5                   10

<210> SEQ ID NO 55
<211> LENGTH: 10
<212> TYPE: PRT
<213> ORGANISM: Artificial
<220> FEATURE:
<223> OTHER INFORMATION: synthetic peptide

<400> SEQUENCE: 55

Thr Ser Thr Leu Gln Asp Gln Ile Gly Trp
1               5                   10

<210> SEQ ID NO 56
<211> LENGTH: 10
<212> TYPE: PRT
<213> ORGANISM: Artificial
<220> FEATURE:
<223> OTHER INFORMATION: synthetic peptide

<400> SEQUENCE: 56

Lys Arg Trp Leu Ile Leu Gly Leu Asn Lys
1               5                   10

<210> SEQ ID NO 57
<211> LENGTH: 10
<212> TYPE: PRT
<213> ORGANISM: Artificial
<220> FEATURE:
<223> OTHER INFORMATION: synthetic peptide

```
<400> SEQUENCE: 57

Lys Arg Trp Ile Leu Leu Gly Leu Asn Lys
1               5                   10

<210> SEQ ID NO 58
<211> LENGTH: 10
<212> TYPE: PRT
<213> ORGANISM: Artificial
<220> FEATURE:
<223> OTHER INFORMATION: synthetic peptide

<400> SEQUENCE: 58

Lys Arg Trp Ile Ile Ile Gly Leu Asn Lys
1               5                   10

<210> SEQ ID NO 59
<211> LENGTH: 10
<212> TYPE: PRT
<213> ORGANISM: Artificial
<220> FEATURE:
<223> OTHER INFORMATION: synthetic peptide

<400> SEQUENCE: 59

Lys Arg Trp Ile Ile Leu Ala Leu Asn Lys
1               5                   10

<210> SEQ ID NO 60
<211> LENGTH: 10
<212> TYPE: PRT
<213> ORGANISM: Artificial
<220> FEATURE:
<223> OTHER INFORMATION: synthetic peptide

<400> SEQUENCE: 60

Lys Arg Trp Ile Ile Leu Gly Ile Asn Lys
1               5                   10

<210> SEQ ID NO 61
<211> LENGTH: 10
<212> TYPE: PRT
<213> ORGANISM: Artificial
<220> FEATURE:
<223> OTHER INFORMATION: synthetic peptide

<400> SEQUENCE: 61

Lys Arg Trp Ile Ile Leu Gly Val Asn Lys
1               5                   10

<210> SEQ ID NO 62
<211> LENGTH: 9
<212> TYPE: PRT
<213> ORGANISM: Artificial
<220> FEATURE:
<223> OTHER INFORMATION: synthetic peptide

<400> SEQUENCE: 62

Asp Arg Phe Tyr Arg Thr Leu Arg Ala
1               5

<210> SEQ ID NO 63
<211> LENGTH: 9
<212> TYPE: PRT
<213> ORGANISM: Artificial
<220> FEATURE:
<223> OTHER INFORMATION: synthetic peptide
```

```
<400> SEQUENCE: 63

Asp Arg Phe Tyr Met Thr Leu Arg Ala
1               5

<210> SEQ ID NO 64
<211> LENGTH: 9
<212> TYPE: PRT
<213> ORGANISM: Artificial
<220> FEATURE:
<223> OTHER INFORMATION: synthetic peptide

<400> SEQUENCE: 64

Asp Arg Phe Tyr Lys Ser Leu Arg Ala
1               5

<210> SEQ ID NO 65
<211> LENGTH: 9
<212> TYPE: PRT
<213> ORGANISM: Artificial
<220> FEATURE:
<223> OTHER INFORMATION: synthetic peptide

<400> SEQUENCE: 65

Asp Arg Phe Tyr Lys Thr Ile Arg Ala
1               5

<210> SEQ ID NO 66
<211> LENGTH: 9
<212> TYPE: PRT
<213> ORGANISM: Artificial
<220> FEATURE:
<223> OTHER INFORMATION: synthetic peptide

<400> SEQUENCE: 66

Asp Arg Phe Tyr Lys Thr Val Arg Ala
1               5

<210> SEQ ID NO 67
<211> LENGTH: 9
<212> TYPE: PRT
<213> ORGANISM: Artificial
<220> FEATURE:
<223> OTHER INFORMATION: synthetic peptide

<400> SEQUENCE: 67

Asp Arg Phe Tyr Lys Thr Ala Arg Ala
1               5

<210> SEQ ID NO 68
<211> LENGTH: 11
<212> TYPE: PRT
<213> ORGANISM: Artificial
<220> FEATURE:
<223> OTHER INFORMATION: synthetic peptide

<400> SEQUENCE: 68

Tyr Val Asp Arg Phe Tyr Arg Thr Leu Arg Ala
1               5                   10

<210> SEQ ID NO 69
<211> LENGTH: 11
<212> TYPE: PRT
<213> ORGANISM: Artificial
<220> FEATURE:
<223> OTHER INFORMATION: synthetic peptide

<400> SEQUENCE: 69
```

Tyr Val Asp Arg Phe Tyr Met Thr Leu Arg Ala
1               5                   10

<210> SEQ ID NO 70
<211> LENGTH: 11
<212> TYPE: PRT
<213> ORGANISM: Artificial
<220> FEATURE:
<223> OTHER INFORMATION: synthetic peptide

<400> SEQUENCE: 70

Tyr Val Asp Arg Phe Tyr Lys Ser Leu Arg Ala
1               5                   10

<210> SEQ ID NO 71
<211> LENGTH: 11
<212> TYPE: PRT
<213> ORGANISM: Artificial
<220> FEATURE:
<223> OTHER INFORMATION: synthetic peptide

<400> SEQUENCE: 71

Tyr Val Asp Arg Phe Tyr Lys Thr Ile Arg Ala
1               5                   10

<210> SEQ ID NO 72
<211> LENGTH: 11
<212> TYPE: PRT
<213> ORGANISM: Artificial
<220> FEATURE:
<223> OTHER INFORMATION: synthetic peptide

<400> SEQUENCE: 72

Tyr Val Asp Arg Phe Tyr Lys Thr Val Arg Ala
1               5                   10

<210> SEQ ID NO 73
<211> LENGTH: 11
<212> TYPE: PRT
<213> ORGANISM: Artificial
<220> FEATURE:
<223> OTHER INFORMATION: synthetic peptide

<400> SEQUENCE: 73

Tyr Val Asp Arg Phe Tyr Lys Thr Ala Arg Ala
1               5                   10

<210> SEQ ID NO 74
<211> LENGTH: 432
<212> TYPE: PRT
<213> ORGANISM: Human immunodeficiency virus

<400> SEQUENCE: 74

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Gln Asn Lys Ser Lys
            100                 105                 110

Lys Lys Ala Gln Gln Ala Ala Ala Asp Thr Gly His Ser Asn Gln Val
            115                 120                 125

Ser Gln Asn Tyr Pro Ile Val Gln Asn Ile Gln Gly Gln Met Val His
        130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
        370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg His Ala Asn
            420                 425                 430

<210> SEQ ID NO 75
<211> LENGTH: 431
<212> TYPE: PRT
<213> ORGANISM: Human immunodeficiency virus

<400> SEQUENCE: 75

Met Ala Arg Ala Ser Val Leu Ser Gly Gly Glu Leu Asp Arg Trp Glu
1               5                   10                  15

Lys Ile Arg Leu Arg Pro Gly Gly Lys Lys Tyr Lys Leu Lys His
            20                  25                  30

```
Ile Val Trp Ala Ser Arg Glu Leu Glu Arg Phe Ala Val Asn Pro Gly
        35                  40                  45
Leu Leu Glu Thr Ser Glu Gly Cys Arg Gln Ile Leu Gly Gln Leu Gln
 50                  55                  60
Pro Ser Leu Gln Thr Gly Ser Glu Glu Leu Arg Ser Leu Tyr Asn Thr
 65                  70                  75                  80
Val Ala Thr Leu Tyr Cys Val His Gln Arg Ile Glu Ile Lys Asp Thr
                 85                  90                  95
Lys Glu Ala Leu Asp Lys Ile Glu Glu Gln Asn Lys Ser Lys Lys
                100                 105                 110
Lys Ala Gln Gln Ala Ala Ala Asp Thr Gly His Ser Asn Gln Val Ser
        115                 120                 125
Gln Asn Tyr Pro Ile Val Gln Asn Ile Gln Gly Gln Met Val His Gln
130                 135                 140
Ala Ile Ser Pro Arg Thr Leu Asn Ala Trp Val Lys Val Val Glu Glu
145                 150                 155                 160
Lys Ala Phe Ser Pro Glu Val Ile Pro Met Phe Ser Ala Leu Ser Glu
                165                 170                 175
Gly Ala Thr Pro Gln Asp Leu Asn Thr Met Leu Asn Thr Val Gly Gly
                180                 185                 190
His Gln Ala Ala Met Gln Met Leu Lys Glu Thr Ile Asn Glu Glu Ala
        195                 200                 205
Ala Glu Trp Asp Arg Val His Pro Val His Ala Gly Pro Ile Ala Pro
210                 215                 220
Gly Gln Met Arg Glu Pro Arg Gly Ser Asp Ile Ala Gly Thr Thr Ser
225                 230                 235                 240
Thr Leu Gln Glu Gln Ile Gly Trp Met Thr Asn Asn Pro Pro Ile Pro
                245                 250                 255
Val Gly Glu Ile Tyr Lys Arg Trp Ile Ile Leu Gly Leu Asn Lys Ile
                260                 265                 270
Val Arg Met Tyr Ser Pro Thr Ser Ile Leu Asp Ile Arg Gln Gly Pro
        275                 280                 285
Lys Glu Pro Phe Arg Asp Tyr Val Asp Arg Phe Tyr Lys Thr Leu Arg
290                 295                 300
Ala Glu Gln Ala Ser Gln Glu Val Lys Asn Trp Met Thr Glu Thr Leu
305                 310                 315                 320
Leu Val Gln Asn Ala Asn Pro Asp Cys Lys Thr Ile Leu Lys Ala Leu
                325                 330                 335
Gly Pro Ala Ala Thr Leu Glu Glu Met Met Thr Ala Cys Gln Gly Val
                340                 345                 350
Gly Gly Pro Gly His Lys Ala Arg Val Leu Ala Glu Ala Met Ser Gln
        355                 360                 365
Val Thr Asn Ser Ala Thr Ile Met Met Gln Arg Gly Asn Phe Arg Asn
370                 375                 380
Gln Arg Lys Ile Val Lys Cys Phe Asn Cys Gly Lys Glu Gly His Thr
385                 390                 395                 400
Ala Arg Asn Cys Arg Ala Pro Arg Lys Lys Gly Cys Trp Lys Cys Gly
                405                 410                 415
Lys Glu Gly His Gln Met Lys Asp Cys Thr Glu Arg His Ala Asn
                420                 425                 430
```

<210> SEQ ID NO 76
<211> LENGTH: 11

```
<212> TYPE: PRT
<213> ORGANISM: Human immunodeficiency virus

<400> SEQUENCE: 76

Lys Ala Phe Ser Pro Glu Val Ile Pro Met Phe
1               5                   10

<210> SEQ ID NO 77
<211> LENGTH: 10
<212> TYPE: PRT
<213> ORGANISM: Human immunodeficiency virus

<400> SEQUENCE: 77

Thr Ser Thr Leu Gln Glu Gln Ile Gly Trp
1               5                   10

<210> SEQ ID NO 78
<211> LENGTH: 10
<212> TYPE: PRT
<213> ORGANISM: Human immunodeficiency virus

<400> SEQUENCE: 78

Lys Arg Trp Ile Ile Leu Gly Leu Asn Lys
1               5                   10

<210> SEQ ID NO 79
<211> LENGTH: 9
<212> TYPE: PRT
<213> ORGANISM: Human immunodeficiency virus

<400> SEQUENCE: 79

Asp Arg Phe Tyr Lys Thr Leu Arg Ala
1               5

<210> SEQ ID NO 80
<211> LENGTH: 11
<212> TYPE: PRT
<213> ORGANISM: Human immunodeficiency virus

<400> SEQUENCE: 80

Tyr Val Asp Arg Phe Tyr Lys Thr Leu Arg Ala
1               5                   10

<210> SEQ ID NO 81
<211> LENGTH: 6
<212> TYPE: PRT
<213> ORGANISM: Artificial
<220> FEATURE:
<223> OTHER INFORMATION: synthetic peptide

<400> SEQUENCE: 81

Met Ala Asp Glu Ala Pro
1               5

<210> SEQ ID NO 82
<211> LENGTH: 89
<212> TYPE: PRT
<213> ORGANISM: Saccharomyces cerevisiae

<400> SEQUENCE: 82

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30
```

```
Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
 65                  70                  75                  80

Ser Leu Asp Lys Arg Glu Ala Glu Ala
                85

<210> SEQ ID NO 83
<211> LENGTH: 89
<212> TYPE: PRT
<213> ORGANISM: Saccharomyces cerevisiae

<400> SEQUENCE: 83

Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
 65                  70                  75                  80

Ser Leu Asp Lys Arg Glu Ala Glu Ala
                85

<210> SEQ ID NO 84
<211> LENGTH: 15
<212> TYPE: PRT
<213> ORGANISM: Human immunodeficiency virus

<400> SEQUENCE: 84

Tyr Val Asp Arg Phe Tyr Lys Thr Leu Arg Ala Glu Gln Ala Ser
  1               5                  10                  15

<210> SEQ ID NO 85
<211> LENGTH: 2003
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(1995)

<400> SEQUENCE: 85 atg aga ttt cct tca att ttt act gca gtt tta ttc gca gca tcc tcc      48
Met Arg Phe Pro Ser Ile Phe Thr Ala Val Leu Phe Ala Ala Ser Ser
  1               5                  10                  15 gca tca gct gct cca gtc aac act aca aca gaa gat gaa acg gca caa      96
Ala Ser Ala Ala Pro Val Asn Thr Thr Thr Glu Asp Glu Thr Ala Gln
             20                  25                  30 att ccg gct gaa gct gtc atc ggt tac tta gat tta gaa ggg gat ttc     144
Ile Pro Ala Glu Ala Val Ile Gly Tyr Leu Asp Leu Glu Gly Asp Phe
            35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
 50                  55                  60 ttt ata aat act act att gcc agc att gct gct aaa gaa gaa ggg gta     240
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Phe | Ile | Asn | Thr | Thr | Ile | Ala | Ser | Ile | Ala | Ala | Lys | Glu | Glu | Gly | Val |      |
| 65  |     |     |     |     | 70  |     |     |     |     | 75  |     |     |     |     | 80  |      |

| tct | cta | gat | aaa | aga | gag | gct | gaa | gct | act | agt | cct | att | gtg | caa | aac | 288 |
| --- | --- | --- | --- | --- | --- | --- | --- | --- | --- | --- | --- | --- | --- | --- | --- | --- |
| Ser | Leu | Asp | Lys | Arg | Glu | Ala | Glu | Ala | Thr | Ser | Pro | Ile | Val | Gln | Asn |     |
|     |     |     |     | 85  |     |     |     |     | 90  |     |     |     |     | 95  |     |     |

| atc | caa | ggt | caa | atg | gtt | cat | cag | gca | att | tct | ccc | aga | aca | ttg | aat | 336 |
| --- | --- | --- | --- | --- | --- | --- | --- | --- | --- | --- | --- | --- | --- | --- | --- | --- |
| Ile | Gln | Gly | Gln | Met | Val | His | Gln | Ala | Ile | Ser | Pro | Arg | Thr | Leu | Asn |     |
|     |     |     | 100 |     |     |     |     | 105 |     |     |     |     | 110 |     |     |     |

| gcg | tgg | gtc | aag | gta | gtt | gag | gaa | aaa | gcc | ttt | tca | cca | gaa | gtc | ata | 384 |
| --- | --- | --- | --- | --- | --- | --- | --- | --- | --- | --- | --- | --- | --- | --- | --- | --- |
| Ala | Trp | Val | Lys | Val | Val | Glu | Glu | Lys | Ala | Phe | Ser | Pro | Glu | Val | Ile |     |
|     |     |     | 115 |     |     |     |     | 120 |     |     |     |     | 125 |     |     |     |

| cca | atg | ttt | tcc | gcc | ttg | tct | gaa | ggc | gcc | aca | cct | caa | gac | ctc | aat | 432 |
| --- | --- | --- | --- | --- | --- | --- | --- | --- | --- | --- | --- | --- | --- | --- | --- | --- |
| Pro | Met | Phe | Ser | Ala | Leu | Ser | Glu | Gly | Ala | Thr | Pro | Gln | Asp | Leu | Asn |     |
|     | 130 |     |     |     |     | 135 |     |     |     |     | 140 |     |     |     |     |     |

| act | atg | ctg | aat | acc | gtg | gga | gga | cat | caa | gcc | gct | atg | caa | atg | tta | 480 |
| --- | --- | --- | --- | --- | --- | --- | --- | --- | --- | --- | --- | --- | --- | --- | --- | --- |
| Thr | Met | Leu | Asn | Thr | Val | Gly | Gly | His | Gln | Ala | Ala | Met | Gln | Met | Leu |     |
| 145 |     |     |     |     | 150 |     |     |     |     | 155 |     |     |     |     | 160 |     |

| aag | gaa | acc | atc | aac | gaa | gag | gcg | gct | gag | tgg | gat | cgt | gtt | cac | cct | 528 |
| --- | --- | --- | --- | --- | --- | --- | --- | --- | --- | --- | --- | --- | --- | --- | --- | --- |
| Lys | Glu | Thr | Ile | Asn | Glu | Glu | Ala | Ala | Glu | Trp | Asp | Arg | Val | His | Pro |     |
|     |     |     |     | 165 |     |     |     |     | 170 |     |     |     |     | 175 |     |     |

| gtc | cat | gca | gga | cct | att | gca | cca | ggt | caa | atg | aga | gaa | cca | aga | gga | 576 |
| --- | --- | --- | --- | --- | --- | --- | --- | --- | --- | --- | --- | --- | --- | --- | --- | --- |
| Val | His | Ala | Gly | Pro | Ile | Ala | Pro | Gly | Gln | Met | Arg | Glu | Pro | Arg | Gly |     |
|     |     | 180 |     |     |     |     | 185 |     |     |     |     | 190 |     |     |     |     |

| tct | gac | att | gcg | ggt | act | aca | agt | aca | ctg | cag | gaa | caa | ata | gga | tgg | 624 |
| --- | --- | --- | --- | --- | --- | --- | --- | --- | --- | --- | --- | --- | --- | --- | --- | --- |
| Ser | Asp | Ile | Ala | Gly | Thr | Thr | Ser | Thr | Leu | Gln | Glu | Gln | Ile | Gly | Trp |     |
|     |     | 195 |     |     |     |     | 200 |     |     |     |     | 205 |     |     |     |     |

| atg | acg | aac | aat | cct | cct | att | cca | gtt | ggt | gag | ata | tac | aag | aga | tgg | 672 |
| --- | --- | --- | --- | --- | --- | --- | --- | --- | --- | --- | --- | --- | --- | --- | --- | --- |
| Met | Thr | Asn | Asn | Pro | Pro | Ile | Pro | Val | Gly | Glu | Ile | Tyr | Lys | Arg | Trp |     |
|     | 210 |     |     |     |     | 215 |     |     |     |     | 220 |     |     |     |     |     |

| atc | att | ctt | ggc | tta | aac | aag | att | gtt | aga | atg | tac | agt | cca | aca | tca | 720 |
| --- | --- | --- | --- | --- | --- | --- | --- | --- | --- | --- | --- | --- | --- | --- | --- | --- |
| Ile | Ile | Leu | Gly | Leu | Asn | Lys | Ile | Val | Arg | Met | Tyr | Ser | Pro | Thr | Ser |     |
| 225 |     |     |     |     | 230 |     |     |     |     | 235 |     |     |     |     | 240 |     |

| atc | cta | gat | atc | aga | cag | ggt | cca | aaa | gag | cct | ttt | aga | gat | tac | gtc | 768 |
| --- | --- | --- | --- | --- | --- | --- | --- | --- | --- | --- | --- | --- | --- | --- | --- | --- |
| Ile | Leu | Asp | Ile | Arg | Gln | Gly | Pro | Lys | Glu | Pro | Phe | Arg | Asp | Tyr | Val |     |
|     |     |     |     | 245 |     |     |     |     | 250 |     |     |     |     | 255 |     |     |

| gat | aga | ttt | tac | aaa | aca | ctt | aga | gca | gaa | caa | gca | tct | caa | gag | gtg | 816 |
| --- | --- | --- | --- | --- | --- | --- | --- | --- | --- | --- | --- | --- | --- | --- | --- | --- |
| Asp | Arg | Phe | Tyr | Lys | Thr | Leu | Arg | Ala | Glu | Gln | Ala | Ser | Gln | Glu | Val |     |
|     |     |     | 260 |     |     |     |     | 265 |     |     |     |     | 270 |     |     |     |

| aaa | aac | tgg | atg | act | gaa | act | ctt | ctg | gtt | caa | aat | gct | aat | cca | gac | 864 |
| --- | --- | --- | --- | --- | --- | --- | --- | --- | --- | --- | --- | --- | --- | --- | --- | --- |
| Lys | Asn | Trp | Met | Thr | Glu | Thr | Leu | Leu | Val | Gln | Asn | Ala | Asn | Pro | Asp |     |
|     |     | 275 |     |     |     |     | 280 |     |     |     |     | 285 |     |     |     |     |

| tgt | aaa | acg | att | ttg | aag | gca | cta | ggc | cct | gca | gct | act | ttg | gaa | gag | 912 |
| --- | --- | --- | --- | --- | --- | --- | --- | --- | --- | --- | --- | --- | --- | --- | --- | --- |
| Cys | Lys | Thr | Ile | Leu | Lys | Ala | Leu | Gly | Pro | Ala | Ala | Thr | Leu | Glu | Glu |     |
|     | 290 |     |     |     |     | 295 |     |     |     |     | 300 |     |     |     |     |     |

| atg | atg | act | gct | tgt | caa | ggg | gta | ggt | ggt | cct | ggt | cac | aaa | gct | aga | 960 |
| --- | --- | --- | --- | --- | --- | --- | --- | --- | --- | --- | --- | --- | --- | --- | --- | --- |
| Met | Met | Thr | Ala | Cys | Gln | Gly | Val | Gly | Gly | Pro | Gly | His | Lys | Ala | Arg |     |
| 305 |     |     |     | 310 |     |     |     |     | 315 |     |     |     |     | 320 |     |     |

| gtg | tta | gca | gaa | gca | atg | tca | caa | gtc | acc | aat | tcc | gcc | aca | att | atg | 1008 |
| --- | --- | --- | --- | --- | --- | --- | --- | --- | --- | --- | --- | --- | --- | --- | --- | ---- |
| Val | Leu | Ala | Glu | Ala | Met | Ser | Gln | Val | Thr | Asn | Ser | Ala | Thr | Ile | Met |      |
|     |     |     |     | 325 |     |     |     |     | 330 |     |     |     |     | 335 |     |      |

| aag | gaa | gct | ctg | tta | gct | act | ggg | gct | gat | gat | aca | gtt | ttg | gag | gaa | 1056 |
| --- | --- | --- | --- | --- | --- | --- | --- | --- | --- | --- | --- | --- | --- | --- | --- | ---- |
| Lys | Glu | Ala | Leu | Leu | Ala | Thr | Gly | Ala | Asp | Asp | Thr | Val | Leu | Glu | Glu |      |
|     |     |     | 340 |     |     |     |     | 345 |     |     |     |     | 350 |     |     |      |

| atg | tct | ttg | cca | ggt | aga | tgg | aag | cca | aaa | atg | atc | ggg | ggc | ata | ggc | 1104 |
| --- | --- | --- | --- | --- | --- | --- | --- | --- | --- | --- | --- | --- | --- | --- | --- | ---- |
| Met | Ser | Leu | Pro | Gly | Arg | Trp | Lys | Pro | Lys | Met | Ile | Gly | Gly | Ile | Gly |      |
|     |     |     | 355 |     |     |     |     | 360 |     |     |     |     | 365 |     |     |      |

| ggc | ttt | atc | aaa | gta | agg | caa | tat | gac | caa | atc | tta | att | gaa | atc | tgt | 1152 |
| --- | --- | --- | --- | --- | --- | --- | --- | --- | --- | --- | --- | --- | --- | --- | --- | ---- |
| Gly | Phe | Ile | Lys | Val | Arg | Gln | Tyr | Asp | Gln | Ile | Leu | Ile | Glu | Ile | Cys |      |
|     | 370 |     |     |     |     | 375 |     |     |     |     | 380 |     |     |     |     |      |

```
ggc cat aag gct atc gga act gtg ttg gta ggc cca aca cct gtt aac    1200
Gly His Lys Ala Ile Gly Thr Val Leu Val Gly Pro Thr Pro Val Asn
385             390                 395                 400 ata att ggt aga aac cta ctt acc caa ata ggg tgt act ttg aat ttc    1248
Ile Ile Gly Arg Asn Leu Leu Thr Gln Ile Gly Cys Thr Leu Asn Phe
        405                 410                 415 tac gtt gat gga gcc gct aat cga gaa acc aaa tta gga aaa gcg ggt    1296
Tyr Val Asp Gly Ala Ala Asn Arg Glu Thr Lys Leu Gly Lys Ala Gly
            420                 425                 430 tac gtt act aat aga ggt agg cag aaa gtc gtt aca ctg aca gat act    1344
Tyr Val Thr Asn Arg Gly Arg Gln Lys Val Val Thr Leu Thr Asp Thr
                435                 440                 445 aca aat caa aag aca gaa tta caa gcc att tac ctt gct ttg caa gat    1392
Thr Asn Gln Lys Thr Glu Leu Gln Ala Ile Tyr Leu Ala Leu Gln Asp
    450                 455                 460 tca ggt ttg gaa gta aac att gtt act gac agt cag tat gct ctt ggt    1440
Ser Gly Leu Glu Val Asn Ile Val Thr Asp Ser Gln Tyr Ala Leu Gly
465                 470                 475                 480 atc atc cag gct caa cca gat caa tcc gaa tca gaa ctc gtt aat cag    1488
Ile Ile Gln Ala Gln Pro Asp Gln Ser Glu Ser Glu Leu Val Asn Gln
                485                 490                 495 att att gaa caa ctc atc aaa aag gag aaa gta tat cta gct tgg gtc    1536
Ile Ile Glu Gln Leu Ile Lys Lys Glu Lys Val Tyr Leu Ala Trp Val
                500                 505                 510 cca gct cac aaa ggt ata gga ggg aat gaa caa gtc gat aag tta gtt    1584
Pro Ala His Lys Gly Ile Gly Gly Asn Glu Gln Val Asp Lys Leu Val
            515                 520                 525 tcc gct ggc atc cgt aaa gtg tta ttc cta gat ggc atc gac aaa gct    1632
Ser Ala Gly Ile Arg Lys Val Leu Phe Leu Asp Gly Ile Asp Lys Ala
530                 535                 540 caa gat gaa cac gag aaa tac cat tct aac tgg aga gca atg gca agc    1680
Gln Asp Glu His Glu Lys Tyr His Ser Asn Trp Arg Ala Met Ala Ser
545                 550                 555                 560 gat ttc aat ctt cca cca gta gtc gca aag gaa atc gta gca tct tgc    1728
Asp Phe Asn Leu Pro Pro Val Val Ala Lys Glu Ile Val Ala Ser Cys
                565                 570                 575 gat aaa tgt caa ttg aaa ggg gaa gcc atg cac ggt cag gtt gat tgc    1776
Asp Lys Cys Gln Leu Lys Gly Glu Ala Met His Gly Gln Val Asp Cys
                580                 585                 590 tct cct ggt ata tgg caa ttg gac tgc acg cat tta gaa ggt aag gtg    1824
Ser Pro Gly Ile Trp Gln Leu Asp Cys Thr His Leu Glu Gly Lys Val
            595                 600                 605 ata ttg gtg gcc gtt cat gta gca tca ggt tat atc gaa gct gaa gtt    1872
Ile Leu Val Ala Val His Val Ala Ser Gly Tyr Ile Glu Ala Glu Val
    610                 615                 620 att cca gca gag aca gga caa gag aca gcc tac ttc cta ttg aag ctc    1920
Ile Pro Ala Glu Thr Gly Gln Glu Thr Ala Tyr Phe Leu Leu Lys Leu
625                 630                 635                 640 gcc gga aga tgg cca gtt aaa act atc cac acc gac aat ggt tct aac    1968
Ala Gly Arg Trp Pro Val Lys Thr Ile His Thr Asp Asn Gly Ser Asn
                645                 650                 655 ttt aca cat cac cat cat cat cat tag gcggccgc                       2003
Phe Thr His His His His His His
                660

<210> SEQ ID NO 86
<211> LENGTH: 664
<212> TYPE: PRT
<213> ORGANISM: Artificial
<220> FEATURE:
<223> OTHER INFORMATION: Synthetic Construct
```

<400> SEQUENCE: 86

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Thr Ser Pro Ile Val Gln Asn
                85                  90                  95

Ile Gln Gly Gln Met Val His Gln Ala Ile Ser Pro Arg Thr Leu Asn
            100                 105                 110

Ala Trp Val Lys Val Val Glu Glu Lys Ala Phe Ser Pro Glu Val Ile
        115                 120                 125

Pro Met Phe Ser Ala Leu Ser Glu Gly Ala Thr Pro Gln Asp Leu Asn
    130                 135                 140

Thr Met Leu Asn Thr Val Gly Gly His Gln Ala Ala Met Gln Met Leu
145                 150                 155                 160

Lys Glu Thr Ile Asn Glu Glu Ala Ala Glu Trp Asp Arg Val His Pro
                165                 170                 175

Val His Ala Gly Pro Ile Ala Pro Gly Gln Met Arg Glu Pro Arg Gly
            180                 185                 190

Ser Asp Ile Ala Gly Thr Thr Ser Thr Leu Gln Glu Gln Ile Gly Trp
        195                 200                 205

Met Thr Asn Asn Pro Pro Ile Pro Val Gly Glu Ile Tyr Lys Arg Trp
    210                 215                 220

Ile Ile Leu Gly Leu Asn Lys Ile Val Arg Met Tyr Ser Pro Thr Ser
225                 230                 235                 240

Ile Leu Asp Ile Arg Gln Gly Pro Lys Glu Pro Phe Arg Asp Tyr Val
                245                 250                 255

Asp Arg Phe Tyr Lys Thr Leu Arg Ala Glu Gln Ala Ser Gln Glu Val
            260                 265                 270

Lys Asn Trp Met Thr Glu Thr Leu Leu Val Gln Asn Ala Asn Pro Asp
        275                 280                 285

Cys Lys Thr Ile Leu Lys Ala Leu Gly Pro Ala Ala Thr Leu Glu Glu
    290                 295                 300

Met Met Thr Ala Cys Gln Gly Val Gly Gly Pro Gly His Lys Ala Arg
305                 310                 315                 320

Val Leu Ala Glu Ala Met Ser Gln Val Thr Asn Ser Ala Thr Ile Met
                325                 330                 335

Lys Glu Ala Leu Leu Ala Thr Gly Ala Asp Asp Thr Val Leu Glu Glu
            340                 345                 350

Met Ser Leu Pro Gly Arg Trp Lys Pro Lys Met Ile Gly Gly Ile Gly
        355                 360                 365

Gly Phe Ile Lys Val Arg Gln Tyr Asp Gln Ile Leu Ile Glu Ile Cys
370                 375                 380

```
Gly His Lys Ala Ile Gly Thr Val Leu Val Gly Pro Thr Pro Val Asn
385                 390                 395                 400

Ile Ile Gly Arg Asn Leu Leu Thr Gln Ile Gly Cys Thr Leu Asn Phe
                405                 410                 415

Tyr Val Asp Gly Ala Ala Asn Arg Glu Thr Lys Leu Gly Lys Ala Gly
            420                 425                 430

Tyr Val Thr Asn Arg Gly Arg Gln Lys Val Val Thr Leu Thr Asp Thr
            435                 440                 445

Thr Asn Gln Lys Thr Glu Leu Gln Ala Ile Tyr Leu Ala Leu Gln Asp
    450                 455                 460

Ser Gly Leu Glu Val Asn Ile Val Thr Asp Ser Gln Tyr Ala Leu Gly
465                 470                 475                 480

Ile Ile Gln Ala Gln Pro Asp Gln Ser Glu Ser Glu Leu Val Asn Gln
                485                 490                 495

Ile Ile Glu Gln Leu Ile Lys Lys Glu Lys Val Tyr Leu Ala Trp Val
            500                 505                 510

Pro Ala His Lys Gly Ile Gly Gly Asn Glu Gln Val Asp Lys Leu Val
        515                 520                 525

Ser Ala Gly Ile Arg Lys Val Leu Phe Leu Asp Gly Ile Asp Lys Ala
530                 535                 540

Gln Asp Glu His Glu Lys Tyr His Ser Asn Trp Arg Ala Met Ala Ser
545                 550                 555                 560

Asp Phe Asn Leu Pro Pro Val Val Ala Lys Glu Ile Val Ala Ser Cys
                565                 570                 575

Asp Lys Cys Gln Leu Lys Gly Glu Ala Met His Gly Gln Val Asp Cys
            580                 585                 590

Ser Pro Gly Ile Trp Gln Leu Asp Cys Thr His Leu Glu Gly Lys Val
        595                 600                 605

Ile Leu Val Ala Val His Val Ala Ser Gly Tyr Ile Glu Ala Glu Val
610                 615                 620

Ile Pro Ala Glu Thr Gly Gln Glu Thr Ala Tyr Phe Leu Leu Lys Leu
625                 630                 635                 640

Ala Gly Arg Trp Pro Val Lys Thr Ile His Thr Asp Asn Gly Ser Asn
                645                 650                 655

Phe Thr His His His His His His
                660
```

COMPOSITIONS AND METHODS FOR THE TREATMENT OR PREVENTION OF HUMAN IMMUNODEFICIENCY VIRUS INFECTION

CROSS-REFERENCE TO RELATED APPLICATIONS

This application is a divisional application of U.S. application Ser. No. 14/780,012, filed Sep. 25, 2015, now U.S. Pat. No. 9,782,473, which is a national stage application under 35 U.S.C. 371 of PCT Application No. PCT/US2014/031811 having an international filing date of Mar 26, 2014, which designated the United States, which PCT application claimed the benefit of priority under 35 U.S.C. § 119(e) to U.S. Provisional Application No. 61/805,299, filed Mar. 26, 2013 and to U.S. Provisional Application No. 61/891,093, filed Oct. 15, 2013. The entire disclosure of each of U.S. Provisional Application No. 61/805,299 and U.S. Provisional Application No. 61/891,093, U.S. application Ser. No. 14/780,012 and PCT Application No. PCT/US2014/031811 are each incorporated herein by reference.

REFERENCE TO A SEQUENCE LISTING

This application contains a Sequence Listing submitted electronically as a text file by EFS-Web. The text file, named "3923-44-PCT_ST25", has a size in bytes of 85 KB, and was recorded on Mar. 19, 2014. The information contained in the text file is incorporated herein by reference in its entirety pursuant to 37 CFR § 1.52(e)(5).

FIELD OF THE INVENTION

The present invention generally relates to immunotherapeutic compositions and methods for preventing and/or treating human immunodeficiency virus (HIV) infection.

BACKGROUND OF THE INVENTION

Human immunodeficiency virus (HIV) infection/Acquired Immunodeficiency Syndrome (HIV/AIDS) is a disease affecting primarily cells of the human immune system caused by infection with HIV. Since its discovery in 1981, AIDS has caused nearly 30 million deaths (as of 2009) ("Global Report Fact Sheet". UNAIDS. 2010) and as of 2010, approximately 34 million people were infected with HIV worldwide (UNAIDS 2011 pg. 1-10). HIV/AIDS is now considered to be a chronic disease, rather than a fatal disease in many parts of the world (Knoll et al., (2007) *Int J Dermatol* 46 (12): 1219-28. While the prognosis of the disease can vary from patient to patient, both a patient's CD4+ T cell count and viral load are useful for predicted outcomes. Without treatment, average survival time after infection with HIV is estimated to be 9 to 11 years, depending on the HIV subtype (UNAIDS, WHO (December 2007). "2007 AIDS epidemic update" (PDF)). After the diagnosis of AIDS, if treatment is not available, survival ranges between 6 and 19 months (Morgan et al., (2002) *AIDS* 16 (4):597-632; Zwahlen and Egger (2006), UNAIDS Obligation HQ/05/422204, archived from the original on Apr. 9, 2008). Highly active antiretroviral therapy (HAART) and appropriate prevention of opportunistic infections reduces the death rate by 80%, and raises the life expectancy for a newly diagnosed young adult to 20-50 years (Knoll et al., supra; Antiretroviral Therapy Cohort Collaboration (2008) *Lancet* 372 (9635): 293-9; Schackman et al., (2006), *Med Care* 44 (11): 990-997).

HAART options are combinations (or "cocktails") consisting of at least three medications belonging to at least two types, or "classes," of antiretroviral agents, which may include non-nucleoside reverse transcriptase inhibitors (NNRTI), nucleoside analogue reverse transcriptase inhibitors (NRTIs), integrase inhibitors and entry inhibitors. Initially treatment is typically a non-nucleoside reverse transcriptase inhibitor (NNRTI) plus two nucleoside analogue reverse transcriptase inhibitors (NRTIs). Typical NRTIs include: zidovudine (AZT) or tenofovir (TDF) and lamivudine (3TC) or emtricitabine (FTC). Combinations of agents which include protease inhibitors (PI) are used if the above regime loses effectiveness.

The current standard of care (SOC) treatments for HIV are generally fixed dose combinations (FDCs), comprised of cross-class drugs provided as a single pill taken once daily. Such FDCs include ATRIPLA® (tenofovir disoproxil fumarate/emtricitabine/efavirenz: tenofovir/NRTI+emtricitabine/NRTI, with efavirenz (a non-nucleoside reverse transcriptase inhibitor (NNRTI) from Bristol Myers-Squibb), Gilead Sciences, Inc.), COMPLERA® (tenofovir disoproxil fumarate/emtricitabine/rilpivirine: tenofovir/NRTI+emtricitabine/NRTI, with rilpivirine (a NNRTI from Tibotec/Johnson & Johnson), Gilead Sciences, Inc.); STRIBILD/QUAD (tenofovir disoproxil fumarate/emtricitabine/elvitegravir/cobicistat: tenofovir/NRTI+emtricitabine/NRTI, with cobicistat-boosted elvitegravir (integrase inhibitor from Japan Tobacco), Gilead Sciences, Inc.); and 572-TRII® (abcavir/NRTI+lamivudine/NRTI, with dolutegravir (integrase inhibitor from Pfizer/Shionogi), ViiV (GlaxoSmithKline, Pfizer, Shionogi).

Combination antiretroviral therapy has made HIV a chronic manageable disease but is not a cure. HIV DNA incorporated into the DNA of latent or inactive T-cells and remains until the cell is activated. Current regimens do not address virus sequestered in latent cells. Moreover, current FDCs and their individual components suffer from side effects and failures, including: central nervous system (CNS) side effects, kidney toxicity, resistance/transmitted resistance, and failure with higher viral loads.

Prior efforts to develop a therapeutic vaccine have met with failure, or results have been difficult to interpret, including efforts using a vaccinia virus based approach, efforts utilizing subunit vaccines (HIV gp160), a whole-killed HIV isolate vaccine, and naked DNA vaccines. Accordingly, there remains a need in the art for compositions and methods to provide a functional cure of HIV infection (i.e., containment of HIV replication and prevention of disease in the absence of ongoing treatment) or a sterilizing cure of HIV infection (i.e., complete elimination of the virus), or to further ameliorate the symptoms of HIV infection or its sequelae, and/or to further enable an infected individual to control the virus and remain healthy.

SUMMARY OF THE INVENTION

One embodiment of the invention relates to an immunotherapeutic composition comprising: (a) a yeast vehicle; and (b) a fusion protein comprising HIV antigens. In one aspect, the HIV antigens wherein the HIV antigens comprise or consist of an amino acid sequence that is at least 80% identical, at least 85% identical, at least 90% identical, at least 95% identical, at least 96% identical, at least 97% identical, at least 98% identical, at least 99% identical, or is identical to an amino acid sequence selected from: SEQ ID NO:5, SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, and/or SEQ ID NO:84, or a corresponding amino acid sequence from a different HIV strain.

In one embodiment of the invention, the HIV antigens consist of the amino acid sequence of SEQ ID NO:5. In one embodiment of the invention, the fusion protein comprises an amino acid sequence of SEQ ID NO:86.

In any embodiment related to an immunotherapeutic composition of the invention, including the embodiments described above, in one aspect, the HIV antigen is expressed by the yeast vehicle.

In any embodiment related to an immunotherapeutic composition of the invention, including the embodiments described above, in one aspect, the yeast vehicle is a whole yeast.

In any embodiment related to an immunotherapeutic composition of the invention, including the embodiments described above, in one aspect, the yeast vehicle is a whole, killed or inactivated yeast.

In any embodiment related to an immunotherapeutic composition of the invention, including the embodiments described above, in one aspect, the yeast vehicle is a whole, heat-inactivated yeast.

In any embodiment related to an immunotherapeutic composition of the invention, including the embodiments described above, in one aspect, the yeast vehicle is a processed yeast (described in detail below).

Another embodiment of the invention relates to an immunotherapeutic composition comprising: (a) a whole, inactivated yeast; and (b) an HIV fusion protein comprising the amino acid sequence of SEQ ID NO:5, wherein the fusion protein is under the control of the promoter CUP1. The HIV fusion protein is expressed by the yeast, and the composition elicits an HIV-specific T cell response. In one aspect of this embodiment of the invention, the fusion protein comprises the amino acid sequence of SEQ ID NO:86.

Yet another embodiment of the invention relates to an immunotherapeutic composition comprising: (a) a yeast; and (b) an HIV antigen expressed by the yeast and comprising an HIV Gag protein, wherein the HIV Gag protein forms very large particles (VLPs) when expressed by the yeast.

Another embodiment of the invention relates to an immunotherapeutic composition comprising: (a) a yeast; and (b) an HIV antigen expressed by the yeast and comprising an HIV Gag protein, wherein the HIV Gag protein does not form very large particles (VLPs) when expressed by the yeast.

In any embodiment related to an immunotherapeutic composition of the invention, including the embodiments described above, in one aspect, the yeast (or yeast vehicle) is from a yeast genus selected from the group consisting of: *Saccharomyces*, *Candida*, *Cryptococcus*, *Hansenula*, *Kluyveromyces*, *Pichia*, *Rhodotorula*, *Schizosaccharomyces* and *Yarrowia*.

In any embodiment related to an immunotherapeutic composition of the invention, including the embodiments described above, in one aspect, the yeast (or yeast vehicle) is from *Saccharomyces*.

In any embodiment related to an immunotherapeutic composition of the invention, including the embodiments described above, in one aspect, the yeast (or yeast vehicle) is from *Saccharomyces cerevisiae*.

In any embodiment related to an immunotherapeutic composition of the invention, including the embodiments described above, in one aspect, the further composition further includes a dendritic cell, wherein the dendritic cell has been loaded with the yeast.

In any embodiment related to an immunotherapeutic composition of the invention, including the embodiments described above, in one aspect, the composition is formulated in a pharmaceutically acceptable excipient suitable for administration to a subject by injection.

Another embodiment of the invention relates to a fusion protein comprising HIV antigens, wherein the fusion protein comprises an amino acid sequence that is at least 80% identical, at least 85% identical, at least 90% identical, at least 95% identical, at least 96% identical, at least 97% identical, at least 98% identical, at least 99% identical, or is identical to an amino acid sequence of: SEQ ID NO:5, SEQ ID NO:86, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, and/or SEQ ID NO:84.

Another embodiment of the invention relates to a recombinant nucleic acid molecule that encodes any of the fusion proteins described above or elsewhere herein. Yet another embodiment of the invention relates to an isolated cell transfected with such a recombinant nucleic acid molecule. In one aspect, such a cell is a yeast cell.

Another embodiment of the invention relates to a composition comprising any of the fusion proteins described above or elsewhere herein.

Yet another embodiment of the invention relates to a composition comprising any of the recombinant nucleic acid molecules described above or elsewhere herein.

Another embodiment of the invention relates to a composition comprising any of the isolated cells of described above or elsewhere herein.

One embodiment of the invention relates to a method to treat human immunodeficiency virus (HIV) infection or at least one symptom resulting from HIV infection in a subject, comprising administering to a subject that has been infected with HIV at least one of any of the compositions described above or elsewhere herein. In one aspect, the method further includes administering to the subject one or more additional compounds or compositions useful for treating or ameliorating a symptom of HIV infection. In one aspect, such an additional compound is an anti-viral compound, including, but not limited to, a fixed-dose combination (FDC) drug. In one aspect, the additional composition is a DNA vaccine. In one aspect, the additional composition is a processed yeast, including but not limited to, a yeast that was genetically modified to express at least one HIV antigen, or a yeast that expresses no antigen or an antigen that is not an HIV antigen. In one aspect, the processed yeast is administered with at least one HIV antigen, including, but not limited to, by admixture with an HIV antigen. In one aspect, the additional composition comprises autologous T cells from the subject, wherein the autologous T cells have been stimulated ex vivo with at least one HIV antigen. In one aspect, the additional composition comprises a protein subunit vaccine comprising at least one HIV antigen. In any of the aspects that include an additional composition and an HIV antigen, in one aspect, the HIV antigen is the same as the HIV antigen in the immunotherapeutic composition. In one aspect, the HIV antigen is different than the HIV antigen in the immunotherapeutic composition. In one aspect, the additional composition comprises a biological response modifier.

In any of the aspects of the invention related to an additional compound or composition, the additional compound or composition can be administered prior to administration of the immunotherapeutic composition, subsequent to administration of the immunotherapeutic composition, and/or concurrently with administration of the immunotherapeutic composition.

In one aspect of any of the methods or uses of the invention related to administration of an immunotherapeutic composition or other composition according to the invention, in one aspect, administration of the composition to the subject reduces HIV viral load in the subject. In one aspect, administration of the composition to the subject increases or stabilizes CD4$^+$ T cell counts in the subject. In one aspect, administration of the composition reduces the amount, duration or frequency of anti-viral therapy administered to the subject. In one aspect, administration of the composition results in a functional cure of HIV infection in the subject.

Another embodiment of the invention relates to a method to elicit an antigen-specific, cell-mediated immune response against an HIV antigen, comprising administering to a subject at least one of any of the compositions described above or elsewhere herein. In one aspect, the immune response is a cytotoxic T lymphocyte (CTL) response.

Yet another embodiment of the invention relates to a method to prevent HIV infection in a subject, comprising administering to a subject that has not been infected with HIV, at least one of any of the compositions described above or elsewhere herein.

Another embodiment of the invention relates to a method to immunize a population of individuals against HIV, comprising administering to the population of individuals at least one of any of the compositions described above or elsewhere herein.

Yet another embodiment of the invention relates to any of the compositions described above or elsewhere herein, for use to treat HIV infection or a symptom thereof.

Yet another embodiment of the invention relates to any of the compositions described above or elsewhere herein, for use to prevent HIV infection or a symptom thereof.

Another embodiment of the invention relates to the use of any of the compositions described above or elsewhere herein in the preparation of a medicament to treat HIV infection.

Yet another embodiment of the invention relates to the use of any of the compositions described above or elsewhere herein in the preparation of a medicament to prevent HIV infection.

DETAILED DESCRIPTION OF THE INVENTION

Figure 1:
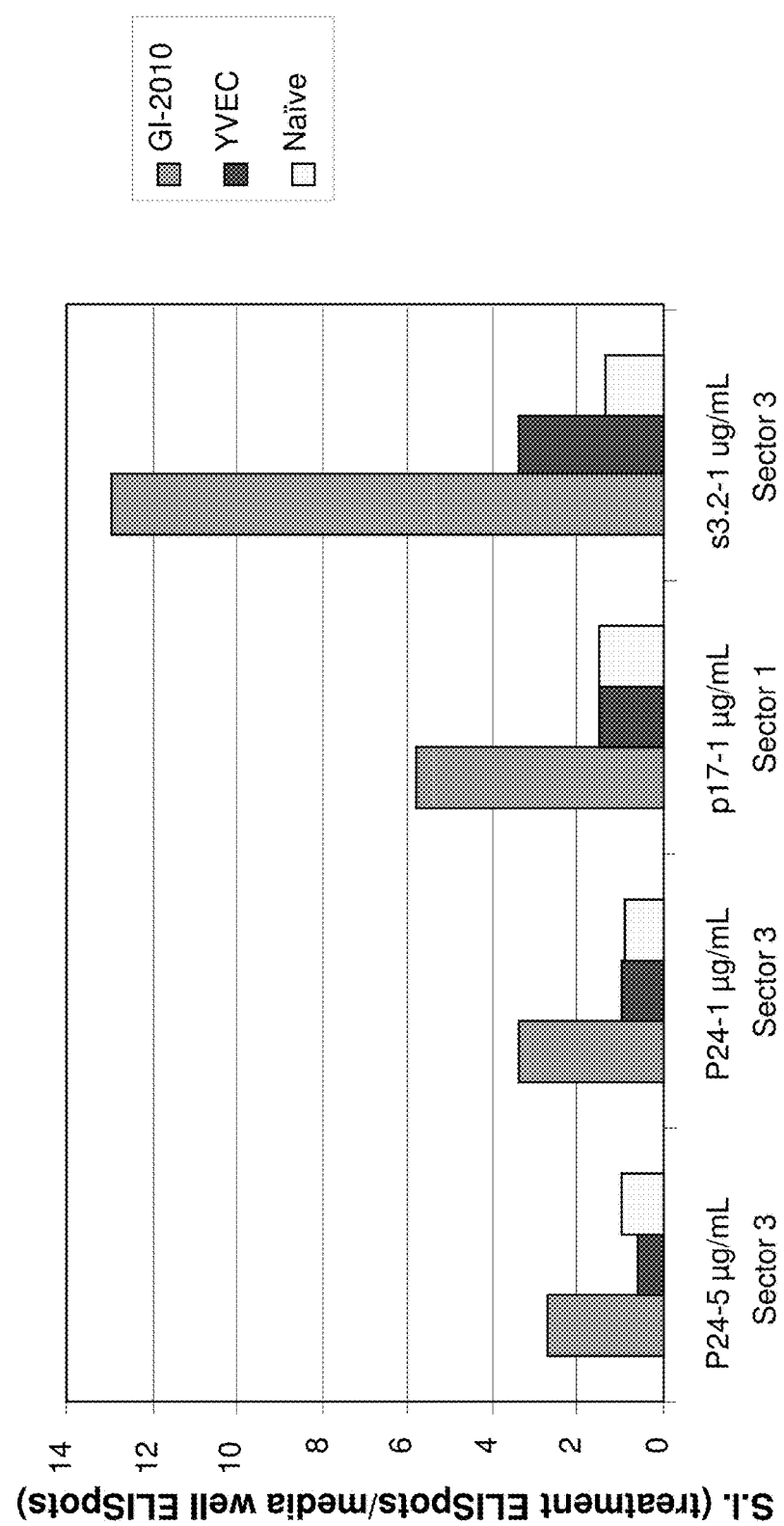
FIG. 1 is a graph showing interferon-γ (IFN-γ) ELISpot responses of GI-2010 immunized mice (gray bars) to subsequent in vitro stimulation with various HIV Gag Sector 3 antigens (black bars=YVEC control yeast (no antigen); white bars=naive, non-immunized mice control).

This invention generally relates to compositions and methods for preventing and/or treating human immunodeficiency virus (HIV) infection. The invention includes a yeast-based immunotherapeutic composition (also referred to as "yeast-based HIV immunotherapy") comprising a yeast vehicle and HIV antigen(s) that have been designed to elicit a prophylactic and/or therapeutic immune response against HIV infection in an individual, and the use of such compositions to prevent and/or treat HIV infection and related symptoms thereof. The invention also includes the recombinant nucleic acid molecules used in the yeast-based compositions of the invention, as well as the proteins and fusion proteins encoded thereby, for use in any immunotherapeutic composition and/or any therapeutic or prophylactic protocol for HIV infection, including any therapeutic or prophylactic protocol that combines the HIV-specific yeast-based compositions of the invention with any one or more other therapeutic or prophylactic compositions, agents, drugs, compounds, and/or protocols for HIV infection.

The yeast-based, HIV-specific immunotherapeutic compositions are unique among various types of immunotherapy, in that these compositions of the invention induce innate immune responses, as well as adaptive immune responses that specifically target HIV, including CD4-dependent TH17 and TH1 T cell responses and antigen-specific CD8$^+$ T cell responses. The breadth of the immune response elicited by HIV-specific yeast-based immunotherapy is well-suited to target HIV. Yeast-based HIV immunotherapy, by activating both the innate and the adaptive immune responses, and both CD4$^+$ and CD8$^+$ T cell responses, is expected to effectively target HIV-infected cells for destruction and/or is expected to effectively enhance viral clearance, as well as provide long term memory immunity against reactivating virus.

In addition, and without being bound by theory, yeast-based immunotherapy for HIV is believed to induce an immune response that is not only directed specifically against the target antigen carried by the yeast-based immunotherapeutic product, but that also evolves to be directed against other immunological epitopes on the virus (i.e., other than those carried by the yeast-antigen composition). In other words, a primary cellular immune response to the antigen(s) and/or epitope(s) contained in the yeast-based immunotherapeutic can lead to secondary cellular immune responses to antigen(s) and/or epitope(s) that are present in the infected cells in the treated subject but that are not present in the yeast-based immunotherapeutic, thereby leading to the evolution of complex and unpredictable immune response profiles that are unique to each treated subject. These secondary immune responses are specific to the molecular profile of the HIV infection in each subject treated, and the yeast-based immunotherapeutic may drive these downstream effects in a unique manner when compared to other treatment modalities, including other immunotherapy platforms. This phenomenon may also be generally referred to as "epitope spreading" and represents an advantage of using yeast-based HIV immunotherapy, because induction of an immune response against a particular HIV antigen or even against a particular HIV type, group, subtype, genotype or strain/isolate (e.g., by providing that antigen in the context of the yeast immunotherapeutic), is expected to result in the cascading targeting of the immune system against a variety of additional HIV antigens, which may result in effective immune responses against antigens from different HIV types, groups, subtypes, genotypes or strains than those represented in the yeast-based immunotherapeutic composition.

In one aspect of the invention, yeast-based HIV immunotherapy is combined with anti-viral drugs, and/or with other therapies for HIV, in order to reduce the viral load in an individual to a level that can be more effectively handled by the immune system.

Yeast-based immunotherapeutic compositions are administered as biologics or pharmaceutically acceptable compositions. Accordingly, rather than using yeast as an antigen production system followed by purification of the antigen from the yeast, the entire yeast vehicle as described herein must be suitable for, and formulated for, administration to a patient. Accordingly, the yeast-based immunotherapeutic compositions of the invention contain readily detectable yeast DNA and contain substantially more than 5% yeast protein; generally, yeast-based immunotherapeutics of the invention contain more than 70%, more than 80%, or generally more than 90% yeast protein.

Yeast-based immunotherapeutic compositions are administered to a patient in order to immunize the patient for therapeutic and/or prophylactic purposes. In one embodiment of the invention, the yeast-based compositions are formulated for administration in a pharmaceutically acceptable excipient or formulation. The composition should be formulated, in one aspect, to be suitable for administration to a human subject (e.g., the manufacturing conditions should be suitable for use in humans, and any excipients or formulations used to finish the composition and/or prepare the dose of the immunotherapeutic for administration should be suitable for use in humans). In one aspect of the invention, yeast-based immunotherapeutic compositions are formulated for administration by injection of the patient or subject, such as by a parenteral route (e.g., by subcutaneous, intraperitoneal, intramuscular or intradermal injection, or another suitable parenteral route).

In one embodiment, the yeast express the antigen (e.g., detectable by a Western blot), and the antigen is not aggregated in the yeast, the antigen does not form inclusion bodies in the yeast, and/or does not form very large particles (VLPs) or other large antigen particles in the yeast. In another embodiment, the antigen is produced as a soluble protein in the yeast, and/or is not secreted from the yeast or is not substantially or primarily secreted from the yeast. In yet another embodiment, particular combinations and/or arrangements of antigens in an HIV fusion protein are utilized in a yeast-based immunotherapeutic of the invention to intentionally form VLPs or aggregates within the yeast (discussed in more detail below). The resulting antigen expressed by the yeast is believed, without being bound by theory, to have additional immunogenic properties related to its overall structure and form, as a separate characteristic from the immunogenic properties of the immune epitopes (e.g., T cell epitopes) carried within the antigen. When the yeast expressing such fusion proteins are provided in a yeast-based HIV immunotherapeutic of the invention, the immunotherapeutic composition derives properties that activate the innate immune system not only from the yeast vehicle as discussed above (as with all yeast-based immunotherapeutics described herein), but also in part from the fusion protein antigen structure; in addition, the immunotherapeutic composition derives properties that activate the adaptive immune system in an antigen-specific manner from the fusion protein (via provision of various T cell epitopes), as with all of the yeast-based immunotherapeutics described herein. In all of the embodiments of the invention described herein, the yeast-based immunotherapeutics should be readily phagocytosed by dendritic cells of the immune system, and the yeast and antigens readily processed by such dendritic cells, in order to elicit an effective immune response against HIV.

Compositions of the Invention

One embodiment of the present invention relates to a yeast-based immunotherapy composition which can be used to prevent and/or treat HIV infection and/or to alleviate at least one symptom resulting from the HIV infection. The composition comprises: (a) a yeast vehicle; and (b) one or more antigens comprising HIV protein(s) and/or immunogenic domain(s) thereof. In conjunction with the yeast vehicle, the HIV proteins are most typically expressed as recombinant proteins by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or more such HIV proteins are loaded into a yeast vehicle or otherwise complexed with, attached to, mixed with or administered with a yeast vehicle as described herein to form a composition of the present invention. According to the present invention, reference to a "heterologous" protein or "heterologous" antigen, including a heterologous fusion protein, in connection with a yeast vehicle of the invention, means that the protein or antigen is not a protein or antigen that is naturally expressed by the yeast, although a fusion protein that includes heterologous antigen or heterologous protein may also include yeast sequences or proteins or portions thereof that are also naturally expressed by yeast (e.g., an alpha factor prepro sequence as described herein).

One embodiment of the invention relates to various HIV fusion proteins. In one aspect, such HIV fusion proteins are useful in a yeast-based immunotherapeutic composition of the invention. Such fusion proteins, and/or the recombinant nucleic acid molecules encoding such proteins, can also be used in, in combination with, or to produce, a non-yeast-based immunotherapeutic composition, which may include, without limitation, a DNA vaccine, a protein subunit vaccine, a recombinant viral-based immunotherapeutic composition, a killed or inactivated pathogen vaccine, a dendritic cell vaccine, and/or an autologous T cell vaccine (the subject's T cells that have been stimulated ex vivo using a fusion protein of the invention). In another embodiment, such fusion proteins can be used in a diagnostic assay for HIV and/or to generate antibodies against HIV. Described herein are exemplary HIV fusion proteins providing selected portions of HIV antigens, including, for example, selected portions of and/or modified polymerase (Pol), selected portions of and/or modified Gag, and selected portions of and/or modified envelope (Env), as well as selected portions of and/or arrangements of any one, two, or all three of these antigens.

Human Immunodeficiency Virus, Genes, and Proteins. HIV is a Group VI (ssRNA-RT) virus and a member of the virus family Retroviridae and the genus Lentivirus. It is widely accepted that HIV evolved at some point in time from closely related Simian immunodeficiency virus (SIV), and was transferred from non-human primates (SIV or HIV) to humans in the recent past. HIV can be divided into two main types or species, known as HIV type 1 (HIV-1) and HIV type 2 (HIV-2). HIV-1, the most common and pathogenic strain of the virus and the cause of most infections worldwide, is further divided into groups, which are each believed to represent an independent transmission of SIV into humans. Currently, HIV-1 has been divided into Groups M (for "major" or "main"), N, O and P, with Group M being the most prevalent HIV-1 group. Group M is further divided into clades, known generally as "subtypes" (e.g., subtypes A-K). Subtypes may be further divided into sub-subtypes and also "circulating recombinant forms" (CRF) where two subtypes are believed to have recombined to form a new subtype. HIV-2 has also been divided into groups, although only 2 groups (A and B) are epidemic.

HIV-1 contains 39 open reading frames (ORFS) in all possible six reading frames (Dwivedi et al., *I. Res. J. Biological Sci.*, 1(7), 52-54(2012), although only a few of them are functional. Although any HIV protein or functional, structural or immunogenic domain thereof, may be used in a yeast-based immunotherapy composition, three particularly useful proteins include HIV Gag, HIV Pol and HIV Env, and/or any functional, structural or immunogenic domain of any of these proteins. gag (group-specific antigen) encodes the precursor Gag polyprotein, which is processed by viral protease during maturation to MA (matrix protein, p17); CA (capsid protein, p24); SP1 (spacer peptide 1, p2); NC (nucleocapsid protein, p'7); SP2 (spacer peptide 2, p1) and p6 (King, Steven R. (1994) HIV: Virology and Mechanisms of disease. *Annals of Emergency Medicine.* 24:443-449). pol (polymerase) encodes the viral enzymes: reverse transcriptase (RT), RNase H, integrase, and HIV protease (Votteler and Schubert, (2008) Human Immunodeficiency Viruses: Molecular Biology. *Encyclopedia of Virology.* (3rd ed.) 517-525). HIV protease is required to cleave the precursor Gag polyprotein to produce structural proteins; RT is required to transcribe DNA from RNA template; integrase integrates the double-stranded viral DNA into the host genome (Mushahwar (2007) Human Immunodeficiency Viruses: Molecular Virology, pathogenesis, diagnosis and treatment. *Perspectives in Medical Virology.* 13:75-87). env (for "envelope") encodes gp160, which is cleaved by cellular protease rather than viral to produce the surface lipoprotein gp120 which attaches to the CD4 receptors present on lymphocytes and gp41 (transmembrane), proteins embedded in the viral envelope that enable the virus to attach to and fuse with target cells (Mushahwar, 2007, supra; King, 1994, supra).

The nucleic acid and amino acid sequence for HIV genes and the proteins encoded thereby are known in the art for a variety of strains/isolates from the various known HIV types, groups, and subtypes. It is noted that variations may occur in the amino acid sequence between different viral isolates of the same protein or domain from HIV. Using the guidance provided herein and the reference to the exemplary HIV sequences, one of skill in the art will readily be able to produce a variety of HIV-based proteins, including fusion proteins, from any HIV type, group, subtype, genotype or strain (isolate), for use in the compositions and methods of the present invention, and as such, the invention is not limited to the specific sequences disclosed herein. Reference to an HIV protein or HIV antigen anywhere in this disclosure, or to any functional, structural, or immunogenic domain thereof, can accordingly be made by reference to a particular sequence from one or more of the sequences presented in this disclosure, or by reference to the same, similar or corresponding sequence from a different HIV isolate (strain).

Human Immunodeficiency Virus Antigens and Constructs. One embodiment of the invention relates to novel HIV antigens and fusion proteins and recombinant nucleic acid molecules encoding these antigens and proteins. Described herein are several different novel HIV antigens for use in a yeast-based immunotherapeutic composition or other composition (e.g., other immunotherapeutic or diagnostic composition) that provide one or multiple (two, three, four, five, six, seven, eight, nine or more) antigens from one or more proteins, all contained within the same fusion protein and encoded by the same recombinant nucleic acid construct (recombinant nucleic acid molecule). The antigens used in the compositions of the invention include at least one HIV protein or immunogenic domain thereof for immunizing an animal (prophylactically or therapeutically). The composition can include one, two, three, four, a few, several or a plurality of HIV antigens, including one, two, three, four, five, six, seven, eight, nine, ten, or more immunogenic domains of one, two, three, four or more HIV proteins. In some embodiments, the antigen is a fusion protein. In one aspect of the invention, fusion protein can include two or more proteins. In one aspect, the fusion protein can include two or more immunogenic domains and/or two or more epitopes of one or more proteins. An immunotherapeutic composition containing such antigens may provide antigen-specific immunization in a broad range of patients. For example, an antigen or fusion protein encompassed by the invention can include at least a portion of, or the full-length of, any one or more HIV proteins selected from: HIV Gag, HIV Env, or HIV Pol; and/or any one or more immunogenic domains of any one or more of these HIV proteins. Other HIV proteins (e.g., Nef, Vif, Vpr, Tat, Rev, Vpu) may be used in an antigen construct in the invention, although use of Gag, Env and Pol is particularly preferred.

Recombinant nucleic acid molecules and the proteins encoded thereby, including fusion proteins, as one embodiment of the invention, may be used in yeast-based immunotherapy compositions, or for any other suitable purpose for HIV antigen(s), including in an in vitro assay, for the production of antibodies, or in another immunotherapy composition, including another vaccine, that is not based on the yeast-based immunotherapy described herein. Expression of the proteins by yeast is one preferred embodiment, although other expression systems may be used to produce the proteins for applications other than a yeast-based immunotherapy composition.

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies).

An antigen can be as small as a single epitope, a single immunogenic domain or larger, and can include multiple epitopes or immunogenic domains. As such, the size of an antigen can be as small as about 8-12 amino acids (i.e., a peptide) and as large as: a full length protein, a multimer, a fusion protein, a chimeric protein, a whole cell, a whole microorganism, or any portions thereof (e.g., lysates of whole cells or extracts of microorganisms). In addition, antigens can include carbohydrates, which can be loaded into a yeast vehicle or into a composition of the invention. It will be appreciated that in some embodiments (e.g., when the antigen is expressed by the yeast vehicle from a recombinant nucleic acid molecule), the antigen is a protein, fusion protein, chimeric protein, or fragment thereof, rather than an entire cell or microorganism.

When the antigen is to be expressed in yeast, an antigen is of a minimum size capable of being expressed recombinantly in yeast, and is typically at least or greater than 25 amino acids in length, or at least or greater than 26, at least or greater than 27, at least or greater than 28, at least or greater than 29, at least or greater than 30, at least or greater than 31, at least or greater than 32, at least or greater than 33, at least or greater than 34, at least or greater than 35, at least or greater than 36, at least or greater than 37, at least or greater than 38, at least or greater than 39, at least or greater than 40, at least or greater than 41, at least or greater than 42, at least or greater than 43, at least or greater than 44, at least or greater than 45, at least or greater than 46, at least or greater than 47, at least or greater than 48, at least or greater than 49, or at least or greater than 50 amino acids in length, or is at least 25-50 amino acids in length, at least 30-50 amino acids in length, or at least 35-50 amino acids in length, or at least 40-50 amino acids in length, or at least 45-50 amino acids in length. Smaller proteins may be expressed, and considerably larger proteins (e.g., hundreds of amino acids in length or even a few thousand amino acids in length) may be expressed. In one aspect, a full-length protein, or a structural or functional domain thereof, or an immunogenic domain thereof, that is lacking one or more amino acids from the N- and/or the C-terminus may be expressed (e.g., lacking between about 1 and about 20 amino acids from the N- and/or the C-terminus). Fusion proteins and chimeric proteins are also antigens that may be expressed in the invention. A "target antigen" is an antigen that is specifically targeted by an immunotherapeutic composition of the invention (i.e., an antigen against which elicitation of an immune response is desired). An "HIV antigen" is an antigen derived, designed, or produced from one or more HIV proteins such that targeting the antigen also targets the human immunodeficiency virus.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, an immunogen elicits a cell-mediated immune response, including a $CD4^+$ T cell response (e.g., TH1, TH2 and/or TH17) and/or a $CD8^+$ T cell response (e.g., a CTL response).

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a humoral immune response, where conformational domains are contemplated.

A "functional domain" of a given protein is a portion or functional unit of the protein that includes sequence or structure that is directly or indirectly responsible for at least one biological or chemical function associated with, ascribed to, or performed by the protein. For example, a functional domain can include an active site for enzymatic activity, a ligand binding site, a receptor binding site, a binding site for a molecule or moiety such as calcium, a phosphorylation site, or a transactivation domain.

A "structural domain" of a given protein is a portion of the protein or an element in the protein's overall structure that has an identifiable structure (e.g., it may be a primary or tertiary structure belonging to and indicative of several proteins within a class or family of proteins), is self-stabilizing and/or may fold independently of the rest of the protein. A structural domain is frequently associated with or features prominently in the biological function of the protein to which it belongs.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is actually recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be from 8 amino acids up to 25 amino acids or longer. In addition, T cell epitopes have predicted structural characteristics depending on the specific MHC molecules bound by the epitope. Multiple different T cell epitopes have been identified in various HIV strains and for many human HLA types. Epitopes can be linear sequence epitopes or conformational epitopes (conserved binding regions). Most antibodies recognize conformational epitopes.

An HIV antigen useful in the present invention, in one embodiment, comprises one or more CTL epitopes (e.g., epitopes that are recognized by a T cell receptor of a cytotoxic T lymphocyte (CTL), when presented in the context of an appropriate Class I MHC molecule). In one aspect, the HIV antigen comprises one or more $CD4^+$ T cell epitopes (e.g., epitopes that are recognized by a T cell receptor of a $CD4^+$ T cell, in the context of an appropriate Class II MHC molecule). In one aspect, the HIV antigen comprises one or more CTL epitopes and one or more $CD4^+$ T cell epitopes. In one aspect, an HIV antigen useful in an immunotherapeutic composition of the invention comprises one or more of the exemplary HIV CTL epitopes described in Table 1 or Table 2. One of skill in the art will readily be able to identify the position of the corresponding sequence for each epitope in Table 1 or Table 2 in a given HIV sequence of any strain/isolate, given the guidance provided below, even though some amino acids may differ from those in Table 1 or Table 2. The invention is not limited to antigens comprising these epitopes as others will be known in the art and are contemplated for use in the invention. In one embodiment, the epitope can be modified to correspond to the sequence of the epitope within a type, group, subtype, genotype or strain/isolate of HIV, since there may be one or more amino acid differences at these epitopes among type, group, subtype, genotype or strain/isolate.

In one embodiment of the invention, an HIV antigen useful in a yeast-based immunotherapeutic maximizes the inclusion of immunogenic domains, and particularly, T cell epitopes, that are conserved among HIV types, groups, subtypes, genotypes or strains/isolates, and/or includes immunogenic domains from several different types, groups, subtypes, genotypes or strains/isolates and/or includes immunogenic domains that can readily be modified to produce multiple yeast-based immunotherapeutic products that differ in some minor respects, but are tailored to treat different individuals or populations of individuals based on the HIV type, group, subtype, genotype or strain/isolate that infects such individuals or populations of individuals. For example, the HIV antigen can be produced based on an HIV-1 group(s) or subtype(s) that is most prevalent among individuals or populations of individuals to be protected or treated, and the HIV antigen includes the most conserved immunogenic domains from that group(s) or subtype(s). Alternatively or in addition, immunogenic domains can be modified to correspond to a consensus sequence for that domain or epitope, or more than one version of the epitope can be included in the construct.

In one embodiment of the invention, an HIV antigen useful in a yeast-based immunotherapeutic maximizes the inclusion of epitopes comprising one or more "sector 3" residues, and in a further aspect, which may also maximize the inclusion of epitopes comprising one or more "sector 1" residues. More specifically, in 2011, a publication by Dahirel et al. (2011, Proc. Natl. Acad. Sci. USA, 108(28):11530-5) identified and described distinct groups of amino acids whose mutations are collectively coordinated (generally denoted "HIV sectors") that map to structural determinants of intra- and inter-hexameric junctions of HIV Gag. One of the five HIV sectors in Gag, denoted "Sector 3", exhibited higher order conservation that indicated a multi-dimensional constraint on the viability of an HIV strain with multiple mutations in this sector. Furthermore, this sector, which renders the virus the most vulnerable, was the most targeted by the immune system of a class of HIV infected individuals, known as "elite non-progressors", i.e., persons who durably control HIV infection without medical intervention. Additional sites in the sector denoted "Sector 1" were also identified as potentially advantageous targets by Dahirel et al. The yeast-based immunotherapeutic compositions of the invention, being distinguished from many other types of immunotherapy by preferentially utilizing antigens that are larger protein domains and/or full-length proteins, has the advantage of including multiple epitopes, including sector 3 and/or sector 1 epitopes, thereby maximizing the potential for a productive immune response against HIV. More specifically, yeast-based immunotherapy for HIV optimizes the opportunity to generate strong T cell responses to these Sector 1 and Sector 3 epitopes based on the multiplicity of peptide processing by antigen presenting cells that phagocytosed the yeast immunotherapy compositions upon immunization, which may be specifically further enhanced by the introduction of agonist substitutions intentionally or unintentionally in key sector 1 and sector 3 domains.

In addition, as discussed in more detail below, the inventors propose herein to improve the targeting of multi-dimensional regions of HIV in an immunotherapy approach by introducing Altered Peptide Ligand (APL) sites that, without being bound by theory, are believed by the inventors to further enhance an immune response in individuals who are not elite non-progressors, enabling or facilitating the ability of such individuals to mount a productive immune response against the most vulnerable targets in the virus.

In any embodiment of the invention related to the design of an HIV antigen for a yeast-based immunotherapeutic composition, in one aspect, artificial junctions between segments of a fusion protein comprising HIV antigens is minimized (i.e., the inclusion of non-natural sequences is limited or minimized to the extent possible). Without being bound by theory, it is believed that natural evolution has resulted in: i) contiguous sequences in the virus that most likely to be expressed well in another cell, such as a yeast; and ii) an immunoproteasome in antigen presenting cells that can properly digest and present those sequences to the immune system. The yeast-based immunotherapeutic product of the invention allows the host immune system to process and present target antigens; accordingly, a fusion protein with many unnatural junctions may be less useful in a yeast-based immunotherapeutic as compared to one that retains more of the natural HIV protein sequences.

In any of the HIV antigens described herein, including any of the fusion proteins, the following additional embodiments can apply. First, an N-terminal expression sequence and/or a C-terminal tag are optional, and if used, may be selected from several different sequences described below to improve expression, stability, and/or allow for identification and/or purification of the protein. In one aspect, one or both of the N- or C-terminal sequences are omitted altogether. In addition, many different promoters suitable for use in yeast are known in the art and are encompassed for use to express HIV antigens according to the present invention. Furthermore, short intervening linker sequences (e.g., 1, 2, 3, 4, or 5, or larger, amino acid peptides) may be introduced between portions of the fusion protein for a variety of reasons, including the introduction of restriction enzyme sites to facilitate cloning and future manipulation of the constructs. Finally, as discussed in detail elsewhere herein, the sequences described herein are exemplary, and may be modified as described in detail elsewhere herein to substitute, add, or delete sequences in order to accommodate preferences for HIV strain or isolate, or consensus sequences and inclusion of preferred T cell epitopes, including dominant and/or subdominant T cell epitopes. A description of several different exemplary HIV antigens useful in the invention is provided below.

As discussed above, optionally, proteins, including fusion proteins, which are used as a component of the yeast-based immunotherapeutic composition of the invention, can be produced using constructs that are particularly useful for improving or enhancing the expression, or the stability of expression, of recombinant antigens in yeast. Typically, the desired antigenic protein(s) or peptide(s) are fused at their amino-terminal (N-terminal) end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, including but not limited to alpha factor, wherein either fusion partner provides improved stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). In addition, the present invention optionally includes the use of peptides that are fused to the C-terminus of the antigen-encoding construct, particularly for use in the selection and identification of the protein. Such peptides include, but are not limited to, any synthetic or natural peptide, such as a peptide tag (e.g., hexahistidine) or any other short epitope tag. Peptides attached to the C-terminus of an antigen according to the invention can be used with or without the addition of the N-terminal peptides discussed herein.

In one embodiment, a synthetic peptide useful in a fusion protein is linked to the N-terminus of the antigen, the peptide consisting of at least two amino acid residues that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but in one aspect, is 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-X2-X3-X4-X5-X6, wherein M is methionine; wherein X2 is any amino acid except glycine, proline, lysine or arginine; wherein X3 is any amino acid except methionine, lysine or arginine; wherein X4 is any amino acid except methionine, lysine or arginine; wherein X5 is any amino acid except methionine, lysine or arginine; and wherein X6 is any amino acid except methionine, lysine or arginine. In one embodiment, the X6 residue is a proline. An exemplary synthetic sequence that enhances the stability of expression of an antigen in a yeast cell and/or prevents post-translational modification of the protein in the yeast includes the sequence M-A-D-E-A-P (SEQ ID NO:81). Another exemplary synthetic sequence with the same properties is M-V. In addition to the enhanced stability of the expression product, these fusion partners do not appear to negatively impact the immune response against the immunizing antigen in the construct. In addition, the synthetic fusion peptides can be designed to provide an epitope that can be recognized by a selection agent, such as an antibody.

In one embodiment, the HIV antigen is linked at the N-terminus to a yeast protein, such as an alpha factor prepro sequence (also referred to as the alpha factor signal leader sequence, the amino acid sequence of which is exemplified herein by SEQ ID NO:82 or SEQ ID NO:83. Other sequences for yeast alpha factor prepro sequence are known in the art and are encompassed for use in the present invention.

The HIV sequences used to design fusion proteins described herein are based on isolates of particular human immunodeficiency viruses. However, it is an embodiment of the invention to add to or substitute into any portion of an HIV antigen described herein that is based on or derived from one particular strain or isolate, with a corresponding sequence, or even a single or small amino acid substitution, insertion or deletion that occurs in a corresponding sequence, from any other HIV strain(s) or isolate(s). In one embodiment, an HIV antigen can be produced by substituting an entire sequence(s) of an HIV antigen described herein with the corresponding sequence(s) from one or more different HIV strain/isolates. Adding to or substituting a sequence from one HIV strain for another, for example, allows for the customization of the immunotherapeutic composition for a particular individual or population of individuals (e.g., a population of individuals within a given country or region of a country, in order to target the HIV sequences that are most prevalent in that country or region of the country). Similarly, it is also an embodiment of the invention to use all or a portion of a consensus sequence derived from, determined from, or published for, a given HIV strain to make changes in the sequence of a given HIV antigen to more closely or exactly correspond to the consensus sequence. According to the present invention and as generally understood in the art, a "consensus sequence" is typically a sequence based on the most common nucleotide or amino acid at a particular position of a given sequence after multiple sequences are aligned.

As a particular example of the above-mentioned types of modifications, an HIV antigen can be modified to change a T cell epitope in a given sequence from one isolate to correspond more closely or exactly with a T cell epitope from a different isolate, or to correspond more closely or exactly with a consensus sequence for the T cell epitope. Such T cell epitopes can include dominant epitopes and/or sub-dominant epitopes. Alignments of major HIV proteins across exemplary sequences from various strains can be readily generated using publicly available software, which will inform the generation of consensus sequences, for example. Furthermore, consensus sequences for many HIV proteins have been published.

In one embodiment of the invention, the HIV antigen(s) for use in a composition or method of the invention is a fusion protein comprising HIV antigens, wherein the HIV antigens comprise or consist of HIV Gag or at least one functional, structural or immunogenic domain thereof; HIV Pol or at least one functional, structural or immunogenic domain thereof and/or HIV Env or at least one functional, structural or immunogenic domain thereof. According to any embodiment of the present invention, reference to a "full-length" protein (or a full-length functional domain, a full-length structural domain, or a full-length immunological domain) includes the full-length amino acid sequence of the protein or functional domain, structural domain or immunological domain, as described herein or as otherwise known or described in a publicly available sequence. A protein or domain that is "near full-length", which is also a type of homologue of a protein, differs from a full-length protein or domain, by the addition or deletion or omission of 1, 2, 3, 4, 5, 6, 7, 8, 9, or 10 amino acids from the N- and/or C-terminus of such a full-length protein or full-length domain. General reference to a protein or domain can include both full-length and near full-length proteins, as well as other homologues thereof.

In one aspect, the HIV antigen comprises at least 80%, 85%, 90%, 91%, 92%, 93%, 94%, 95%, 96%, 97%, 98%, or 99% of the linear sequence of a full-length HIV protein, or of a functional, structural or immunogenic domain thereof. In one aspect, the HIV antigen is at least 80%, 85%, 90%, 91%, 92%, 93%, 94%, 95%, 96%, 97%, 98%, or 99% identical to a full-length HIV protein, or a functional, structural or immunogenic domain thereof.

One example of a yeast-based immunotherapeutic composition for HIV useful in the present invention is described herein. In this embodiment, yeast (e.g., Saccharomyces cerevisiae) are engineered to express an HIV Gag p17-p24-p2 fusion protein, under the control of the copper-inducible promoter, CUP1, or the TEF2 promoter. In each case, the HIV fusion protein is a single polypeptide with the following sequence elements fused in frame from N- to C-terminus, represented by SEQ ID NO:1: 1) the amino acid sequence of an HIV Gag p17 protein (positions 1-132 of SEQ ID NO:1); 2) the amino acid sequence of an HIV p24 protein (positions 133-363 of SEQ ID NO:1); and 3) the amino acid sequence of an HIV Gag p2 protein (positions 364-377 of SEQ ID NO:1). As discussed above, this fusion protein can be constructed using any of the N-terminal and/or C-terminal sequences as described herein, and/or amino acid linkers can be introduced between proteins or domains in the fusion protein. In one aspect, since the first six amino acids of SEQ ID NO:1 are the sequence (M-G-A-R-A-S; positions 1-6 of SEQ ID NO:1), this protein is believed to accumulate well when expressed by yeast, and therefore, additional modification to improve expression, such as by the addition of SEQ ID NO:81, SEQ ID NO:82 or SEQ ID NO:83, is not believed to be necessary. In one aspect, the C-terminus of the fusion protein is modified to append a hexahistidine tag. The fusion protein represented by SEQ ID NO:1 contains both Sector 1 and Sector 3 residues (discussed above).

The p17 portion of SEQ ID NO:1, although it contains Sector 1 residues believed to be potentially beneficial in generating a productive immune response against HIV, is not very highly conserved among HIV strains/isolates as compared to the p24 portion of Gag. Accordingly, another example of a yeast-based a yeast-based immunotherapeutic composition for HIV useful in the present invention is represented by SEQ ID NO:2 and is described in Example 1. SEQ ID NO:2 contains only HIV Gag p24 and HIV Gag p2 proteins. In this embodiment, yeast (e.g., Saccharomyces cerevisiae) are engineered to express an HIV Gag p24-p2 fusion protein, under the control of the copper-inducible promoter, CUP1, or the TEF2 promoter. In each case, the HIV fusion protein is a single polypeptide with the following sequence elements fused in frame from N- to C-terminus, represented by SEQ ID NO:2: 1) the amino acid sequence of an HIV p24 protein (positions 1-231 of SEQ ID NO:2); and 2) the amino acid sequence of an HIV Gag p2 protein (positions 232-245 of SEQ ID NO:2). As discussed above, this fusion protein can be constructed using any of the N-terminal and/or C-terminal sequences as described herein, and/or amino acid linkers can be introduced between proteins or domains in the fusion protein. In one aspect, the N-terminus of the protein is modified to append a sequence represented by SEQ ID NO:76, SEQ ID NO:77 or SEQ ID NO:78. In one aspect, the C-terminus of the fusion protein is modified to append a hexahistidine tag.

Another example of a yeast-based immunotherapeutic composition for HIV useful in the present invention is described herein. In this embodiment, yeast (e.g., Saccharomyces cerevisiae) are engineered to express conserved, contiguous regions of HIV Gag p24 and p2, fused to one of the most highly conserved regions of HIV Pol, the Pol protease, under the control of the copper-inducible promoter, CUP1, or the TEF2 promoter. In each case, the HIV fusion protein is a single polypeptide with the following sequence elements fused in frame from N- to C-terminus, represented by SEQ ID NO:3: 1) the amino acid sequence of an HIV p24 protein (positions 1-231 of SEQ ID NO:3); 2) the amino acid sequence of an HIV Gag p2 protein (positions 232-245 of SEQ ID NO:3); and 3) the amino acid sequence of a portion of HIV Pol protease, lacking the N-terminal 19 amino acids which are well conserved among HIV strains (positions 246-325 of SEQ ID NO:3). The amino acid at position 251 of SEQ ID NO:3 is an aspartate in native HIV Pol protease, but is substituted with an alanine in SEQ ID NO:3 in order to eliminate protease activity by the fusion protein. As discussed above, this fusion protein can be constructed using any of the N-terminal and/or C-terminal sequences as described herein, and/or amino acid linkers can be introduced between proteins or domains in the fusion protein. In one aspect, the N-terminus of the protein is modified to append a sequence represented by SEQ ID NO:81, SEQ ID NO:82 or SEQ ID NO:83. In one aspect, the C-terminus of the fusion protein is modified to append a hexahistidine tag.

Another example of a yeast-based immunotherapeutic composition for HIV useful in the present invention is described here herein. In this embodiment, yeast (e.g., Saccharomyces cerevisiae) are engineered to express conserved, contiguous regions of HIV Gag p24 and p2, fused to one of the most highly conserved regions of HIV Pol, the Pol protease, and to a portion of HIV Pol reverse transcriptase (RT), under the control of the copper-inducible promoter, CUP1, or the TEF2 promoter. In each case, the HIV fusion protein is a single polypeptide with the following sequence elements fused in frame from N- to C-terminus, represented by SEQ ID NO:4: 1) the amino acid sequence of an HIV p24 protein (positions 1-231 of SEQ ID NO:4); 2) the amino acid sequence of an HIV Gag p2 protein (positions 232-245 of SEQ ID NO:4); 3) the amino acid sequence of a portion of HIV Pol protease, lacking the N-terminal 19 amino acids which are well conserved among HIV strains (positions 246-325 of SEQ ID NO:4); and 4) the amino acid sequence of a portion of the RT domain of HIV Pol, which is truncated to exclude sequences (polymerase motif region) that are known to possess many HIV escape mutations (positions 326-497 of SEQ ID NO:4). The amino acid at position 251 of SEQ ID NO:4 is an aspartate in native HIV Pol protease, but is substituted with an alanine in SEQ ID NO:4 in order to eliminate protease activity by the fusion protein. The amino acid at position 435 of SEQ ID NO:4 is an aspartate in the native HIV RT domain and is essential to the biological activity of the RT domain, but is substituted with an alanine in SEQ ID NO:4 to inactivate any potential activity of this enzyme in the yeast. Expression of viral polymerases in yeast may cause spurious or cryptic enzyme activity, adversely affecting the yeast transcriptional machinery. As discussed above, this fusion protein can be constructed using any of the N-terminal and/or C-terminal sequences as described herein, and/or amino acid linkers can be introduced between proteins or domains in the fusion protein. In one aspect, the N-terminus of the protein is modified to append a sequence represented by SEQ ID NO:81, SEQ ID NO:82 or SEQ ID NO:83. In one aspect, the C-terminus of the fusion protein is modified to append a hexahistidine tag.

Another example of a yeast-based immunotherapeutic composition for HIV useful in the present invention is described herein. In this embodiment, yeast (e.g., Saccharomyces cerevisiae) are engineered to express conserved, contiguous regions of HIV Gag p24 and p2, fused to one of the most highly conserved regions of HIV Pol, the Pol protease, and also to portions of Pol RNase H and Pol Integrase, under the control of the copper-inducible promoter, CUP1, or the TEF2 promoter. In each case, the HIV fusion protein is a single polypeptide with the following sequence elements fused in frame from N- to C-terminus, represented by SEQ ID NO:5: 1) the amino acid sequence of an HIV p24 protein (positions 1-231 of SEQ ID NO:5); 2) the amino acid sequence of an HIV Gag p2 protein (positions 232-245 of SEQ ID NO:5); 3) the amino acid sequence of a portion of HIV Pol protease, lacking the N-terminal 19 amino acids which are well conserved among HIV strains (positions 246-325 of SEQ ID NO:5); 4) the amino acid sequence of an HIV Pol RNase H protein (positions 326-445 of SEQ ID NO:5); and 5) the amino acid sequence of a portion of an HIV Pol Integrase protein (positions 446-567 of SEQ ID NO:5). The amino acid at position 251 of SEQ ID NO:3 is an aspartate in native HIV Pol protease, but is substituted with an alanine in SEQ ID NO:3 in order to eliminate protease activity by the fusion protein. The Pol Integrase portion of the fusion protein lacks the C-terminal 166 amino acids of the native protein. Specifically, the "140s loop" (see Perryman et al., 2010, *J. Mol. Biol.* 397(2):600-615) was excluded from SEQ ID NO:5 in order to ensure that the catalytic function of the integrase was excluded from the fusion protein. As discussed above, this fusion protein can be constructed using any of the N-terminal and/or C-terminal sequences as described herein, and/or amino acid linkers can be introduced between proteins or domains in the fusion protein. In one aspect, the N-terminus of the protein is modified to append a sequence represented by SEQ ID NO:81, SEQ ID NO:82 or SEQ ID NO:83. In one aspect, the C-terminus of the fusion protein is modified to append a hexahistidine tag.

For example, for stable expression in yeast, the fusion protein described above as SEQ ID NO:5, in one aspect, further includes an alpha factor leader sequence represented by SEQ ID NO:82 at the N-terminus of the fusion protein, which is fused to a two amino acid linker sequence of Thr-Ser, which is fused to the N-terminus of the HIV p24 protein, or the N-terminus of SEQ ID NO:5. The fusion protein further includes a hexahistidine sequence fused to the C-terminus (i.e., fused to the C-terminus of the HIV Pol Integrase protein of SEQ ID NO:5). The amino acid sequence of the entire fusion protein, including the N-terminal alpha factor sequence, linker sequence, HIV sequences, and C-terminal hexahistidine sequence is represented herein by SEQ ID NO:86, containing the following sequence elements fused in frame from N- to C-terminus: 1) the amino acid sequence of an alpha factor leader sequence (SEQ ID NO:82, positions 1-89 of SEQ ID NO:86); 2) a two amino acid linker sequence of Thr-Ser (positions 90-91 of SEQ ID NO:86); 3) the amino acid sequence of an HIV p24 protein (positions 1-231 of SEQ ID NO:5; positions 92-322 of SEQ ID NO:86); 4) the amino acid sequence of an HIV Gag p2 protein (positions 232-245 of SEQ ID NO:5; positions 323-336 of SEQ ID NO:86); 5) the amino acid sequence of a portion of HIV Pol protease, lacking the N-terminal 19 amino acids which are well conserved among HIV strains (positions 246-325 of SEQ ID NO:5; positions 337-416 of SEQ ID NO:86); 6) the amino acid sequence of an HIV Pol RNase H protein (positions 326-445 of SEQ ID NO:5; positions 417-536 of SEQ ID NO:86); 7) the amino acid sequence of a portion of an HIV Pol Integrase protein (positions 446-567 of SEQ ID NO:5; positions 537-658 of SEQ ID NO:86); and 8) a hexahistidine sequence (positions 659-664 of SEQ ID NO:86). A nucleic acid sequence encoding the fusion protein of SEQ ID NO:86, and accordingly, SEQ ID NO:5 (since SEQ ID NO:5 is contained within SEQ ID NO:86), codon optimized for yeast expression, is represented herein by SEQ ID NO:85. The yeast immunotherapy composition expressing SEQ ID NO:5 is also referred to herein as GI-2013.

Another example of a yeast-based immunotherapeutic composition for HIV useful in the present invention is described herein. In this embodiment, yeast (e.g., Saccharomyces cerevisiae) are engineered to express a portion of HIV Integrase, under the control of the copper-inducible promoter, CUP1, or the TEF2 promoter. In each case, the HIV protein is a single polypeptide comprising the amino acid sequence of a portion of an HIV integrase protein, represented by SEQ ID NO:6. The "140s loop" (see Perryman et al., 2010, *J. Mol. Biol.* 397(2):600-615) was excluded from SEQ ID NO:6 in order to ensure that the catalytic function of the integrase was excluded from the protein. As discussed above, this construct can be expressed as a fusion protein using any of the N-terminal and/or C-terminal sequences as described herein, and/or amino acid linkers can be introduced between proteins or domains in the fusion protein. In one aspect, the N-terminus of the protein is modified to append a sequence represented by SEQ ID NO:81, SEQ ID NO:82 or SEQ ID NO:83. In one aspect, the C-terminus of the fusion protein is modified to append a hexahistidine tag.

Another example of a yeast-based immunotherapeutic composition for HIV useful in the present invention is described herein. In this embodiment, yeast (e.g., *Saccharomyces cerevisiae*) are engineered to express a fusion of three, relatively conserved portions of HIV Env protein, under the control of the copper-inducible promoter, CUP1, or the TEF2 promoter. In each case, the HIV protein is a single polypeptide with the following sequence elements fused in frame from N- to C-terminus, represented by SEQ ID NO:7: 1) the amino acid sequence of an HIV Env protein, including the N-terminal region of gp41 through the immunodominant region of gp41 (positions 1-88 of SEQ ID NO:7); and 2) the amino acid sequence of an HIV Env protein, which is a short stretch of gp41 that is reasonably well conserved among HIV isolates (positions 89-129 of SEQ ID NO:7). As discussed above, this fusion protein can be constructed using any of the N-terminal and/or C-terminal sequences as described herein, and/or amino acid linkers can be introduced between proteins or domains in the fusion protein. In one aspect, the N-terminus of the protein is modified to append a sequence represented by SEQ ID NO:81, SEQ ID NO:82 or SEQ ID NO:83. In one aspect, the C-terminus of the fusion protein is modified to append a hexahistidine tag.

Several additional examples of a yeast-based immunotherapeutic composition for HIV useful in the present invention are described herein. Each of the following embodiments (represented by SEQ ID NOs:8-13) utilize a full-length HIV Gag protein (p17-p24-p2-p7), fused to selected portions of other HIV proteins in a manner that is believed to elicit an immune response against not only Sector 3 and Sector 1 epitopes, but also other HIV epitopes, in order to maximize a productive immune response against HIV. The amino acid sequence of the full-length Gag protein used in each of these constructs is represented by SEQ ID NO:74, and contains the following domains of Gag, from N- to C-terminus: HIV Gag p17 (positions 1-132 of SEQ ID NO:74); HIV Gag p24 (positions 132-363 of SEQ ID NO:74); HIV Gag p2 (positions 364-377 of SEQ ID NO:74); and HIV p7 (positions 378-432 of SEQ ID NO:74). A yeast-based immunotherapeutic composition expressing SEQ ID NO:74 is known herein as GI-2010.

One example of a yeast-based immunotherapeutic composition for HIV useful in the present invention and including SEQ ID NO:74 as a base element is represented by SEQ ID NO:8. In this embodiment, yeast (e.g., *Saccharomyces cerevisiae*) are engineered to express a full-length HIV Gag protein (p17-p24-p2-p7), fused to one of the most highly conserved regions of HIV Pol, the Pol protease, at the N-terminus, under the control of the copper-inducible promoter, CUP1, or the TEF2 promoter. The HIV fusion protein is a single polypeptide with the following sequence elements fused in frame from N- to C-terminus, represented by SEQ ID NO:8: 1) the amino acid sequence of a portion of HIV Pol protease, lacking the N-terminal 19 amino acids which are well conserved among HIV strains (positions 1-80 of SEQ ID NO:8); and 2) the amino acid sequence of an HIV Gag protein (p17-p24-p2-p7) (positions 81-512 of SEQ ID NO:8). The amino acid at position 6 of SEQ ID NO:8 is an aspartate in native HIV Pol protease, but is substituted with an alanine in SEQ ID NO:8 in order to eliminate protease activity by the fusion protein. As discussed above, this fusion protein can be constructed using any of the N-terminal and/or C-terminal sequences as described herein, and/or amino acid linkers can be introduced between proteins or domains in the fusion protein. In one aspect, the N-terminus of the protein is modified to append a sequence represented by SEQ ID NO:81, SEQ ID NO:82 or SEQ ID NO:83. In one aspect, the C-terminus of the fusion protein is modified to append a hexahistidine tag.

Another example of a yeast-based immunotherapeutic composition for HIV useful in the present invention and including SEQ ID NO:74 as a base element is represented by SEQ ID NO:9. In this embodiment, yeast (e.g., *Saccharomyces cerevisiae*) are engineered to express a full-length HIV Gag protein (p17-p24-p2-p7), fused to one of the most highly conserved regions of HIV Pol, the Pol protease, at the C-terminus, under the control of the copper-inducible promoter, CUP1, or the TEF2 promoter. The HIV fusion protein is a single polypeptide with the following sequence elements fused in frame from N- to C-terminus, represented by SEQ ID NO:9: 1) the amino acid sequence of an HIV Gag protein (p17-p24-p2-p7) (positions 1-432 of SEQ ID NO:9); and 2) the amino acid sequence of a portion of HIV Pol protease, lacking the N-terminal 19 amino acids which are well conserved among HIV strains (positions 433-512 of SEQ ID NO:9). The amino acid at position 438 of SEQ ID NO:9 is an aspartate in native HIV Pol protease, but is substituted with an alanine in SEQ ID NO:9 in order to eliminate protease activity by the fusion protein. As discussed above, this fusion protein can be constructed using any of the N-terminal and/or C-terminal sequences as described herein, and/or amino acid linkers can be introduced between proteins or domains in the fusion protein. In one aspect, since the first six amino acids of SEQ ID NO:9 are the sequence (M-G-A-R-A-S; positions 1-6 of SEQ ID NO:9), this protein is believed to accumulate well when expressed by yeast, and therefore, additional modification to improve expression, such as by the addition of SEQ ID NO:81, SEQ ID NO:82 or SEQ ID NO:83, is not believed to be necessary. In one aspect, the C-terminus of the fusion protein is modified to append a hexahistidine tag.

Another example of a yeast-based immunotherapeutic composition for HIV useful in the present invention and including SEQ ID NO:74 as a base element is represented by SEQ ID NO:10. In this embodiment, yeast (e.g., *Saccharomyces cerevisiae*) are engineered to express a full-length HIV Gag protein (p17-p24-p2-p7), fused to one of the most highly conserved regions of HIV Pol, the Pol reverse transcriptase (RT), at the N-terminus, under the control of the copper-inducible promoter, CUP1, or the TEF2 promoter. The HIV fusion protein is a single polypeptide with the following sequence elements fused in frame from N- to C-terminus, represented by SEQ ID NO:10: 1) the amino acid sequence of a portion of HIV Pol RT domain, which is truncated to exclude sequences (polymerase motif region) that are known to possess many HIV escape mutations (positions 1-172 of SEQ ID NO:10); and 2) the amino acid sequence of an HIV Gag protein (p17-p24-p2-p7) (positions 173-604 of SEQ ID NO:10). The amino acid at position 110 of SEQ ID NO:10 is an aspartate in the native HIV RT domain and is essential to the biological activity of the RT domain, but is substituted with an alanine in SEQ ID NO:10 to inactivate any potential activity of this enzyme in the yeast. As discussed above, this fusion protein can be constructed using any of the N-terminal and/or C-terminal sequences as described herein, and/or amino acid linkers can be introduced between proteins or domains in the fusion protein. In one aspect, the N-terminus of the protein is modified to append a sequence represented by SEQ ID NO:81, SEQ ID NO:82 or SEQ ID NO:83. In one aspect, the C-terminus of the fusion protein is modified to append a hexahistidine tag.

Another example of a yeast-based immunotherapeutic composition for HIV useful in the present invention and including SEQ ID NO:74 as a base element is represented by SEQ ID NO:11. In this embodiment, yeast (e.g., *Saccharomyces cerevisiae*) are engineered to express a full-length HIV Gag protein (p17-p24-p2-p7), fused to one of the most highly conserved regions of HIV Pol, the Pol reverse transcriptase (RT), at the C-terminus, under the control of the copper-inducible promoter, CUP1, or the TEF2 promoter. The HIV fusion protein is a single polypeptide with the following sequence elements fused in frame from N- to C-terminus, represented by SEQ ID NO:11: 1) the amino acid sequence of an HIV Gag protein (p17-p24-p2-p7) (positions 1-432 of SEQ ID NO:11); and 2) the amino acid sequence of a portion of HIV Pol RT domain, which is truncated to exclude sequences (polymerase motif region) that are known to possess many HIV escape mutations (positions 433-604 of SEQ ID NO:11). The amino acid at position 542 of SEQ ID NO:11 is an aspartate in the native HIV RT domain and is essential to the biological activity of the RT domain, but is substituted with an alanine in SEQ ID NO:11 to inactivate any potential activity of this enzyme in the yeast. As discussed above, this fusion protein can be constructed using any of the N-terminal and/or C-terminal sequences as described herein, and/or amino acid linkers can be introduced between proteins or domains in the fusion protein. In one aspect, since the first six amino acids of SEQ ID NO:11 are the sequence (M-G-A-R-A-S; positions 1-6 of SEQ ID NO:11), this protein is believed to accumulate well when expressed by yeast, and therefore, additional modification to improve expression, such as by the addition of SEQ ID NO:81, SEQ ID NO:82 or SEQ ID NO:83, is not believed to be necessary. In one aspect, the C-terminus of the fusion protein is modified to append a hexahistidine tag.

Another example of a yeast-based immunotherapeutic composition for HIV useful in the present invention and including SEQ ID NO:74 as a base element is represented by SEQ ID NO:12. In this embodiment, yeast (e.g., *Saccharomyces cerevisiae*) are engineered to express a full-length HIV Gag protein (p17-p24-p2-p7), fused to one of the most highly conserved regions of HIV Pol, the Pol Integrase, at the N-terminus, under the control of the copper-inducible promoter, CUP1, or the TEF2 promoter. The HIV fusion protein is a single polypeptide with the following sequence elements fused in frame from N- to C-terminus, represented by SEQ ID NO:12: 1) the amino acid sequence of a portion of HIV Pol integrase domain, which is truncated to exclude the "140s loop" in order to ensure that the catalytic function of the integrase was excluded from the protein (positions 1-122 of SEQ ID NO:12); and 2) the amino acid sequence of an HIV Gag protein (p17-p24-p2-p7) (positions 123-554 of SEQ ID NO:12). As discussed above, this fusion protein can be constructed using any of the N-terminal and/or C-terminal sequences as described herein, and/or amino acid linkers can be introduced between proteins or domains in the fusion protein. In one aspect, the N-terminus of the protein is modified to append a sequence represented by SEQ ID NO:81, SEQ ID NO:82 or SEQ ID NO:83. In one aspect, the C-terminus of the fusion protein is modified to append a hexahistidine tag.

Another example of a yeast-based immunotherapeutic composition for HIV useful in the present invention and including SEQ ID NO:74 as a base element is represented by SEQ ID NO:13. In this embodiment, yeast (e.g., *Saccharomyces cerevisiae*) are engineered to express a full-length HIV Gag protein (p17-p24-p2-p7), fused to one of the most highly conserved regions of HIV Pol, the Pol Integrase, at the C-terminus, under the control of the copper-inducible promoter, CUP1, or the TEF2 promoter. The HIV fusion protein is a single polypeptide with the following sequence elements fused in frame from N- to C-terminus, represented by SEQ ID NO:13: 1) the amino acid sequence of an HIV Gag protein (p17-p24-p2-p7) (positions 1-432 of SEQ ID NO:13); and 2) the amino acid sequence of a portion of HIV Pol integrase domain, which is truncated to exclude the "140s loop" in order to ensure that the catalytic function of the integrase was excluded from the protein (positions 433-554 of SEQ ID NO:13). As discussed above, this fusion protein can be constructed using any of the N-terminal and/or C-terminal sequences as described herein, and/or amino acid linkers can be introduced between proteins or domains in the fusion protein In one aspect, since the first six amino acids of SEQ ID NO:13 are the sequence (M-G-A-R-A-S; positions 1-6 of SEQ ID NO:13), this protein is believed to accumulate well when expressed by yeast, and therefore, additional modification to improve expression, such as by the addition of SEQ ID NO:81, SEQ ID NO:82 or SEQ ID NO:83, is not believed to be necessary. In one aspect, the C-terminus of the fusion protein is modified to append a hexahistidine tag.

Agonist Antigens. In some aspects of the invention, amino acid insertions, deletions, and/or substitutions can be made for one, two, three, four, five, six, seven, eight, nine, ten, or more amino acids of a wild-type or reference HIV protein, provided that the resulting HIV protein, when used as an antigen in a yeast-HIV immunotherapeutic composition of the invention, elicits an immune response against the target or wild-type or reference HIV protein, which may include an enhanced immune response, a diminished immune response, or a substantially similar immune response.

For example, the invention includes the use of HIV agonist antigens (also referred to herein as "Altered Peptide Ligands" (APLs), which are HIV antigens that may include one or more T cell epitopes, and particularly, cytotoxic T lymphocyte (CTL) epitopes, that have been mutated by substitution of one or more amino acid residues for a different amino acid residue(s) to create an "agonist epitope". The purpose of the mutation is to elicit a T cell response against the HIV agonist epitope that is enhanced/amplified/improved as compared to the response against the native antigen, which may be achieved by improving the avidity or affinity of the epitope for an MEW molecule or for the T cell receptor that recognizes the epitope in the context of MHC presentation. HIV antigen agonists may therefore improve the potency or efficiency of a T cell response against native HIV proteins that infect a host.

The present invention includes multiple novel HIV antigens harboring HIV Altered Peptide Ligand (APL) mutations (HIV agonist epitopes). These mutations are incorporated into an HIV Gag antigen or fusion protein comprising an HIV Gag antigen that is expressed by a yeast-based immunotherapy composition for HIV and, upon immunization of a subject, are designed to generate improved, enhanced or amplified T cell responses against the HIV-infected target cells as compared to T cell responses generated by a yeast-based immunotherapeutic composition expressing natural (native, or wild-type) HIV Gag sequences. As discussed above, the improved T cell responses may be due to improved avidity or affinity of the T cell epitope(s) in the antigen for the MHC molecule or for the T cell receptor that recognizes the epitope in the context of the MHC molecule.

The idea of using APL variants of CTL epitopes is an emerging concept in cancer vaccines, wherein the target of the immunotherapy may be a self-antigen, where an effective vaccine must break immune tolerance. Vaccination with APL peptides is one effective way to break tolerance. However, while APLs have been explored in CTL-inducing cancer vaccines, and also for use in enhancing antibody responses to infectious agents including HIV, the use of APLs or agonist peptides for CTL-inducing therapeutic vaccines targeting infectious diseases such as HIV (i.e., via a yeast-based immunotherapeutic of the invention) is believed to be a new concept unique to the present invention.

Accordingly, one embodiment of the present invention relates to a series of yeast-based immunotherapy compositions for HIV as described herein, in which the heterologous antigen expressed in the yeast is a highly conserved domain of HIV Gag with APL mutations at sites that are: i) highly invariant across HIV clades, and; ii) immunologically "vulnerable", on the basis that T cells targeting these sites are preferentially found in elite non-progressor patients (i.e., those that durably control HIV without medical intervention). Some of these "vulnerable" HIV Gag residues were recently identified using a computational algorithm and when mutated, are predicted to destabilize the HIV capsid by disrupting Gag inter-subunit interactions (Dahirel et al., 2011, supra). The key role of these residues, termed "sector 3" residues (see discussion above), aligns with the observation that patients with T cells capable of targeting epitopes containing these residues control viral progression.

Of note, HIV elite non-progressors typically possess HLA types that are not the prevailing alleles in the general population. An example of a prevailing allele in the general population and one which is present at relatively closely matched frequencies across multiple different races is HLA-A*0201. Therefore, the present inventors propose that a yeast-based immunotherapeutic composition with the ability to induce high avidity T cell responses to sector 3 residues in patients with common HLA alleles such as HLA-A*0201 represent a powerful new approach to HIV immunotherapy. The design and production of such immunotherapeutics is disclosed herein. For instance, Example 3 describes an experiment showing that immunization with a yeast-based immunotherapeutic expressing HIV Gag generated HLA-A2-specific, Gag Sector 1 and Sector 3-specific T cell responses in a mouse expressing human HLA-A2. Therefore, yeast-HIV immunotherapeutics comprising Sector 3 epitopes, generate T cell responses targeting an immunologically vulnerable region of Gag that are implicated in control of HIV.

More specifically, the present inventors propose herein a series of HIV Gag-APL antigens for use in a yeast-based immunotherapy composition in which the APLs are intended to elicit sector 3-targeted T cell responses in HLA-A2 subjects. These APL-induced T cell responses will be of higher avidity and efficacy than the responses normally observed for the corresponding peptides based on that they will be selected in a functional assay as described in the Examples.

To produce yeast-based immunotherapeutics that improve the efficacy of the T cell response to HIV Gag, two approaches are proposed. The following discussion describes the initial evaluation of class-I binding 9-mers, but the invention is not limited to 9-mers or to MHC Class I epitopes, as smaller or larger epitopes and/or MHC Class II epitopes can be evaluated for use in an HIV antigen according to the invention. In a first approach, in selected HIV T cell epitopes comprising one or more Sector 3 and/or Sector 1 residues, the substitution of peptide residues 2, 3 or 9 is utilized. These are the so called 'anchor' residues that are more conserved and that hold the peptides in the MHC Class I binding cleft. Alterations of these residues are made to increase the affinity of Peptide for MEW (see for example Van Stipdonk and Badia-Mrtinez et al. (2009). 69(19) 7784-7792). In a second approach, the substitution of residues 4 through 8 is utilized. This region includes residues that can arch away from the binding cleft and that interact with the T cell receptor. Alteration of these residues aims to modulate the affinity of the MHC/peptide for the T cell receptor (see for example Fong and Hou (2001). PNAS 98(15) 8809-8814). The use of HIV Gag sequences harboring combinations of sequences from both of these approaches may also be considered.

Not all MHC Class-I restricted HIV epitopes for modification by the present invention are exactly 9 amino acids; some are up to 11 amino acids and in these cases, the number of residues between the anchors may vary.

The epitopes in HIV elite non-progressors bind MHC alleles other than the ubiquitous HLA-A*-0201. An additional facet included in the design of the HIV Gag-APL antigens of the invention therefore included the use of residues at key anchor positions that are preferred or at least compatible with binding to the HLA-A*0201. Preferred HLA-A*0201 binding residues at upstream (*usually position 2) are L, M, and V, and tolerated residues at this position are T, Q, A, and I. Preferred HLA-A*0201 binding residues at the C terminus are I, V, and L, and tolerated residues at the C terminus are M, T, and A (Sidney and Southwood et al 2001 Human Immunology 62:1200-1216).

Table 1 represents five epitopes associated with control of HIV and that encompass sector 3 residues, the "native" sequence represented in column 2. Peptide #5 is an epitope newly discovered by the present inventors. For each epitope, the inventors have designed six different APL epitopes based on the rationale discussed above. These designs attempted to both change the affinity of binding of the epitope to MEW Class I, and to make the peptide more prone to HLA-A*0201 binding.

TABLE 1

APL Designs (Anchor Residue Alteration)

| Peptide # | SEQUENCE (Sector 3 in bold) | HLA Binding of Native Peptide | APL Modifications (Sector 3 in bold; APL Residues Underlined) | Anchor of TCR affinity change | SEQ ID NO: |
|---|---|---|---|---|---|
| 1 | KAFSPEVIPMF (SEQ ID NO: 76) | B57 | KALSPEVIPMV | Anchor | 14 |
| | | | KAMSPEVIPMV | Anchor | 15 |
| | | | KAVSPEVIPMV | Anchor | 16 |

TABLE 1-continued

APL Designs (Anchor Residue Alteration)

| Peptide # | SEQUENCE (Sector 3 in bold) | HLA Binding of Native Peptide | APL Modifications (Sector 3 in bold; APL Residues Underlined) | Anchor of TCR affinity change | SEQ ID NO: |
|---|---|---|---|---|---|
| | | | KA<u>L</u>SPEV<u>IPMI</u> | Anchor | 17 |
| | | | KA<u>M</u>SPEV<u>IPMI</u> | Anchor | 18 |
| | | | KA<u>V</u>SPEV<u>IPMI</u> | Anchor | 19 |
| 2 | TSTLQEQIGW (SEQ ID NO: 77) | B57 | TS<u>LL</u>QEQIG<u>V</u> | Anchor | 20 |
| | | | TS<u>M</u>LQEQIG<u>V</u> | Anchor | 21 |
| | | | TS<u>V</u>LQEQIG<u>V</u> | Anchor | 22 |
| | | | TS<u>LL</u>QEQIG<u>I</u> | Anchor | 23 |
| | | | TS<u>M</u>LQEQIG<u>I</u> | Anchor | 24 |
| | | | TS<u>V</u>LQEQIG<u>I</u> | Anchor | 25 |
| 3 | KRWIILGLNK (SEQ ID NO: 78) | B27 | KR<u>L</u>IILGLN<u>V</u> | Anchor | 26 |
| | | | KR<u>M</u>IILGLN<u>V</u> | Anchor | 27 |
| | | | KR<u>V</u>IILGLN<u>V</u> | Anchor | 28 |
| | | | KR<u>L</u>IILGLN<u>I</u> | Anchor | 29 |
| | | | KR<u>M</u>IILGLN<u>I</u> | Anchor | 30 |
| | | | KR<u>V</u>IILGLN<u>I</u> | Anchor | 31 |
| 4 | DRFYKTLRA (SEQ ID NO: 79) | B14 | D<u>L</u>FYKTLR<u>V</u> | Anchor | 32 |
| | | | D<u>M</u>FYKTLR<u>V</u> | Anchor | 33 |
| | | | D<u>V</u>FYKTLR<u>V</u> | Anchor | 34 |
| | | | D<u>L</u>FYKTLR<u>V</u> | Anchor | 35 |
| | | | D<u>M</u>FYKTLR<u>I</u> | Anchor | 36 |
| | | | D<u>V</u>FYKTLR<u>I</u> | Anchor | 37 |
| 5 | YVDRFYKTLRA* (SEQ ID NO: 80) | unknown | YVD<u>L</u>FYKTLR<u>V</u> | Anchor | 38 |
| | | | YVD<u>M</u>FYKTLR<u>V</u> | Anchor | 39 |
| | | | YVD<u>V</u>FYKTLR<u>V</u> | Anchor | 40 |
| | | | YVD<u>L</u>FYKTLR<u>I</u> | Anchor | 41 |
| | | | YVD<u>M</u>FYKTLR<u>I</u> | Anchor | 42 |
| | | | YVD<u>V</u>FYKTLR<u>I</u> | Anchor | 43 |

*novel epitope discovered by the inventors.

Table 2 represents the same five epitopes described in Table 1 above that are associated with control of HIV, but in each case showing six different proposed APL designs that alter the TCR-binding region of the peptide. In designing the following peptides, the inventors used the following rationale, choosing modifications that: i) are centrally located between anchor residues as these will have maximal chance of affecting the interaction with the TCR, and; ii) only subtly affect the steric environment. Too large a structural change could completely abolish any recognition by the TCR and could also affect MHC binding directly or indirectly by altering the conformational dynamics of the peptide. Examples of residue changes that would minimize the disruptive steric effects include but are not limited to "conservative substitutions", such as: 1) asparagine/aspartic acid; 2) glutamine/glutamic acid; 3) phenylalanine/tyrosine, 4) arginine/lysine, 5) glycine/alanine, 6) leucine/isoleucine, 7) valine/leucine, 8) valine/alanine, 9) serine/threonine.

TABLE 2

APL Designs (TCR:MHC/peptide interaction)

| Peptide # | SEQUENCE (Sector 3 in bold) | HLA Binding of Native Peptide | APL Modifications (Sector 3 in bold; APL Residues Underlined) | Anchor of TCR affinity change | SEQ ID NO: |
|---|---|---|---|---|---|
| 1 | KAFSPEVIPMF (SEQ ID NO: 76) | B57 | KAFSPE<u>L</u>IPMF | TCR | 44 |
| | | | KAFSPE<u>A</u>IPMF | TCR | 45 |
| | | | KAFSPEV<u>L</u>PMF | TCR | 46 |
| | | | KAF<u>T</u>PEVIPMF | TCR | 47 |
| | | | KAFSP<u>Q</u>VIPMF | TCR | 48 |
| | | | KAFSP<u>D</u>VIPMF | TCR | 49 |
| 2 | TSTLQEQIGW (SEQ ID NO: 77) | B57 | TSTLQ<u>N</u>EQIGW | TCR | 50 |
| | | | TSTLQE<u>N</u>IGW | TCR | 51 |
| | | | TSTL<u>EE</u>QIGW | TCR | 52 |
| | | | TSTLQ<u>E</u>EIGW | TCR | 53 |
| | | | TSTLQ<u>Q</u>QIGW | TCR | 54 |
| | | | TSTLQ<u>D</u>QIGW | TCR | 55 |

TABLE 2-continued

APL Designs (TCR:MHC/peptide interaction)

| Peptide # | SEQUENCE (Sector 3 in bold) | HLA Binding of Native Peptide | APL Modifications (Sector 3 in bold; APL Residues Underlined) | Anchor of TCR affinity change | SEQ ID NO: |
|---|---|---|---|---|---|
| 3 | KRWIILGLNK (SEQ ID NO: 78) | B27 | KRWLILGLNK | TCR | 56 |
| | | | KRWILLGLNK | TCR | 57 |
| | | | KRWIIIGLNK | TCR | 58 |
| | | | KRWIILALNK | TCR | 59 |
| | | | KRWIILGINK | TCR | 60 |
| | | | KRWIILGVNK | TCR | 61 |
| 4 | DRFYKTLRA (SEQ ID NO: 79) | B14 | DRFYRTLRA | TCR | 62 |
| | | | DRFYMTLRA | TCR | 63 |
| | | | DRFYKSLRA | TCR | 64 |
| | | | DRFYKTIRA | TCR | 65 |
| | | | DRFYKTVRA | TCR | 66 |
| | | | DRFYKTARA | TCR | 67 |
| 5

It is known that VLPs formed by expression of viral antigens, including hepatitis B virus (HBV) core and hepatitis C virus (HCV) core are highly immunogenic, possessing adjuvant-like properties and eliciting potent T cell responses (e.g., Sominskaya I, Skrastina D 2010 Clin. Vaccine Immun. 17(6) 1027-33; Acosta-Rivero N, et al 2005 BBRC 334(3): 901-6). HIV-1 Gag-virus-like particles as subunit vaccines have been shown to be safe and potent HIV-vaccine candidates that elicit strong cellular and humoral immunity without need of any adjuvant (J Innate Immun. 2012; 4(5-6): 579-90). Without being bound by theory, the present inventors believe that a whole yeast-based immunotherapeutic, in which the heterologous antigen expressed within the yeast cytoplasm is in the form of a VLP, will be a particularly effective T cell-activating entity, due to early and late presentation of antigens with MHC Class I, as follows.

In the prevailing model of yeast-based immunotherapy activity, the following steps lead to cross-presentation of the yeast-expressed (heterologous) antigen: i) phagocytosis of yeast by antigen presenting cells (APCs), including dendritic cells, induces maturation of the phagosome into the proteolytically competent phagolysosome, ii) degradation of the yeast and heterologous antigen release into the lumen on the phagolysosome; iii) heterologous antigen is transported to the cytosol and the antigen is subjected to proteasomal degradation to produce peptides; iv) the peptides are transported to the ER lumen via the TAP transporter, and is coupled with MEW loading; and v) peptide/MHC complexes are transported to the plasma membrane in vesicles.

It was recently published that for VLPs, an alternate pathway can lead to presentation of the VLP antigen with class I MHC. Class I presentation in this case occurs by loading onto class I MHC molecules that have been recycled from the cell surface (Win S J, Ward V K (2011). *Immunol. Cell Biol.* 89(6):681-8.). This direct process occurs with faster kinetics than the classical pathway.

The present inventors propose herein to create a whole yeast-based immunotherapeutic composition comprised of whole yeast that express both soluble HIV Gag and HIV Gag VLPs. Without being bound by theory, the inventors believe that such a vaccine has enhanced T cell-stimulating potency, as compared to other types of vaccines, or to yeast expressing only soluble HIV Gag or only VLP HIV Gag. The soluble form of HIV Gag is anticipated to be more slowly presented via the classical pathway, whereas the VLP form of HIV Gag is presented more quickly, via the class I MEW recycling pathway. The net result is that antigen would be presented by the APC for a longer net period of time than for yeast expressing only the VLP or only the soluble form of Gag. This longer time frame of antigen presentation affords greater opportunity for interaction with cognate T cells. The amino acid sequence of SEQ ID NO:74 described herein is representative of a sequence for full-length HIV Gag that forms VLPs in yeast.

In another embodiment, the present invention relates to a yeast-based immunotherapy composition in which the HIV antigens comprise HIV Gag antigens that are not in VLP form, but rather in soluble/non-oligomerizing form. In this embodiment, the antigen is designed to enhance proteolytic digestion of the antigen by the APC in order to increase cross-presentation efficiency. As discussed above, the sequence of wild type HIV-1 Gag represented by SEQ ID NO:74 forms VLPs. Therefore, the inventors have modified the VLP-assembling sequence to become a soluble/non-oligomerizing form, which can be used in this aspect of the invention, or in combination with the VLP form in a single yeast, as described above. In one aspect, the antigen is modified by deleting the N-terminal glycine (underlined) in positions 1-5 of SEQ ID NO:74 MGARA which has been previously shown by Sakuragi et al. 2002 to abolish the ability of HIV-1 Gag to form VLPs. Such an HIV antigen suitable for use in the present invention is represented herein by SEQ ID NO:75. Another method to produce an HIV Gag antigen that does not form VLPs is to delete all or a portion of the p7/nucleocapsid region. The HIV Gag antigen represented by SEQ ID NO:1 is an example of such an antigen.

The invention also includes homologues of any of the above-described fusion proteins, as well as the use of homologues, variants, or mutants of the individual HIV proteins or portions thereof (including any functional and/or immunogenic domains) that are part of such fusion proteins or otherwise described herein. In one aspect, the invention includes the use of fusion proteins or individual (single) HIV proteins or HIV antigens, having amino acid sequences that are at least 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of any one of the fusion proteins or individual HIV proteins or HIV antigens, respectively, described herein, including any of the HIV proteins, HIV antigens and fusion proteins referenced by a specific sequence identifier herein (e.g., any one of SEQ ID NOs:1-13, an HIV antigen comprising or consisting of any one of SEQ ID NOs:14-73, SEQ ID NO:74 or SEQ ID NO:75), over the full length of the fusion protein, or with respect to a defined segment in the fusion protein or a defined protein or domain thereof (immunogenic domain or functional domain (i.e., a domain with at least one biological activity)) that forms part of the fusion protein. Many CTL epitopes (epitopes that are recognized by cytotoxic T lymphocytes from patients infected with HIV) and escape mutations (mutations that arise in an HIV protein due to selective pressure from an anti-viral drug) are known in the art, and this information can also be used to make substitutions or create variants or homologues of the HIV antigens described herein in order to provide a specific sequence in the HIV antigen of the invention.

Another aspect of the invention includes an HIV antigen comprising, consisting essentially of, or consisting of, an amino acid sequence represented by any one or more of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, and/or SEQ ID NO:75. The HIV antigen is suitable for use in any of the embodiments of the invention described herein, including in a yeast-based immunotherapy composition described herein.

Yeast-Based Immunotherapy Compositions. In various embodiments of the invention, the invention includes the use of at least one "yeast-based immunotherapeutic composition" (which phrase may be used interchangeably with "yeast-based immunotherapy product", "yeast-based immunotherapy composition", "yeast-based composition", "yeast-based immunotherapeutic", "yeast-based vaccine", or derivatives of these phrases). An "immunotherapeutic composition" is a composition that elicits an immune response sufficient to achieve at least one therapeutic benefit in a subject. As used herein, yeast-based immunotherapeutic composition refers to a composition that includes a yeast vehicle component and that elicits an immune response sufficient to achieve at least one therapeutic benefit in a subject. More particularly, a yeast-based immunotherapeutic composition is a composition that includes a yeast vehicle component and can elicit or induce an immune response, such as a cellular immune response, including without limitation a T cell-mediated cellular immune response. In one aspect, a yeast-based immunotherapeutic composition useful in the invention is capable of inducing a $CD8^+$ and/or a $CD4^+$ T cell-mediated immune response and in one aspect, a $CD8^+$ and a $CD4^+$ T cell-mediated immune response. Optionally, a yeast-based immunotherapeutic composition is capable of eliciting a humoral immune response. A yeast-based immunotherapeutic composition useful in the present invention can, for example, elicit an immune response in an individual such that the individual is protected from HIV infection and/or is treated for HIV infection or for symptoms resulting from HIV infection.

Yeast-based immunotherapy compositions of the invention may be either "prophylactic" or "therapeutic". When provided prophylactically, the compositions of the present invention are provided in advance of any symptom of HIV infection. Such a composition could be administered perinatally (e.g., to a mother before birth, which may followed by administration to the infant at or shortly after birth, for example to protect an infant of a mother who is or may have been infected with HIV), at or shortly after birth of an infant, in early childhood, in later childhood or adolescence, and/or to adults, particularly adults who may be at higher risk of becoming infected with HIV. The prophylactic administration of the immunotherapy compositions serves to prevent subsequent HIV infection, to resolve an infection more quickly or more completely if HIV infection subsequently ensues, and/or to ameliorate the symptoms of HIV infection if infection subsequently ensues. When provided therapeutically, the immunotherapy compositions are provided at or after the onset of HIV infection, with the goal of ameliorating at least one symptom of the infection and preferably, with a goal of eliminating the infection, providing a long lasting remission of infection, and/or providing long term immunity against subsequent infections.

Typically, a yeast-based immunotherapy composition includes a yeast vehicle and at least one antigen or immunogenic domain thereof expressed by, attached to, or mixed with the yeast vehicle, wherein the antigen is heterologous to the yeast, and wherein the antigen comprises one or more HIV antigens or immunogenic domains thereof. In some embodiments, the antigen or immunogenic domain thereof is provided as a fusion protein. Several HIV fusion proteins suitable for use in the compositions and methods of the invention have been described herein. In one aspect of the invention, fusion protein can include two or more antigens. In one aspect, the fusion protein can include two or more immunogenic domains of one or more antigens, or two or more epitopes of one or more antigens.

In any of the yeast-based immunotherapy compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition of the invention, or in one aspect, the yeast vehicle can be used alone or as an adjuvant. The yeast vehicle can therefore include, but is not limited to, a live intact (whole) yeast microorganism (i.e., a yeast cell having all its components including a cell wall), a killed (dead) or inactivated intact yeast microorganism, or derivatives of intact/whole yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

In one aspect of the invention, the yeast vehicle is a whole yeast. In one aspect, the yeast is a "processed yeast" (described below; generally a yeast that has been ground up or processed in a manner to produce yeast cell wall preparations, yeast membrane particles and/or yeast fragments (i.e., not intact), as well as a soluble yeast proteins. In one aspect, the yeast vehicle includes both a whole yeast and a processed yeast, administered either together, in concurrent but separate injections, or in sequential injections (e.g., temporally separated, which may include a prime-boost strategy).

Yeast spheroplasts are typically produced by enzymatic digestion of the yeast cell wall. Such a method is described, for example, in Franzusoff et al., 1991, *Meth. Enzymol.* 194, 662-674, incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is a preparation of isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains).

Genera of yeast strains that may be used in the invention include but are not limited to *Saccharomyces, Candida, Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, yeast genera are selected from *Saccharomyces, Hansenula*, and *Pichia*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe*. *S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used in the present invention, including those that exhibit reduced post-translational modifications of expressed target antigens or other proteins, such as mutations in the enzymes that extend N-linked glycosylation.

In most embodiments of the invention, the yeast-based immunotherapy composition includes at least one antigen, immunogenic domain thereof, or epitope thereof. The antigens contemplated for use in this invention include any HIV protein or immunogenic domain thereof, including mutants, variants and agonists of HIV proteins or domains thereof, against which it is desired to elicit an immune response for the purpose of prophylactically or therapeutically immunizing a host against HIV infection. HIV antigens that are useful in various embodiments of the invention are described in detail above, and elsewhere herein.

In one aspect of the invention, the yeast vehicle is manipulated such that the antigen is expressed or provided by delivery or translocation of an expressed protein product, partially or wholly, on the surface of the yeast vehicle (extracellular expression). One method for accomplishing this aspect of the invention is to use a spacer arm for positioning one or more protein(s) on the surface of the yeast vehicle. For example, one can use a spacer arm to create a fusion protein of the antigen(s) or other protein of interest with a protein that targets the antigen(s) or other protein of interest to the yeast cell wall. For example, one such protein that can be used to target other proteins is a yeast protein (e.g., cell wall protein 2 (cwp2), Aga2, Pir4 or Flo1 protein) that enables the antigen(s) or other protein to be targeted to the yeast cell wall such that the antigen or other protein is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) or other proteins to be exposed on the yeast surface is to use signal sequences such as glycosylphosphatidyl inositol (GPI) to anchor the target to the yeast cell wall. Alternatively, positioning can be accomplished by appending signal sequences that target the antigen(s) or other proteins of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length. Another consideration for optimizing antigen surface expression, if that is desired, is whether the antigen and spacer arm combination should be expressed as a monomer or as dimer or as a trimer, or even more units connected together. This use of monomers, dimers, trimers, etc. allows for appropriate spacing or folding of the antigen such that some part, if not all, of the antigen is displayed on the surface of the yeast vehicle in a manner that makes it more immunogenic.

Use of yeast proteins can stabilize the expression of fusion proteins in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

Other sequences can be used to target, retain and/or stabilize the protein to other parts of the yeast vehicle, for example, in the cytosol or the mitochondria or the endoplasmic reticulum or the nucleus. Examples of suitable yeast protein that can be used for any of the embodiments above include, but are not limited to, TK, AF, SECT; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation (e.g., a pharmaceutically acceptable excipient). These types of complexes are described in detail below.

In one embodiment, a yeast cell used to prepare the yeast vehicle is transfected with a heterologous nucleic acid molecule encoding a protein (e.g., the antigen) such that the protein is expressed by the yeast cell. Such a yeast is also referred to herein as a recombinant yeast or a recombinant yeast vehicle. The whole yeast cell, or a derivative or other modified vehicle produced from this yeast cell (e.g., yeast spheroplasts, cytoplasts, ghosts, or subcellular particles), can then be administered to a subject, including in a pharmaceutically acceptable excipient. In one aspect of the invention, the yeast vehicle can then be loaded into a dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen or other protein.

In general, the yeast vehicle and antigen(s) and/or other agents can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) is expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 heterologous antigens and or other proteins.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SECT) and acid phosphatase (PHO5), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego).

In some embodiments of the invention, yeast are grown under neutral pH conditions. As used herein, the general use of the term "neutral pH" refers to a pH range between about pH 5.5 and about pH 8, and in one aspect, between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. In one embodiment, yeast are grown in a medium maintained at a pH level of at least 5.5 (i.e., the pH of the culture medium is not allowed to drop below pH 5.5). In another aspect, yeast are grown at a pH level maintained at about 6, 6.5, 7, 7.5 or 8. The use of a neutral pH in culturing yeast promotes several biological effects that are desirable characteristics for using the yeast as vehicles for immunomodulation. For example, culturing the yeast in neutral pH allows for good growth of the yeast without negative effect on the cell generation time (e.g., slowing of doubling time). The yeast can continue to grow to high densities without losing their cell wall pliability. The use of a neutral pH allows for the production of yeast with pliable cell walls and/or yeast that are more sensitive to cell wall digesting enzymes (e.g., glucanase) at all harvest densities. This trait is desirable because yeast with flexible cell walls can induce different or improved immune responses as compared to yeast grown under more acidic conditions, e.g., by promoting the secretion of cytokines by antigen presenting cells that have phagocytosed the yeast (e.g., TH1-type cytokines including, but not limited to, IFN-γ, interleukin-12 (IL-12), and IL-2, as well as proinflammatory cytokines such as IL-6). In addition, greater accessibility to the antigens located in the cell wall is afforded by such culture methods.

In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5).

In one embodiment, control of the amount of yeast glycosylation is used to control the expression of antigens by the yeast, particularly on the surface. The amount of yeast glycosylation can affect the immunogenicity and antigenicity of the antigen expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce the amount of glycosylation of the yeast (or increase it, if desired). For example, one could use a yeast mutant strain that has been selected to have low glycosylation (e.g., mnn1, och1 and mnn9 mutants), or one could eliminate by mutation the glycosylation acceptor sequences on the target antigen. Alternatively, one could use a yeast with abbreviated glycosylation patterns, e.g., *Pichia*. One can also treat the yeast using methods that reduce or alter the glycosylation.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to an individual or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment of the invention, the yeast vehicle and the antigen or other protein are both loaded intracellularly into a carrier such as a dendritic cell or macrophage to form the therapeutic composition or vaccine of the present invention. For example, a recombinant yeast cell (yeast that has been genetically engineered to express an antigen of the invention) can be loaded into a dendritic cell as an intact cell, or the yeast cell can be killed, or it can be derivatized or otherwise modified such as by formation of yeast spheroplasts, cytoplasts, ghosts, or subcellular particles, any of which is followed by loading of the derivative into a dendritic cell. Alternatively, an antigen or other protein can be loaded into a dendritic cell in the absence of the yeast vehicle.

In one embodiment, intact yeast (with or without expression of heterologous antigens or other proteins) can be ground up or processed in a manner to produce yeast cell wall preparations, yeast membrane particles and/or yeast fragments (i.e., not intact), as well as a soluble yeast proteins. Such a yeast can be referred to herein as a "smashate" or "processed yeast". The processed yeast can, in some embodiments, be provided with or administered with one or more HIV antigens described herein, and/or in conjunction with other compositions that encode, include or have been in contact with HIV antigens (e.g., DNA vaccines, viral vector vaccines, protein subunit vaccines, autologous T cell vaccines, killed or inactivated pathogens, antibody vaccines) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention, including preparations to be administered to a subject directly or first loaded into a carrier such as a dendritic cell, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include additional agents, which may also be referred to as biological response modifier compounds, or the ability to produce such agents/modifiers. For example, a yeast vehicle can be transfected with or loaded with at least one antigen and at least one agent/biological response modifier compound, or a composition of the invention can be administered in conjunction with at least one agent/biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). Certain biological response modifiers have one or more properties in common with the biological properties of yeast-based immunotherapeutics or enhance or complement the biological properties of yeast-based immunotherapeutics. There are a number of techniques known to those skilled in the art to measure stimulation or suppression of immune responses, as well as to differentiate cell-mediated immune responses from humoral immune responses, and to differentiate one type of cell-mediated response from another (e.g., a TH17 response versus a TH1 response).

Agents/biological response modifiers useful in the invention may include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Agents useful in combination with a yeast-based immunotherapy composition in accordance with the invention include, but are not limited to: anti-CD40, CD40L, lymphocyte-activation gene 3 (LAG3) protein and/or IMP321 (T-cell immunostimulatory factor derived from the soluble form of LAG3), anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®); anti-CD4; anti-CD25; anti-PD-1, anti-PD-L1, anti-PD-L2; agents that block FOXP3 (e.g., to abrogate the activity/kill CD4+/CD25+T regulatory cells); Flt3 ligand, imiquimod (Aldara™), Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMiDs® (which are structural and functional analogues of thalidomide (e.g., REVLIMID® (lenalidomide), POMALYST® (pomalidomide)) and any agents that modulate the number of, modulate the activation state of, and/or modulate the survival of antigen-presenting cells or of TH17, TH1, and/or Treg cells. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein. In addition, one or more therapies can be administered or performed prior to the first dose of yeast-based immunotherapy composition or after the first dose is administered.

Agents can include agonists and antagonists of a given protein or peptide or domain thereof. As used herein, an "agonist" is any compound or agent, including without limitation small molecules, proteins, peptides, antibodies, nucleic acid binding agents, etc., that binds to a receptor or ligand and produces or triggers a response, which may include agents that mimic the action of a naturally occurring substance that binds to the receptor or ligand. An "antagonist" is any compound or agent, including without limitation small molecules, proteins, peptides, antibodies, nucleic acid binding agents, etc., that blocks or inhibits or reduces the action of an agonist.

Compositions of the invention can further include or can be administered with (concurrently, sequentially, or intermittently with) any other compounds or compositions that are useful for preventing or treating HIV infection or any compounds that treat or ameliorate any symptom of HIV infection. A variety of agents are known to be useful for treating or ameliorating HIV infection. Such agents are described in detail elsewhere herein and include, but are not limited to, anti-viral compounds, including fixed-dose combinations (FDCs). These agents are typically administered for long periods of time (e.g., daily for the lifetime of the patient). In addition, compositions of the invention can be used together with other immunotherapeutic compositions, including prophylactic and/or therapeutic immunotherapy, such compositions include, but are not limited to, DNA vaccines, dendritic cell vaccines, viral vector vaccines, protein subunit vaccines, autologous T cell vaccines, killed or inactivated pathogens, and/or antibody vaccines. Compositions of the invention can also be administered or used together with biological response modifiers (described above), many of which have immunomodulatory properties (e.g., anti-PD-1, anti-CTLA-4, etc.).

The invention also includes a kit comprising any of the compositions described herein, or any of the individual components of the compositions described herein.
Methods for Administration or Use of Compositions of the Invention Compositions of the invention, which can include any one or more (e.g., combinations of two, three, four, five, or more) yeast-based immunotherapeutic compositions described herein, HIV antigens including HIV proteins and fusion proteins, and/or recombinant nucleic acid molecules encoding such HIV proteins or fusion proteins described above, and other compositions comprising such yeast-based compositions, antigens, proteins, fusion proteins, or recombinant molecules described herein, can be used in a variety of in vivo and in vitro methods, including, but not limited to, to treat and/or prevent HIV infection and its sequelae, in diagnostic assays for HIV, or to produce antibodies against HIV.

One embodiment of the invention relates to a method to treat human immunodeficiency virus (HIV) infection, and/or to prevent, ameliorate or treat at least one symptom of HIV infection, in an individual or population of individuals. The method includes the step of administering to an individual or a population of individuals who are infected with HIV one or more immunotherapeutic compositions of the invention. In one aspect, the composition is an immunotherapeutic composition comprising one or more HIV antigens as described herein, which can include a yeast-based immunotherapeutic composition. In one aspect, the composition includes a protein or fusion protein comprising HIV antigens as described herein, and/or recombinant nucleic acid molecule encoding such protein or fusion protein. In one embodiment, the individual or population of individuals has HIV infection. In one aspect, the individual or population of individuals is additionally treated with at least one other therapeutic compound and/or additional composition useful for the treatment of HIV infection. Such therapeutic compounds and/or additional compositions include, but are not limited to, direct-acting antiviral drugs (e.g., those described above or elsewhere herein, including, but not limited to, FDC drugs) and/or other immunotherapeutic or immunomodulatory agents, including, but not limited to, DNA vaccines (i.e., nucleic acid based vaccines encoding HIV antigens), viral vector vaccines (e.g., virus-based vectors encoding HIV antigens), dendritic cell vaccines (e.g., dendritic cells comprising HIV antigens, including dendritic cells comprising yeast expressing or carrying HIV antigens), protein subunit vaccines (e.g., recombinant HIV proteins), autologous T cell vaccines (e.g., T cells isolated from an individual and stimulated ex vivo, for example, with HIV antigens or other immunomodulatory agents), killed or inactivated pathogens (e.g., killed or inactivated HIV strains), antibody vaccines (e.g., therapeutic or prophylactic antibodies), and/or biological response modifiers (described elsewhere herein).

"Standard Of Care" or "SOC" generally refers to the current approved standard of care for the treatment of a specific disease. In HIV infection, SOC may be one of several different approved therapeutic protocols, and includes, but may not be limited to, anti-viral therapy. Currently approved anti-viral drugs for the treatment of HIV infection include fixed dose combination (FDCs) drugs, comprised of cross-class drugs provided as a single pill taken once daily. Such FDCs include, but are not limited to: ATRIPLA® (tenofovir disoproxil fumarate/emtricitabine/efavirenz: tenofovir/NRTI+emtricitabine/NRTI, with efavirenz (a non-nucleoside reverse transcriptase inhibitor (NNRTI) from Bristol Myers-Squibb), Gilead Sciences, Inc.); COMPLERA® (tenofovir disoproxil fumarate/emtricitabine/rilpivirine: tenofovir/NRTI+emtricitabine/NRTI, with rilpivirine (a NNRTI from Tibotec/Johnson & Johnson), Gilead Sciences, Inc.); and STRIBILD/QUAD® (tenofovir disoproxil fumarate/emtricitabine/elvitegravir/cobicistat: tenofovir/NRTI+emtricitabine/NRTI, with cobicistat-boosted elvitegravir (integrase inhibitor from Japan Tobacco), Gilead Sciences, Inc.). An FDC known as 572-TRII® (abcavir/NRTI+lamivudine/NRTI, with dolutegravir (integrase inhibitor from Pfizer/Shionogi), ViiV (GlaxoSmithKline, Pfizer, Shionogi) is currently seeking FDA approval. The immunotherapeutic composition of the invention can be administered prior to, concurrently with, intermittently with, and/or after one or more anti-viral(s) and/or other immunotherapeutic or immunomodulatory agents. The other therapeutic compounds may also be administered prior to or after treatment with the immunotherapeutic compositions of the invention.

In one embodiment of the invention, a yeast-based HIV immunotherapy composition of the invention is administered concurrently or sequentially (including in a prime-boost strategy) with a second immunotherapy composition that enhances a humoral immune response to HIV antigens. For example, when the yeast-based HIV immunotherapy composition is provided in the form of a whole, recombinant yeast expressing one or more HIV antigens, the immune response generated by this composition is primarily cellular in nature (e.g., elicits T cell responses), although priming of a humoral immune response also occurs. In order to enhance functional cures of HIV infection, it is, in one embodiment of the invention, desirable to induce both a strong cellular and a strong humoral immune response against HIV. Therefore, the invention contemplates the use of compositions together with yeast-based immunotherapy that are particularly suited to enhance humoral immune responses. Such compositions may include, but are not limited to: a processed yeast immunotherapy composition comprising HIV antigens (described elsewhere herein), a protein subunit vaccine expressing or otherwise comprising HIV antigens, or a DNA or viral vector vaccine expressing HIV antigens.

In one aspect of the invention, a whole recombinant yeast expressing one or more HIV antigens as described herein is administered concurrently with a processed yeast comprising one or more HIV antigens as described herein, either together in a single injection or in separate injections. In one aspect, a whole recombinant yeast expressing one or more HIV antigens as described herein is administered sequentially (e.g., in a prime-boost strategy) with a processed yeast comprising one or more HIV antigens as described herein. Optionally, the processed yeast comprising one or more HIV antigens may also be included in the priming dose with the whole recombinant yeast expressing one or more HIV antigens.

In one embodiment, a DNA vaccine encoding HIV antigen(s) is utilized in a prime-boost protocol with one or more yeast-based immunotherapy compositions. DNA vaccines using in vivo electroporation have been used to elicit cellular immune responses in a variety of studies of viral disease including HIV, and may include boosters using viral vectors (see, e.g., Catanzaro et al., *J Infect Dis* 2006; 194:1638-1649). However, viral vector immunotherapy and DNA immunotherapy are known to suffer from neutralization of the vaccine over time/repeated administrations. Yeast-based immunotherapy does not suffer from neutralization effects and can be administered multiple times over long periods. Therefore, it is an embodiment of the invention to prime an individual with a DNA vaccine for HIV using a suitable method such as electroporation, followed by boosters using a yeast-based HIV immunotherapy composition of the invention. Such a method (or any method of the invention that utilizes yeast-based HIV immunotherapy as at least one component) is effective for eliciting a robust immune response and maintaining long term immunological pressure on infected cells. In one aspect, the yeast-based HIV immunotherapy composition is a whole recombinant yeast expressing one or more HIV antigens as described herein. In another aspect, the yeast-based HIV immunotherapy composition is a processed yeast comprising one or more HIV antigens as described herein. In another aspect, the yeast-based HIV immunotherapy composition is a combination of a whole recombinant yeast expressing one or more HIV antigens as described herein and a processed yeast comprising one or more HIV antigens as described herein, wherein the whole yeast and the processed yeast are administered concurrently in a single injection or in separate injections. Additional therapeutic compounds and/or compositions may be further included in this method as described herein (e.g., anti-viral therapy, additional types of boosters such as protein subunit vaccines, immunomodulatory biological response modifiers, etc.).

In one embodiment of the invention, a yeast-based HIV immunotherapy composition of the invention is loaded into a dendritic cell ex vivo to form a dendritic cell vaccine. For example, dendritic cells from a subject to be treated can be isolated from the subject, loaded with a yeast-based HIV immunotherapy composition of the invention, and then returned to the subject. Optionally, before, after, or at the same time, T cells isolated from the subject (autologous T cells) may be stimulated ex vivo with the same yeast-based HIV immunotherapy composition (and/or another immunotherapy composition or immunomodulator/biological response modifier) and also returned to the subject. Dendritic cells are cells of monocyte and lymphocyte lineages, and are known to be the most potent antigen presenting cell (APC) and to stimulate antigen-specific T cell responses. Mature dendritic cells are typically identified as having the following cell surface marker phenotype: $MAC3^-$, $CD80^+$, $CD86^+$, $CD40^{low}$, $CD54^+$, MHC Class I and MHC Class II, and are capable of FITC-dextran uptake. The dendritic cell used in the composition of the present invention is preferably isolated from a patient to which the composition is to be administered (i.e., autologous cells). Dendritic cells can be isolated from the bone marrow or peripheral blood. Such cells can be generated, for example, from peripheral blood monocytes by culture in the presence of granulocyte macrophage colony-stimulating factor, IL-4, and TNF", for example. Other methods for isolating and generating dendritic cells are known in the art (See, for example, Wilson et al., 1999, *J Immunol* 162: 3070-8; Romani et al., 1994, *J Exp Med* 180: 83-93; Caux et al., 1996, *J Exp Med* 184: 695-706; and Kiertscher et al., 1996, *J Leukoc Biol* 59: 208-18, each of which is incorporated herein by reference in its entirety). A therapeutic composition effective to administer to a patient contains from about $0.5 \times 10^6$ to about $40 \times 10^6$ dendritic cells per single dose per individual patient. Preferably, a therapeutic composition contains from about $1 \times 10^6$ to about $20 \times 10^6$ dendritic cells per single dose per patient, and in another embodiment, from about $1 \times 10^6$ to about $10 \times 10^6$ dendritic cells per single dose per patient. These doses are given for a typical human or other primate. To "load" a component into a cell references any technique by which the component is either forced to enter the cell (e.g., by electroporation) or is placed in an environment (e.g., in contact with or near to a cell) where the component will be substantially likely to enter the cell by some process (e.g., phagocytosis). Loading techniques include, but are not limited to: diffusion, active transport, liposome fusion, electroporation, phagocytosis, and bath sonication. In a preferred embodiment, passive mechanisms for loading a dendritic cell with the yeast vehicle and/or antigen are used, such passive mechanisms including phagocytosis of the yeast vehicle and/or antigen by the dendritic cell.

Another embodiment of the invention relates to a method to immunize an individual or population of individuals against HIV in order to prevent HIV infection and/or reduce the severity of HIV infection in the individual or population of individuals. The method includes the step of administering to an individual or population of individuals that is not infected with HIV (or believed not to be infected with HIV), a composition of the invention. In one aspect, the composition is an immunotherapeutic composition comprising one or more HIV antigens as described herein, including one or more yeast-based immunotherapeutic compositions. In one aspect, the composition includes a fusion protein comprising HIV antigens as described herein, or recombinant nucleic acid molecule encoding such fusion protein.

As used herein, the phrase "treat" HIV infection, or any permutation thereof (e.g., "treated for HIV infection", etc.) generally refers to applying or administering a composition of the invention once the infection (acute or chronic) has occurred, with the goal of reduction or elimination of detectable viral titer or viral load; reduction in at least one symptom resulting from the infection in the individual; delaying or preventing the onset and/or severity of symptoms and/or downstream sequelae caused by the infection (e.g., development of AIDS and diseases or conditions associated with AIDS); reduction of organ or physiological system damage resulting from the infection; improvement of immune responses against the virus; improved CD4+ T cell counts; improvement of long term memory immune responses against the virus; reduced reactivation of virus; reduction in the frequency, duration and/or amount of HAART or similar therapies needed to achieve long term remission; and/or improved general health of the individual or population of individuals. In one embodiment, a method to treat HIV according to the present invention results in a "functional cure" (i.e., containment of HIV replication and prevention of disease in the absence of ongoing treatment).

To "prevent" HIV infection, or any permutation thereof (e.g., "prevention of HIV infection", etc.), generally refers to applying or administering a composition of the invention before an infection with HIV has occurred, with the goal of preventing infection by HIV, or, should the infection later occur, at least reducing the severity, and/or length of infection and/or the physiological damage caused by the infection, including preventing or reducing the severity or incidence of at least one symptom resulting from the infection in the individual, and/or delaying or preventing the onset and/or severity of symptoms and/or downstream sequelae caused by the infection, in an individual or population of individuals.

The present invention includes the delivery (administration, immunization) of one or more immunotherapeutic compositions of the invention, including a yeast-based immunotherapy composition, to a subject. The administration process can be performed ex vivo or in vivo, but is typically performed in vivo. Ex vivo administration refers to performing part of the regulatory step outside of the patient, such as administering a composition of the present invention to a population of cells (e.g., dendritic cells) removed from a patient under conditions such that a yeast vehicle, antigen(s) and any other agents or compositions are loaded into the cell, and returning the cells to the patient. The therapeutic composition of the present invention can be returned to a patient, or administered to a patient, by any suitable mode of administration.

Administration of a composition can be systemic, mucosal and/or proximal to the location of the target site (e.g., near a site of infection). Suitable routes of administration will be apparent to those of skill in the art, depending on the type of condition to be prevented or treated, the antigen used, and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992). Other routes of administration that modulate mucosal immunity may be useful in the treatment of viral infections. Such routes include bronchial, intradermal, intramuscular, intranasal, other inhalatory, rectal, subcutaneous, topical, transdermal, vaginal and urethral routes. In one aspect, an immunotherapeutic composition of the invention is administered subcutaneously.

With respect to the yeast-based immunotherapy compositions of the invention, in general, a suitable single dose is a dose that is capable of effectively providing a yeast vehicle and an antigen (if included) to a given cell type, tissue, or region of the patient body in an amount effective to elicit an antigen-specific immune response against one or more HIV antigens or epitopes, when administered one or more times over a suitable time period. For example, in one embodiment, a single dose of a yeast vehicle of the present invention is from about $1 \times 10^5$ to about $5 \times 10^7$ yeast cell equivalents per kilogram body weight of the organism being administered the composition. In one aspect, a single dose of a yeast vehicle of the present invention is from about 0.1 Y.U. ($1 \times 10^6$ cells) to about 100 Y.U. ($1 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$ . . . ). In one embodiment, doses include doses between 1 Y.U. and 40 Y.U., doses between 1 Y.U. and 50 Y.U., doses between 1 Y.U. and 60 Y.U., doses between 1 Y.U. and 70 Y.U., or doses between 1 Y.U. and 80 Y.U., and in one aspect, between 10 Y.U. and 40 Y.U., 50 Y.U., 60

Y.U., 70 Y.U., or 80 Y.U. In one embodiment, the doses are administered at different sites on the individual but during the same dosing period. For example, a 40 Y.U. dose may be administered via by injecting 10 Y.U. doses to four different sites on the individual during one dosing period, or a 20 Y.U. dose may be administered by injecting 5 Y.U. doses to four different sites on the individual, or by injecting 10 Y.U. doses to two different sites on the individual, during the same dosing period. The invention includes administration of an amount of the yeast-based immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose.

"Boosters" or "boosts" of a therapeutic composition are administered, for example, when the immune response against the antigen has waned or as needed to provide an immune response or induce a memory response against a particular antigen or antigen(s). Boosters can be administered from about 1, 2, 3, 4, 5, 6, 7, or 8 weeks apart, to monthly, to bimonthly, to quarterly, to annually, to several years after the original administration. In one embodiment, an administration schedule is one in which from about $1 \times 10^5$ to about $5 \times 10^7$ yeast cell equivalents of a composition per kg body weight of the organism is administered at least 1, 2, 3, 4, 5, 6, 7, 8, 9, 10, or more times over a time period of from weeks, to months, to years. In one embodiment, the doses are administered weekly for 1, 2, 3, 4, 5, 6, 7, 8, 9, 10 or more doses, followed by monthly doses as needed to achieve the desired inhibition or elimination of the HIV virus. In one embodiment, the doses are administered in a 4-weekly protocol (every 4 weeks, or on day 1, week 4, week 8, week 12, etc., for between 2 and 10 doses or longer as determined by the clinician). Additional doses can be administered even after the individual achieves seroconversion, if desired, although such dosing may not be necessary.

In one embodiment of the invention, as discussed above, a different (non-yeast-based) immunotherapeutic composition, such as a DNA vaccine expressing HIV antigen(s), can be used to prime the immune system of a subject, and a yeast-based HIV immunotherapeutic composition of the invention is used to boost the immune response. In one embodiment, a yeast-based immunotherapeutic composition of the invention comprising a whole yeast that recombinantly expresses one or more HIV antigens described herein is used to prime the immune system of a subject, alone or together with a yeast-based immunotherapeutic composition comprising a processed yeast (preferably including one or more HIV antigens, which may be the same antigens as used in the priming dose), followed by additional administrations of the processed yeast as a booster. Alternatively, the booster dose can include, but is not limited to, any other immunotherapeutic composition, including compositions that particularly enhance humoral immune responses, such as a subunit vaccine or an antibody vaccine.

With respect to administration of yeast-based immunotherapeutic compositions described herein, a single composition can be administered to an individual or population of individuals or combinations of such compositions can be administered. Accordingly, two or more compositions can be selected in a "spice rack" approach to most effectively prevent or treat HIV infection in a given individual or population of individuals. This approach can include the administration of different HIV antigens in the context of different yeast-based immunotherapy compositions of the invention (e.g., the use of two or more different yeast-based compositions, each including a different HIV antigen(s)), and/or, within the same protocol, the administration of various forms of the yeast-based immunotherapeutic composition of the invention (e.g., whole recombinant yeast and processed yeast, each including the same or different HIV antigen(s)), and/or, within the same protocol, the use of yeast-based immunotherapeutic compositions with other types of compositions (e.g., other immunotherapy compositions such as autologous T cell vaccines, dendritic cell vaccines, antibody vaccines, subunit vaccines, DNA vaccines; biological response modifiers (described above); small molecule drugs such as a anti-virals, etc.). These various approaches using different compositions can be used in sequential administration protocols and/or by co-administration and/or also consolidated into one injection and/or in separate injections.

In one aspect of the invention, one or more additional therapeutic agents, compounds or compositions (such as any of those described above or elsewhere herein) are administered sequentially with the yeast-based immunotherapy composition. In another embodiment, one or more additional therapeutic agents are administered before the yeast-based immunotherapy composition is administered. In another embodiment, one or more additional therapeutic agents, compounds or compositions are administered after the yeast-based immunotherapy composition is administered. In one embodiment, one or more additional therapeutic agents, compounds or compositions are administered in alternating doses with the yeast-based immunotherapy composition, or in a protocol in which the yeast-based composition is administered at prescribed intervals in between or with one or more consecutive doses of the additional therapeutic agents, compounds or compositions, or vice versa. In one embodiment, one or more additional therapeutic agents are administered together with the yeast-based immunotherapy composition (e.g., together in the same composition or concurrently as separate compositions). In one embodiment, the yeast-based immunotherapy composition is administered in one or more doses over a period of time prior to commencing the administration of the additional therapeutic agents, compounds or compositions. In other words, the yeast-based immunotherapy composition is administered as a monotherapy for a period of time, and then the therapeutic agents, compounds or compositions are added, either concurrently with new doses of yeast-based immunotherapy, or in an alternating fashion with yeast-based immunotherapy. Alternatively, the therapeutic agents, compounds or compositions may be administered for a period of time prior to beginning administration of the yeast-based immunotherapy composition. In one aspect, the yeast is engineered to express or carry the agent, or a different yeast is engineered or produced to express or carry the agent or compound.

In one aspect of the invention, when a treatment course of anti-viral compound therapy begins, additional doses of the immunotherapeutic composition are administered over the same period of time, or for at least a portion of that time, and may continue to be administered once the course of anti-viral compound has ended. However, the dosing schedule for the immunotherapy over the entire period may be, and is expected to typically be, different than that for the anti-viral compound. For example, the immunotherapeutic composition may be administered daily, weekly, biweekly, monthly, bimonthly, or every 3-6 months, or at longer intervals as determined by the physician, and is most typically administered weekly followed by monthly or monthly, where current anti-virals for HIV are administered daily. During an initial period of monotherapy administration of the immunotherapeutic composition, if utilized, the immunotherapeutic composition is preferably administered weekly for between 4 and 12 weeks, followed by monthly administration (regardless of when the anti-viral therapy is added into the protocol). In one aspect, the immunotherapeutic composition is administered weekly for four or five weeks, followed by monthly administration thereafter, until conclusion of the complete treatment protocol.

In one aspect of the invention, an immunotherapeutic composition and other agents, compounds or compositions can be administered together (concurrently). As used herein, concurrent use does not necessarily mean that all doses of all compounds are administered on the same day at the same time. Rather, concurrent use means that each of the therapy components (e.g., immunotherapy and anti-viral therapy) are started at approximately the same period (within hours, or up to 1-7 days of each other) and are administered over the same general period of time, noting that each component may have a different dosing schedule (e.g., immunotherapy monthly, anti-viral daily). In addition, before or after the concurrent administration period, any one of the agents or immunotherapeutic compositions can be administered without the other agent(s).

As used herein, the term "anti-viral" refers to any compound or drug, typically a small-molecule inhibitor or antibody, which targets one or more steps in the virus life cycle with direct anti-viral therapeutic effects. In one embodiment of the invention, the anti-viral compound or drug to be administered in the same therapeutic protocol with an immunotherapeutic composition of the invention is selected from: non-nucleoside reverse transcriptase inhibitors (NNRTI), nucleoside analogue reverse transcriptase inhibitors (NRTIs), integrase inhibitors and entry inhibitors. Typical NRTIs include, but are not limited to: zidovudine (AZT) or tenofovir (TDF) and lamivudine (3TC) or emtricitabine (FTC). In one embodiment, the anti-viral compound is a fixed dose combination (FDCs), comprised of cross-class drugs provided as a single pill taken once daily. Such FDCs include, but are not limited to: ATRIPLA® (tenofovir disoproxil fumarate/emtricitabine/efavirenz: tenofovir/NRTI+emtricitabine/NRTI, with efavirenz (a non-nucleoside reverse transcriptase inhibitor (NNRTI) from Bristol Myers-Squibb), Gilead Sciences, Inc.), COMPLERA® (tenofovir disoproxil fumarate/emtricitabine/rilpivirine: tenofovir/NRTI+emtricitabine/NRTI, with rilpivirine (a NNRTI from Tibotec/Johnson & Johnson), Gilead Sciences, Inc.); STRIBILD/QUAD® (tenofovir disoproxil fumarate/emtricitabine/elvitegravir/cobicistat: tenofovir/NRTI+emtricitabine/NRTI, with cobicistat-boosted elvitegravir (integrase inhibitor from Japan Tobacco), Gilead Sciences, Inc.); and 572-TRII® (abcavir/NRTI+lamivudine/NRTI, with dolutegravir (integrase inhibitor from Pfizer/Shionogi), ViiV (GlaxoSmithKline, Pfizer, Shionogi). Anti-virals useful in the invention include any analog or derivative of any of these compounds, or any composition comprising or containing such compound, drug, analog or derivative.

In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to treat or protect include humans, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); Current Protocols in Molecular Biology (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000); Casarett and Doull's *Toxicology The Basic Science of Poisons*, C. Klaassen, ed., 6th edition (2001), and *Vaccines*, S. Plotkin and W. Orenstein, eds., 3rd edition (1999).

General Definitions

A "TARMOGEN®" (GlobeImmune, Inc., Louisville, Colo.) generally refers to a yeast vehicle expressing one or more heterologous antigens extracellularly (on its surface), intracellularly (internally or cytosolically) or both extracellularly and intracellularly. TARMOGEN® products have been generally described (see, e.g., U.S. Pat. No. 5,830,463). Certain yeast-based immunotherapy compositions, and methods of making and generally using the same, are also described in detail, for example, in U.S. Pat. Nos. 5,830,463, 7,083,787, 7,736,642, Stubbs et al., *Nat. Med.* 7:625-629 (2001), Lu et al., *Cancer Research* 64:5084-5088 (2004), and in Bernstein et al., Vaccine 2008 Jan. 24; 26(4):509-21, each of which is incorporated herein by reference in its entirety.

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

In general, the term "biologically active" indicates that a compound (including a protein or peptide) has at least one detectable activity that has an effect on the metabolic or other processes of a cell or organism, as measured or observed in vivo (i.e., in a natural physiological environment) or in vitro (i.e., under laboratory conditions).

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA, immunoblot assays, etc.).

Reference to a protein or polypeptide used in the present invention includes full-length proteins, fusion proteins, or any fragment, domain, conformational epitope, or homologue of such proteins, including functional domains and immunological domains of proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 91% identical, or at least about 92% identical, or at least about 93% identical, or at least about 94% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

A homologue may include proteins or domains of proteins that are "near full-length", which means that such a homologue differs from the full-length protein, functional domain or immunological domain (as such protein, functional domain or immunological domain is described herein or otherwise known or described in a publicly available sequence) by the addition of or deletion of 1, 2, 3, 4, 5, 6, 7, 8, 9, or 10 amino acids from the N- and/or the C-terminus of such full-length protein or full-length functional domain or full-length immunological domain.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors.

Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example describes the production of multiple yeast-based immunotherapeutic compositions for the treatment or prevention of human immunodeficiency virus (HIV) infection.

The following method is used to produce a yeast expressing any of the HIV antigens described herein (e.g., an antigen comprising any of SEQ ID NOs:1-75).

HIV genes are produced synthetically, from oligonucleotide precursors and are codon-optimized for expression in yeast.

HIV genes are placed under control of the copper-inducible CUP1 promoter in Yeast (*Saccharomyces cerevisiae*) 2 um expression plasmids using standard cloning procedures.

The resulting plasmids are introduced into *Saccharomyces cerevisiae* W303α yeast by Lithium acetate/polyethylene glycol transfection, and primary transfectants are selected on solid minimal plates lacking uracil (UDM; uridine dropout medium). Colonies are re-streaked onto UDM or ULDM (uridine and leucine dropout medium) and allowed to grow for 3 days at 30° C. Liquid cultures lacking uridine (U2 medium: 20 g/L glucose; 6.7 g/L of yeast nitrogen base containing ammonium sulfate; 0.04 mg/mL each of histidine, leucine, tryptophan, and adenine) or lacking uridine and leucine (UL2 medium: 20 g/L glucose; 6.7 g/L of yeast nitrogen base containing ammonium sulfate; and 0.04 mg/mL each of histidine, tryptophan, and adenine) are inoculated from plates and starter cultures are grown for 20 h at 30° C., 250 rpm. Primary cultures are used to inoculate final cultures of the same formulation and growth was continued until a density or 1.1 to 4.0 YU/mL is reached.

Cultures are induced with 400 µM copper sulfate at this starting density of 1-4 YU/ml for 3 hours at 30° C. The cells from each culture are then harvested, PBS-washed and heat-killed at 56° C. for 1 hour in PBS.

After heat-kill of the cultures, the cells are thrice washed in PBS and total protein is isolated by glass bead rupture followed by boiling in SDS lysis buffer. Quantification of total protein is done by amidoschwarz/nitrocellulose binding assay, and HIV antigen content is measured by Western blot using an anti-His tag monoclonal antibody probe followed by interpolation to a His-tagged HCV NS3 protein standard curve.

Example 2

The following example describes an assay for use in evaluating APL antigens of the invention.

The assay is comprised of HLA-A2 transgenic mice, those expressing HLA-A*0201, in addition to the natural mouse MHC genes. Yeast-based immunotherapeutics expressing Gag-APL antigens that protect HLA-A2 mice from challenge with wild-type Gag-expressing tumors, and that do so with greater potency than yeast-based immunotherapeutics expressing the wild-type Gag sequence would be considered to be candidates for therapeutic use in HIV-infected patients.

In one aspect of the invention, APLs are identified that induce higher than wild type efficacy by immunizing mice with synthetic peptides mixed with wild-type empty vector yeast. Based on the results of the peptide screen, only those with enhanced efficacy will be produced recombinantly in yeast, and these selected lead candidate vaccines will then be validated in the HLA-A2 model described above.

Example 3

The following example describes results from experiments utilizing a yeast-based immunotherapeutic known as GI-2010, which is a whole, heat-killed *Saccharomyces cerevisiae* expressing HIV-1 Gag antigen represented by SEQ ID NO:74.

FIG. 1 demonstrates that GI-2010 generates HLA-A2-specific, Gag Sector 1 and Sector 3-specific T cell responses in HLA-A2 transgenic mice. Briefly, to evaluate whether GI-2010 generates immune responses targeting these sectors, the inventors developed a mouse model in which T cell responses to these elements were measured in human HLA-A*0201 transgenic mice. This haplotype was chosen because of its high prevalence in the general population including in HIV-infected individuals. Mice were immunized subcutaneously once per week for 3 weeks with 5 Y.U. of GI-2010 or the control (empty vector) yeast known as YVEC, and then rested for 13 days. Splenocytes and lymph nodes were harvested and combined at a ratio of 4:1 and then incubated with recombinant p24 (206 amino acid capsid protein region of Gag, rich in sector 3 residues), provided at 5 µg/mL or 1 µg/mL; or the C-terminal 94 residues of p24 (denoted s3.2, also rich in Sector 3 residues), provided at 1 µg/mL; or recombinant p17 (132 amino acid region of Gag matrix protein, rich in Sector 1 residues), provided at 1 µg/mL, for 4 days. The cells were then transferred to IFNγ ELISpot plates to evaluate the number of T cells producing this cytokine in response to vaccination and to in vitro stimulation (IVS) with each recombinant antigen. The results, shown in FIG. 1, indicate that GI-2010 vaccination mounts T cell responses specific to both Sector 1 and Sector 3 epitopes and that these responses require Yeast-Gag vaccination, since unvaccinated mice (Naïve) or those immunized with empty vector control yeast (YVEC) did not produce the effect.

Referring to FIG. 1, this figure illustrates the IFN-γ ELISpot response in GI-2010 vaccinated mice to in vitro stimulation with recombinant Gag antigens rich in Sector 1 and 3 residues. X-axis labels identify antigens used in the IVS: P24-5 and P24-1 recombinant purified HIV p24 capsid protein at 5 and 1 µg/mL, respectively; p17, recombinant purified HIV p17 matrix protein at 1 µg/mL; s3.2, recombinant purified C-terminal 94 amino acids of p24 at 1 µg/mL. S.I., stimulation index (spots # antigen-treated IVS/spot# media alone IVS).

To create a high resolution functional map of GI-2010-induced immune responsiveness, the inventors next conducted an IFNγ ELISpot screening assay in which an unbiased comprehensive panel of 44 15-mer peptides, overlapping by 9 residues and spanning sector 3 was tested for the ability to in vitro stimulate T cells harvested from GI-2010-immunized mice. BALB/C mice were subcutaneously vaccinated once per week for 3 weeks. One week after the third immunization, splenocytes were harvested and incubated with individual peptides at 25 µM final concentration for 4 days in the presence of 20 U/mL of recombinant murine IL-2 (quadruplicate IVS wells per peptide treatment). Cells were transferred to IFNγ ELISpot plates for 24 h and spots were then developed.

Figure 2:
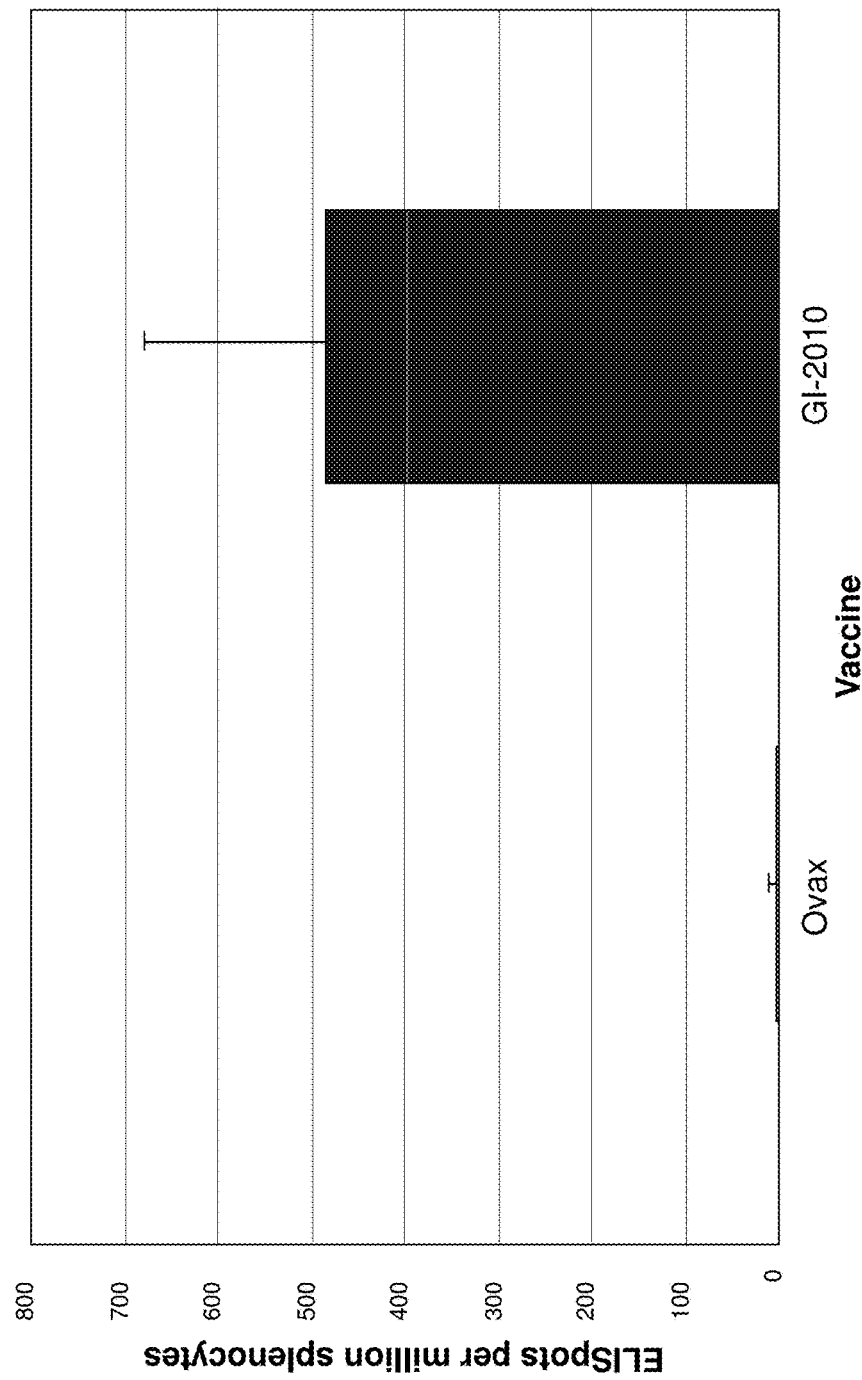
FIG. 2 is a graph showing interferon-γ (IFN-γ) ELISpot responses of GI-2010 vaccinated BALB/c mice to in vitro stimulation with sector 3 peptide YVDRFYKTLRAEQAS (SEQ ID NO:84).

The results, shown in FIG. 2, indicate that one peptide (YVDRFYKTLRAEQAS; SEQ ID NO:84) elicited a strong IFNγ response in mice immunized with GI-2010 but not in mice immunized with the Yeast-Ovax, which is a yeast expressing the irrelevant antigen chicken ovalbumin (p=0.028, ANOVA). The ratio of spot counts for GI-2010 to Ovax immunized mice was 170:1, demonstrating the specificity of the response. Notably, this HIV peptide (SEQ ID NO:84) contains two sector 3 residues and completely overlaps a sequence (DA9) that is essential for viral replication and was identified as an immunodominant epitope in a long term HIV non-progressor (Wagner et. al. (1999) 162:3727-3734). These data further indicate that GI-2010, or yeast-HIV immunotherapeutics comprising Sector 3 epitopes, generates T cell responses targeting an immunologically vulnerable region of Gag that are implicated in control of HIV.

Figure 3:
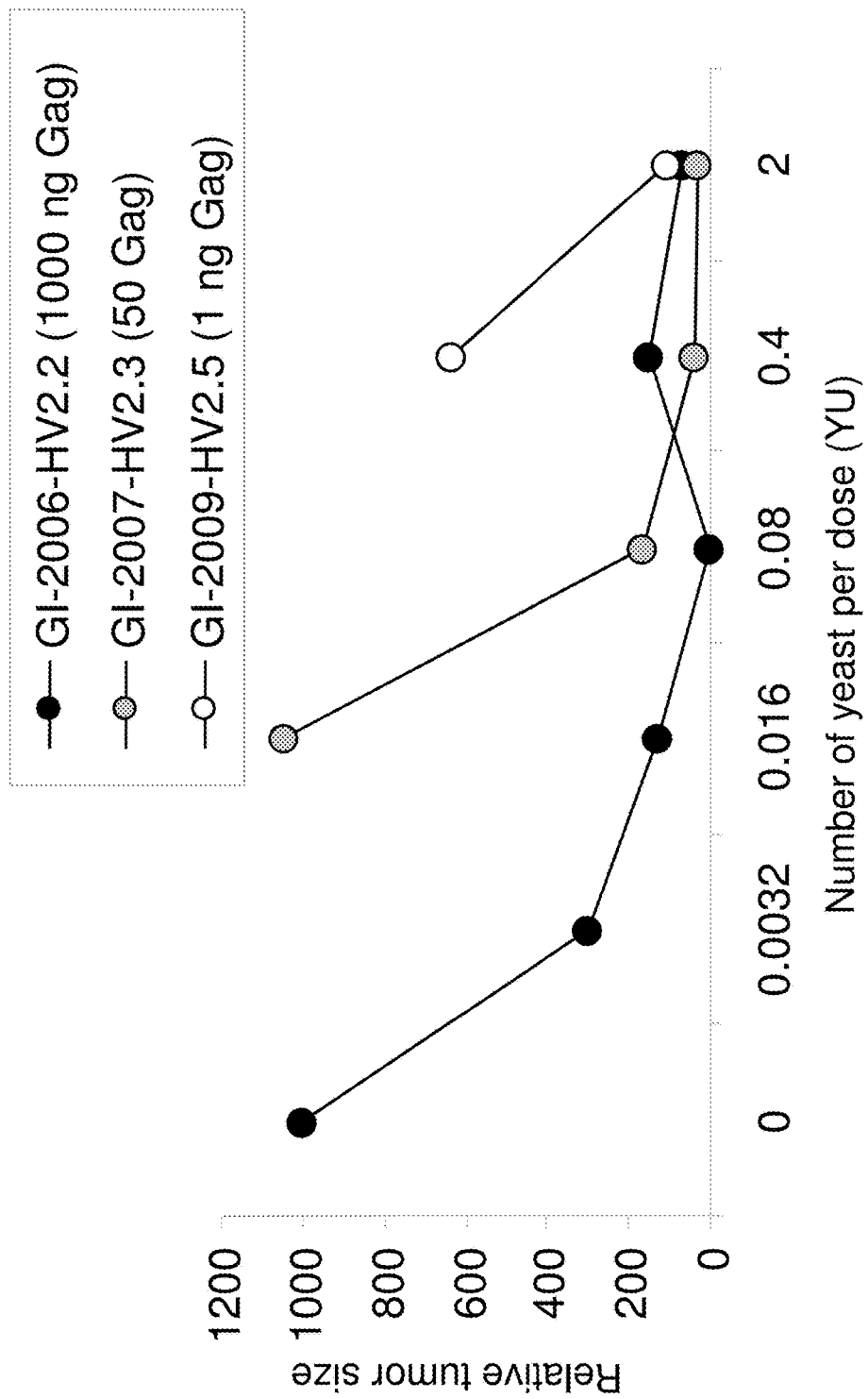
FIG. 3 is a graph showing dose-dependent killing of targets (B16 tumor cells) expressing HIV-Gag by cells from mice immunized with HIVAX-2 yeast (Gag-expressing, engineered to express different levels of Gag antigen) at the indicated yeast doses (X-axis).

FIG. 3 compares results from separate experiments in which groups of 6-8 mice were vaccinated with PBS alone or with the indicated number of heat-killed HIVAX-2 yeast (yeast expressing an HIV-1 Gag antigen represented by SEQ ID NO:74) and challenged with B16-gag tumors. These results show that protective immunity in this model requires a minimal number of yeast per dose (approximately 0.1 YU or $1\times10^6$) as well as a minimal amount of Gag antigen expressed per yeast (approximately 20 ng per YU).

Example 4

The following example describes the design and production of a yeast-based immunotherapeutic composition for HIV, known as GI-2013.

In this experiment, yeast were engineered to express a novel HIV fusion protein antigen under the control of the copper-inducible promoter, CUP1. More specifically, *Saccharomyces cerevisiae* were engineered to express conserved, contiguous regions of HIV Gag p24 and p2, fused to one of the most highly conserved regions of HIV Pol, the Pol protease, and also to portions of Pol RNase H and Pol Integrase, under the control of the copper-inducible promoter, CUP1. The HIV fusion protein was a single polypeptide comprising the following HIV sequence elements fused in frame from N- to C-terminus, represented by SEQ ID NO:5: 1) the amino acid sequence of an HIV p24 protein (positions 1-231 of SEQ ID NO:5); 2) the amino acid sequence of an HIV Gag p2 protein (positions 232-245 of SEQ ID NO:5); 3) the amino acid sequence of a portion of HIV Pol protease, lacking the N-terminal 19 amino acids which are well conserved among HIV strains (positions 246-325 of SEQ ID NO:5); 4) the amino acid sequence of an HIV Pol RNase H protein (positions 326-445 of SEQ ID NO:5); and 5) the amino acid sequence of a portion of an HIV Pol Integrase protein (positions 446-567 of SEQ ID NO:5). The amino acid at position 251 of SEQ ID NO:5 is an aspartate in native HIV Pol protease, but is substituted with an alanine in SEQ ID NO:5 in order to eliminate protease activity by the fusion protein. The Pol Integrase portion of the fusion protein lacks the C-terminal 166 amino acids of the native protein to ensure that the catalytic function of the integrase was excluded from the fusion protein.

Figure 4:
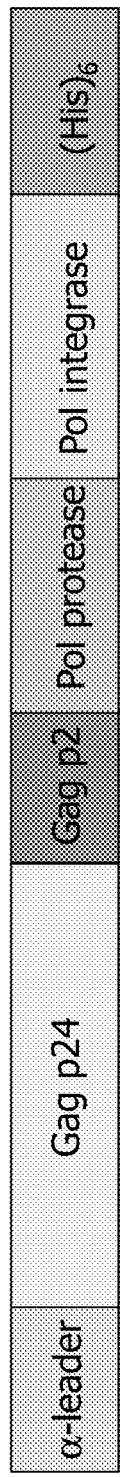
FIG. 4 is a schematic drawing showing the structure of the fusion protein expressed by the yeast-HIV immunotherapeutic known as GI-2013.

For stable expression in yeast, the fusion protein further includes an alpha factor leader sequence represented by SEQ ID NO:82 at the N-terminus of the fusion protein, which is fused to a two amino acid linker sequence of Thr-Ser, which is fused to the N-terminus of the HIV p24 protein, or the N-terminus of SEQ ID NO:5. The fusion protein further includes a hexahistidine sequence fused to the C-terminus (i.e., fused to the C-terminus of the HIV Pol Integrase protein of SEQ ID NO:5). The amino acid sequence of the entire fusion protein, including the N-terminal alpha factor leader sequence, linker sequence, HIV sequences, and C-terminal hexahistidine sequence is represented herein by SEQ ID NO:86, containing the following sequence elements fused in frame from N- to C-terminus: 1) the amino acid sequence of an alpha factor leader sequence (SEQ ID NO:82, positions 1-89 of SEQ ID NO:86); 2) a two amino acid linker sequence of Thr-Ser (positions 90-91 of SEQ ID NO:86); 3) the amino acid sequence of an HIV p24 protein (positions 1-231 of SEQ ID NO:5; positions 92-322 of SEQ ID NO:86); 4) the amino acid sequence of an HIV Gag p2 protein (positions 232-245 of SEQ ID NO:5; positions 323-336 of SEQ ID NO:86); 5) the amino acid sequence of a portion of HIV Pol protease, lacking the N-terminal 19 amino acids which are well conserved among HIV strains (positions 246-325 of SEQ ID NO:5; positions 337-416 of SEQ ID NO:86); 6) the amino acid sequence of an HIV Pol RNase H protein (positions 326-445 of SEQ ID NO:5; positions 417-536 of SEQ ID NO:86); 7) the amino acid sequence of a portion of an HIV Pol Integrase protein (positions 446-567 of SEQ ID NO:5; positions 537-658 of SEQ ID NO:86); and 8) a hexahistidine sequence (positions 659-664 of SEQ ID NO:86). FIG. 4 is a schematic illustration of the structure of this fusion protein.

A nucleic acid sequence encoding the fusion protein of SEQ ID NO:86, and accordingly, SEQ ID NO:5 (since SEQ ID NO:5 is contained within SEQ ID NO:86), codon optimized for yeast expression, is represented herein by SEQ ID NO:85. The yeast immunotherapy composition expressing SEQ ID NO:5 is also referred to herein as GI-2013.

The plasmid encoding the α factor leader-p24-p2-Pol protease-Pol integrase-hexahistidine tag fusion protein of SEQ ID NO:86 (also referred to herein as "HIVfuse") was transfected into W303α yeast by a standard Lithium Acetate-polyethylene glycol method. Primary transfectants were selected on uridine dropout agar (UDA) plates, and single colony isolates were re-streaked onto yeast agar medium lacking only uracil (UDA) or lacking both uracil and leucine (ULDA) to further purify transfectant clones.

Figure 5:
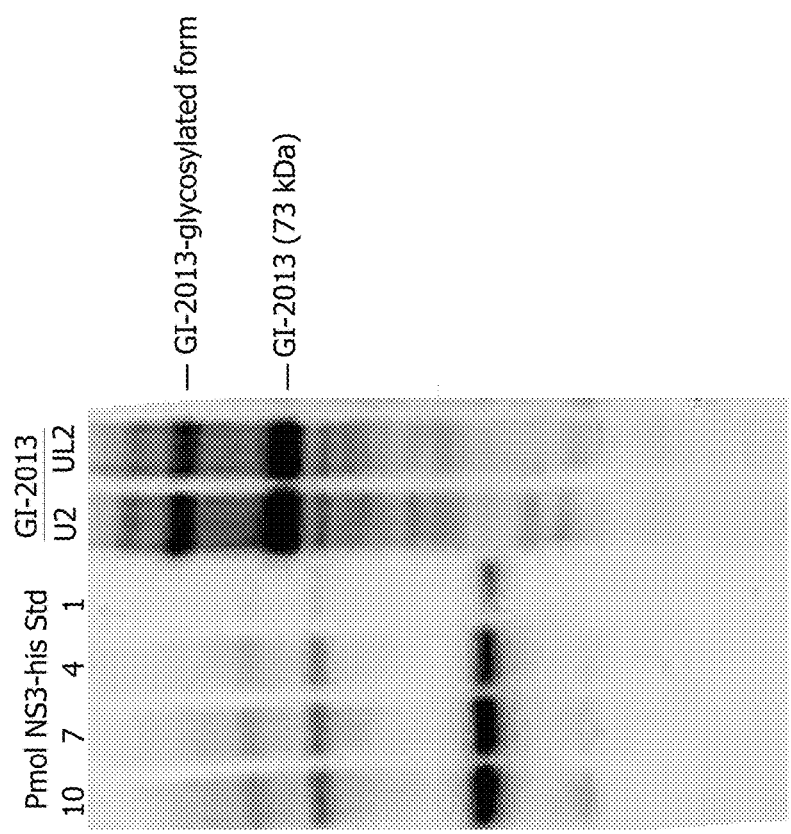
FIG. 5 is a digital image of a Western blot showing the expression of fusion protein by the yeast-immunotherapeutic, GI-2013, in both U2 and UL2 media.

Single colonies from UDA or ULDA plates were used to inoculate a 25 mL culture of U2 or UL2 liquid media and the cultures incubated for 16 h at 30° C. (starter culture). Starter cultures were used to inoculate final cultures or U2 or UL2 to a density of 0.2 YU/mL, which were the incubated with shaking until a density of 2-3 YU/mL was reached. Cultures were then induced with 500 µM copper sulfate for 3 hours at 30° C., washed once in PBS, heat inactivated at 56° C. for 1 h, and washed three times in PBS. Extraction and quantification of total yeast protein and measurement of the "HIVfuse" antigen (SEQ ID NO:86) content by Western blot were conducted per standard procedures, using an anti-his tag monoclonal antibody for detection. The results showed that the fusion protein was expressed to exceptionally high levels, at up to 23% of the total yeast cellular protein (14,000 Ng/YU). The results are shown in FIG. 5.

Example 5

The following example describes the results of immunization with the yeast-HIV immunotherapeutic composition known as GI-2013.

To demonstrate the ability of GI-2013 to elicit HIV antigen-specific immune responses in vivo, six week old BALB/c mice were immunized subcutaneously at 2 sites (right and left flank) with 2.5 YU/site of GI-2013 or control yeast expressing chicken ovalbumin (referred to as OVAX). Immunization was conducted once per week for 3 weeks. Seven days after the third immunization, mice were sacrificed and spleens were removed, processed into single cell suspensions, and depleted of red blood cells by ammonium chloride/potassium carbonate based lysis. After washing in complete RPMI plus 10% fetal bovine serum, cells were counted and placed into in vitro stimulation (IVS) for 4 days with a centrifugally cleared lysate of GI-2013 (source of HIVfuse; equivalent to 6 µg/mL antigen).

The stimulated immune cells were then subjected to ELISpot analysis or $^3$H Thymidine incorporation (lymphocyte proliferation assay, LPA).

Figure 6:
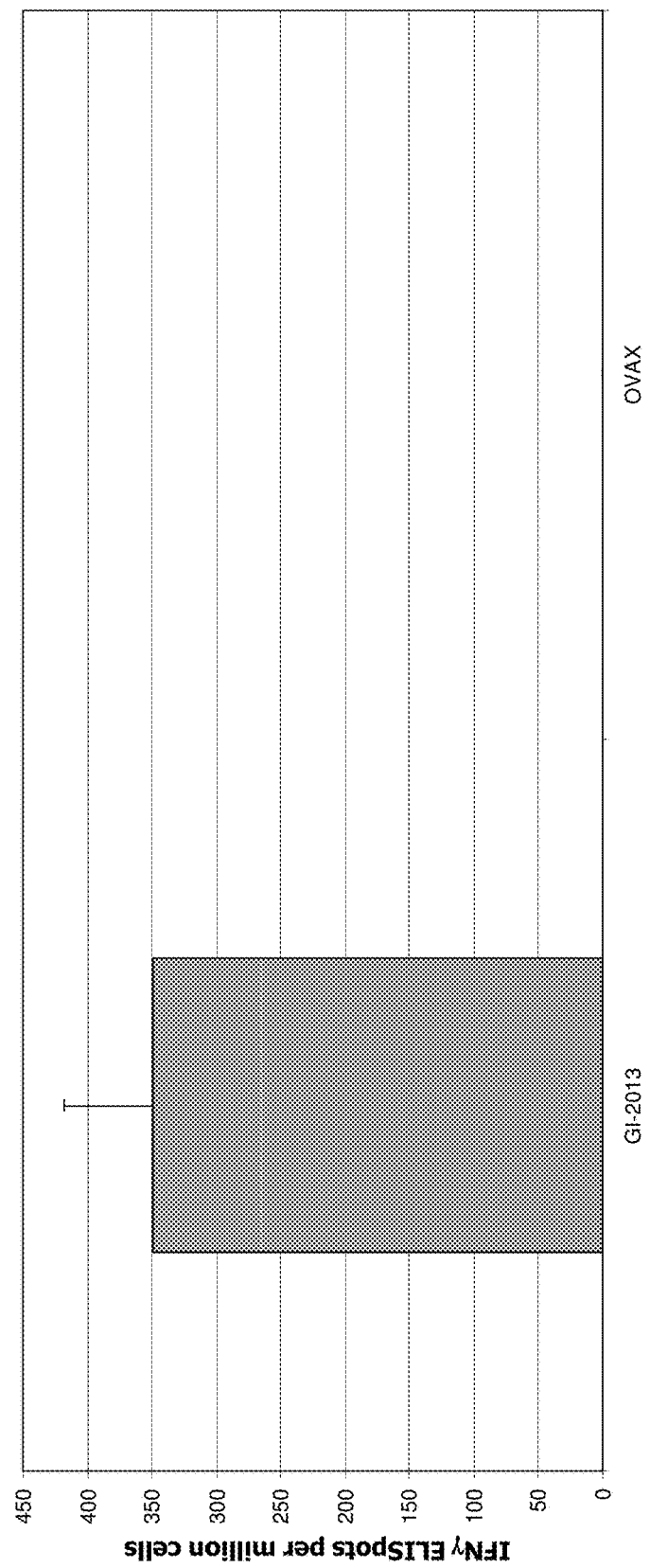
FIG. 6 is a graph showing antigen-specific interferon-γ (IFN-γ) ELISpot responses in GI-2013 immunized BALB/c mice (dark bar) as compared to OVAX (control) immunized mice (zero response detected for OVAX in this experiment).

For ELISpot assays, 200,000 cells per well were transferred IFNγ/IL2 dual color ELISpot plates (R&D systems) after four days of IVS. ELISpots were developed 20 h later per manufacturer's instructions and spot counts were determined by Cellular Technology Limited (Shaker Heights, Ohio). As shown in FIG. 6, the Y-axis values correspond to spot counts in HIV antigen-stimulated wells minus spot counts obtained in media wells (no stimulation). Media-subtracted values for the OVAX group were slightly negative and therefore assigned as zero as negative ELISpot values are undefined (Error bars, standard deviations). The results shown in FIG. 6 demonstrate that GI-2013 elicits a strong HIV antigen-specific IFNγ response.

Figure 7:
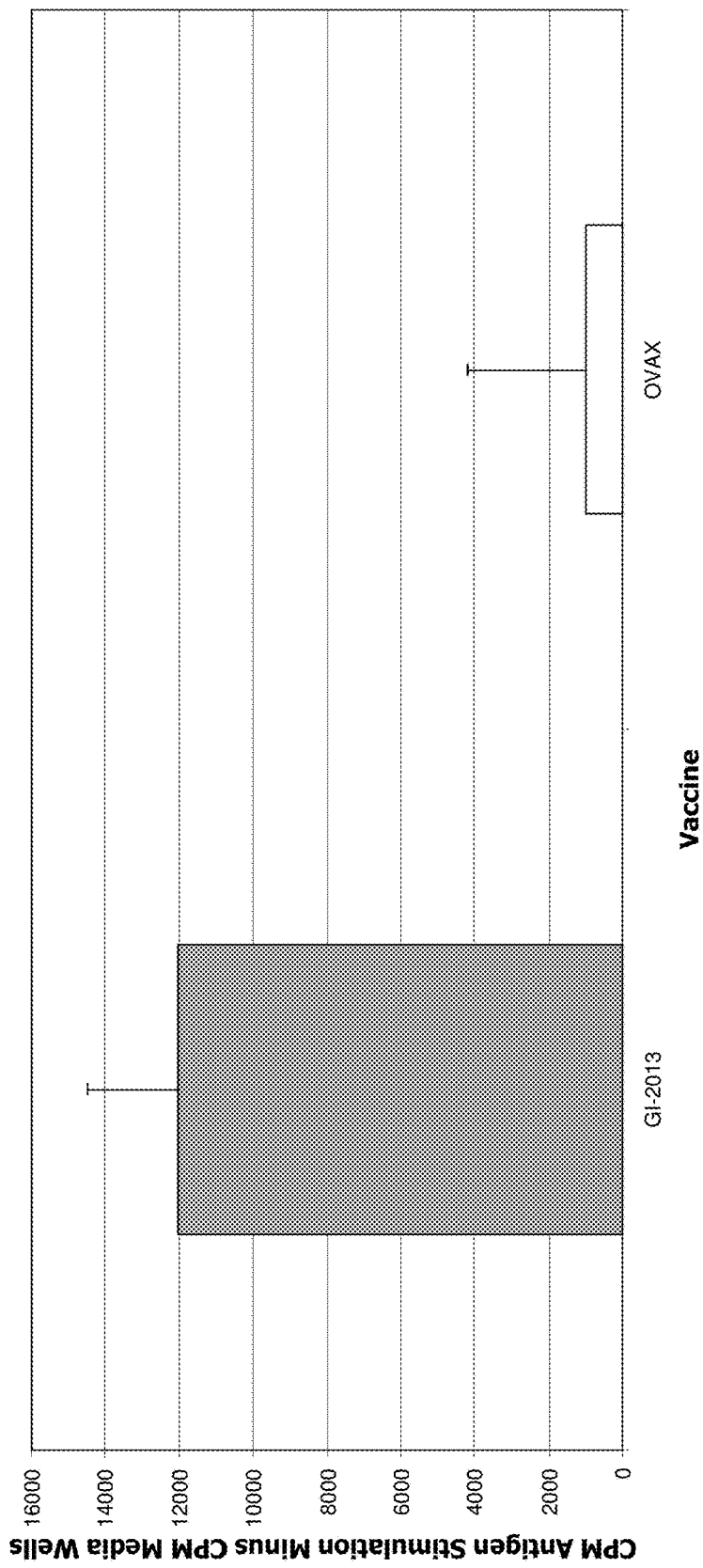
FIG. 7 is a graph showing antigen-specific lymphocyte proliferation in GI-2013 immunized BALB/c mice (dark bar) as compared to OVAX (control) immunized mice (white bar).

For lymphocyte proliferation assays (LPAs), 1 µCi of $^3$H Thymidine was added to each well of stimulated splenocytes (200,000 cells) in 20 µL of complete RMPI for 20 h. Cells were harvested and processed for scintillation counting per standard procedures. As shown in FIG. 7, the Y-axis values correspond to average counts per minute (cpm) in HIV antigen-stimulated wells minus cpm obtained in media wells (no stimulation). A minimum of 4 independent replicate IVS wells were processed for each condition (Error bars, standard deviations). The results show that GI-2013 elicits a strong HIV-antigen specific lymphocyte proliferative response (GI-2013/OVAX response ratio of ~12).

Therefore, GI-2013 generated a robust immune response in vivo, in particular, by eliciting cellular immune responses believed to be effective in the context of HIV infection.

Example 6

The following example describes a clinical study for the treatment of HIV.

An open-label dose escalation phase 1b/2a clinical trial is run using a yeast-based HIV immunotherapy composition described herein as GI-2010 (comprising SEQ ID NO:74), or using a a yeast-based HIV immunotherapy composition described herein as GI-2013 (comprising SEQ ID NO:5 or SEQ ID NO:86). Other yeast-based HIV immunotherapy compositions described herein can be utilized in a similar phase 1 clinical trial. Subjects are infected with human immunodeficiency virus type 1 (HIV-1) and their disease is under control using HAART therapy.

Subjects meeting these criteria are administered the yeast-based HIV immunotherapy composition in a sequential dose cohort escalation protocol utilizing dose ranges from 0.05 Y.U. to 80 Y.U. (e.g., 0.05 Y.U., 10 Y.U., 20 Y.U., and 40-80 Y.U.). In one protocol, 5 weekly doses will be administered subcutaneously (weekly dosing for 4 weeks), followed by 2-4 monthly doses also administered subcutaneously, with continued anti-viral therapy during treatment with the yeast-based HIV immunotherapy (prime-boost protocol). In a second protocol, a 4-weekly dosing protocol is followed, where subjects receive a total of three doses administered on day 1, week 4 and week 8, using the same escalating dose strategy as set forth above. Optionally, in one study, a single patient cohort (5-6 patients) will receive subcutaneous injections of placebo (PBS) on the same schedule as the immunotherapy plus continued anti-viral therapy.

In the second expansion stage of this trial, subjects receive the highest safe dose as determined above and are treated for 6 months to 1 year in conjunction with continued anti-viral therapy.

Safety, viral load, CD4$^+$ T cell counts, and immunogenicity (e.g., antigen-specific T cell responses measured by ELISpot) are assessed. The yeast-based HIV immunotherapy composition is expected to provide a therapeutic benefit to HIV-infected patients. The immunotherapy is expected to be safe and well-tolerated at all doses delivered. Patients receiving at least the highest dose of yeast-based HIV immunotherapy are expected to show treatment-emergent, HIV-specific T cell responses as determined by ELISPOT. Patients receiving yeast-based HIV immunotherapy are expected to show improvement in viral load control and/or improved CD4 T cell counts as compared to the anti-viral group and/or as compared to the placebo controlled group, if utilized.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An immunotherapeutic composition comprising:
   a) a yeast vehicle; and
   b) a fusion protein comprising HIV antigens, wherein the HIV antigens comprise an amino acid sequence that is at least 90% identical to SEQ ID NO:11.

2. The immunotherapeutic composition of claim 1, wherein the HIV antigens comprise an amino acid sequence that is at least 95% identical to SEQ ID NO:11.

3. The immunotherapeutic composition of claim 1, wherein the HIV antigens comprise SEQ ID NO:11.

4. The immunotherapeutic composition of claim 1, wherein the HIV antigens consist of the amino acid sequence of SEQ ID NO:11.

5. The immunotherapeutic composition of claim 1, wherein the fusion protein comprises an amino acid sequence of SEQ ID NO:11.

6. The immunotherapeutic composition of claim 1, wherein the yeast vehicle is a whole, killed or inactivated yeast.

7. An immunotherapeutic composition comprising:
   a) a whole, inactivated yeast; and
   b) an HIV fusion protein comprising the amino acid sequence of SEQ ID NO:11, wherein the fusion protein is under the control of the promoter CUP1;
   wherein the HIV fusion protein is expressed by the yeast; and
   wherein the composition elicits an HIV-specific T cell response.

8. An immunotherapeutic composition comprising:
   a) a yeast; and b) an HIV antigen expressed by the yeast and comprising an HIV Gag protein, wherein the HIV Gag protein forms virus-like particles (VLPs) when expressed by the yeast, wherein the HIV antigen comprises SEQ ID NO:11.

9. An immunotherapeutic composition comprising:
   a) a yeast vehicle; and
   b) at least one HIV antigen that is an HIV Gag antigen comprising Sector 3epitopes and/or Sector 1 epitopes, wherein the HIV antigen comprises SEQ ID NO:11.

10. The immunotherapeutic composition of claim 1, wherein the yeast is from *Saccharomyces cerevisiae*.

11. The immunotherapeutic composition of claim 1, wherein the composition is formulated in a pharmaceutically acceptable excipient suitable for administration to a subject by injection.

12. A fusion protein comprising HIV antigens, wherein the fusion protein comprises an amino acid sequence that is at least 95% identical to an amino acid sequence of: SEQ ID NO:11.

13. A recombinant nucleic acid molecule encoding the fusion protein of claim 12.

14. An isolated cell transfected with the recombinant nucleic acid molecule of claim 13.

15. A method to treat human immunodeficiency virus (HIV) infection or at least one symptom resulting from HIV infection in a subject, comprising administering to a subject that has been infected with HIV at least one composition according to claim 1, wherein administration of the composition to the subject reduces HIV infection or at least one symptom resulting from HIV infection in the subject.

16. The method of claim 15, further comprising administering to the subject one or more additional compounds or compositions useful for treating or ameliorating a symptom of HIV infection.

17. The method of claim 16, wherein the one or more additional compounds or compositions is selected from the group consisting of: a fixed-dose combination (FDC) drug; a DNA vaccine encoding at least one HIV antigen; a processed yeast; autologous T cells from the subject, wherein the autologous T cells have been stimulated ex vivo with at least one HIV antigen; a protein subunit vaccine comprising at least one HIV antigen, and a biological response modifier.

18. The method of claim 16, wherein the additional compound or composition is administered prior to administration of the immunotherapeutic composition, subsequent to the administration of the immunotherapeutic composition, or concurrently with administration of the immunotherapeutic composition.

19. A method to immunize a population of individuals against HIV, comprising administering to the population of individuals at least one composition according to claim 1.

\* \* \* \* \*

UNITED STATES PATENT AND TRADEMARK OFFICE
CERTIFICATE OF CORRECTION

PATENT NO. : 10,265,393 B2
APPLICATION NO. : 15/698450
DATED : April 23, 2019
INVENTOR(S) : Thomas H. King and David Apelian Page 1 of 1

It is certified that error appears in the above-identified patent and that said Letters Patent is hereby corrected as shown below:

In the Claims

In Column 128, Claim 9, Lines 65-67, please delete:
"b) at least one HIV antigen that is an HIV Gag antigen comprising Sector 3epitopes and/or Sector 1 epitopes, wherein the HIV antigen comprises SEQ ID NO:11."

And insert:
--b) at least one HIV antigen that is an HIV Gag antigen comprising Sector 3 epitopes and/or Sector 1 epitopes, wherein the HIV antigen comprises SEQ ID NO:11.--

Signed and Sealed this
Eighteenth Day of June, 2019

Andrei Iancu
*Director of the United States Patent and Trademark Office*